United States Patent
Nielsen et al.

(10) Patent No.: US 7,018,829 B1
(45) Date of Patent: Mar. 28, 2006

(54) METABOLICALLY ENGINEERED MICROBIAL CELL WITH AN ALTERED METABOLITE PRODUCTION

(75) Inventors: Jens Nielsen, Charlottenlund (DK); Torben Lauesgaard Nissen, Frederiksberg (DK); Morten C. Kielland-Brandt, Copenhagen (DK)

(73) Assignee: Fluxome Sciences A/S, Kongens Lyngby ( * ) Notice: Subject to any disclaimer, the term of this patent is extended or adjusted under 35 U.S.C. 154(b) by 0 days.

(21) Appl. No.: 09/743,414

(22) PCT Filed: Jul. 12, 1999

(86) PCT No.: PCT/DK99/00397

§ 371 (c)(1),
(2), (4) Date: Jun. 14, 2001

(87) PCT Pub. No.: WO00/03020

PCT Pub. Date: Jan. 20, 2000

(30) Foreign Application Priority Data

Jul. 10, 1998 (DK) ............................... 1998 00967

(51) Int. Cl.
*C12N 1/16* (2006.01)
*C12N 1/19* (2006.01)
*C12N 15/81* (2006.01)
*C12P 7/06* (2006.01)
*A01N 63/02* (2006.01)

(52) U.S. Cl. .............................. 435/254.2; 435/254.21; 435/254.23; 435/161; 435/471; 435/483

(58) Field of Classification Search ............. 435/252.3, 435/69.1, 320.1, 471, 440; 536/23.1
See application file for complete search history.

(56) References Cited

U.S. PATENT DOCUMENTS 5,830,716 A 11/1998 Kojima et al.

FOREIGN PATENT DOCUMENTS

| EP | 0733712 A1 | 9/1996 |
|---|---|---|
| WO | WO 8703006 | 5/1987 |
| WO | WO 9810089 | 3/1998 |
| WO | WO 9818909 | 5/1998 |

OTHER PUBLICATIONS

Avendaño, et al., "GDH3 Encodes a Glutamate Dehydrogenase Isozyme, a Previously Unrecognized Route for Glutamate Bioxynthesis in *Saccharomyces cerevisiae*," Journal of Bacteriology, 1997, 5594-5597, 179(17).

Voordouw, et al., "Structure of Pyridine Nucleotide Transhydrogenase from *Azotobacter vinelandii*," Eur. J. Biochem., 1979, 447-454, 98.

Flores-Samaniego, et al., "Glutamine Synthesis is a Regulatory Signal Controlling Glucose Catabolism in *Saccharomyces cerevisiae*," Journal of Bacteriology, 1993, 7705-7706, 175(23).

Wakisaka, et al., "Characteristics and efficiency of Glutamine Production by Coupling of a Bacterial Glutamine Synthetase Reaction with the Alcoholic Fermentation System of Baker's Yeast," Applied Environmental Microbiology, 1998, 2952-2957, 64(8).

Boonstra, et al., "Sequence of the Soluble Pyridine Nucleotide Transhydrogenase of *Azotobacter vinelandii*," 1999.

Anderlund, et al., "Expression of the *Escherichia coli* pntA and pntB Genes, Encoding Nicotinamide Nucleotide Transhydrogenase, in *Saccharomyces cerevisiae* and Its Effect on Product Formation during Anaerobic Glucose Fermentation," Applied and Environmental Microbiology, 1999, 2333-2340, 65(6).

*Primary Examiner*—Scott D. Priebe
*Assistant Examiner*—Mike Burkhart
(74) *Attorney, Agent, or Firm*—Iver P. Cooper

(57) ABSTRACT

A recombinant microbial cell comprises at least one increased expressible enzyme activity controlling anabolic metabolism of ammonia as a nutrient source, the increased enzyme activity being an NADH-dependent activity catalysing the reaction (a) 2-oxoglutarate+$NH_3$+NADH→glutamate+NAD or being an activity catalysing the reaction
(b) 2-oxoglutarate+glutamine+NADH→2 glutamate+ NAD or being an activity catalysing the reaction
(c) glutamate+$NH_3$+ATP→glutamine+ADP+Pi.

The increased enzyme activity is encoded by a nucleic acid coding sequence linked to an expression signal not natively associated with the nucleic acid coding sequence and is increased as compared to the expression of the enzyme activity when the nucleic acid coding sequence is associated with its native expression signal.

33 Claims, 13 Drawing Sheets

SEQUENCE LISTING

<160> NUMBER OF SEQ ID NOS: 14

<210> SEQ ID NO 1
<211> LENGTH: 1395
<212> TYPE: DNA
<213> ORGANISM: Azotobacter vinelandii
<220> FEATURE:
<221> NAME/KEY: CDS
<222> LOCATION: (1)..(1395)
<223> OTHER INFORMATION:

<400> SEQUENCE: 1

| | | | | | | | | | | | | | | | | |
|---|---|---|---|---|---|---|---|---|---|---|---|---|---|---|---|---|
| atg | gct | gta | tat | aas | tac | gat | gtg | gtg | gta | atc | ggc | aca | ggc | cct | gct | 48 |
| Met | Ala | Val | Tyr | Xaa | Tyr | Asp | Val | Val | Val | Ile | Gly | Thr | Gly | Pro | Ala | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ggc | gaa | ggg | gca | gcg | atg | aat | gcc | gtg | aag | gcc | ggg | cgc | aag | gta | gcg | 96 |
| Gly | Glu | Gly | Ala | Ala | Met | Asn | Ala | Val | Lys | Ala | Gly | Arg | Lys | Val | Ala | |
| | | | 20 | | | | | 25 | | | | | 30 | | | |

| | | | | | | | | | | | | | | | | |
|---|---|---|---|---|---|---|---|---|---|---|---|---|---|---|---|---|
| gtc | gtg | gat | gat | cgc | ccc | cag | gtc | ggc | ggc | aac | tgc | acc | cac | ctc | gga | 144 |
| Val | Val | Asp | Asp | Arg | Pro | Gln | Val | Gly | Gly | Asn | Cys | Thr | His | Leu | Gly | |
| 35 | | | | | 40 | | | | | 45 | | | | | | |

| | | | | | | | | | | | | | | | | |
|---|---|---|---|---|---|---|---|---|---|---|---|---|---|---|---|---|
| acc | att | ccc | tcc | aag | gcg | ctg | cgc | cac | tcg | gtg | cgg | cag | atc | atg | cag | 192 |
| Thr | Ile | Pro | Ser | Lys | Ala | Leu | Arg | His | Ser | Val | Arg | Gln | Ile | Met | Gln | |
| | 50 | | | | | 55 | | | | | 60 | | | | | |

| | | | | | | | | | | | | | | | | |
|---|---|---|---|---|---|---|---|---|---|---|---|---|---|---|---|---|
| tac | aac | aac | aat | ccg | ctg | ttc | cgc | cag | atc | ggc | gag | ccg | cgc | tgg | ttt | 240 |
| Tyr | Asn | Asn | Asn | Pro | Leu | Phe | Arg | Gln | Ile | Gly | Glu | Pro | Arg | Trp | Phe | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| tcc | ttc | gcc | gat | gtc | ctg | aag | agc | gcc | gag | cag | gtc | atc | gcc | aag | cag | 288 |
| Ser | Phe | Ala | Asp | Val | Leu | Lys | Ser | Ala | Glu | Gln | Val | Ile | Ala | Lys | Gln | |
| | | | | 85 | | | | | 90 | | | | | 95 | | |

| | | | | | | | | | | | | | | | | |
|---|---|---|---|---|---|---|---|---|---|---|---|---|---|---|---|---|
| gtt | tcc | tcg | cgg | acc | ggc | tac | tat | gcg | cgc | aac | cgt | atc | gat | acc | ttc | 336 |
| Val | Ser | Ser | Arg | Thr | Gly | Tyr | Tyr | Ala | Arg | Asn | Arg | Ile | Asp | Thr | Phe | |
| | | | 100 | | | | | 105 | | | | | 110 | | | |

| | | | | | | | | | | | | | | | | |
|---|---|---|---|---|---|---|---|---|---|---|---|---|---|---|---|---|
| ttc | ggg | acc | gcg | agc | ttc | tgc | gac | gar | cac | acc | atc | gag | gtc | gtc | cac | 384 |
| Phe | Gly | Thr | Ala | Ser | Phe | Cys | Asp | Glu | His | Thr | Ile | Glu | Val | Val | His | |
| | | 115 | | | | | 120 | | | | | 125 | | | | |

| | | | | | | | | | | | | | | | | |
|---|---|---|---|---|---|---|---|---|---|---|---|---|---|---|---|---|
| ctc | aac | ggt | atg | gtg | gaa | acg | ctg | gtg | gcc | aag | cag | ttc | gtc | atc | gcc | 432 |
| Leu | Asn | Gly | Met | Val | Glu | Thr | Leu | Val | Ala | Lys | Gln | Phe | Val | Ile | Ala | |
| | 130 | | | | | 135 | | | | | 140 | | | | | |

| | | | | | | | | | | | | | | | | |
|---|---|---|---|---|---|---|---|---|---|---|---|---|---|---|---|---|
| acc | ggg | tcg | cgt | ccc | tac | cgc | ccg | gcc | gat | gtc | gat | ttc | acc | cat | ccg | 480 |
| Thr | Gly | Ser | Arg | Pro | Tyr | Arg | Pro | Ala | Asp | Val | Asp | Phe | Thr | His | Pro | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| cgc | atc | tac | gac | agc | gac | acc | atc | ctc | agc | ctc | ggc | cac | acg | ccg | cgc | 528 |
| Arg | Ile | Tyr | Asp | Ser | Asp | Thr | Ile | Leu | Ser | Leu | Gly | His | Thr | Pro | Arg | |
| | | | | 165 | | | | | 170 | | | | | 175 | | |

| | | | | | | | | | | | | | | | | |
|---|---|---|---|---|---|---|---|---|---|---|---|---|---|---|---|---|
| cgg | ttg | atc | atc | tac | gga | gcg | ggg | gtg | atc | ggc | tgc | gaa | tat | gcc | tcc | 576 |
| Arg | Leu | Ile | Ile | Tyr | Gly | Ala | Gly | Val | Ile | Gly | Cys | Glu | Tyr | Ala | Ser | |
| | | | 180 | | | | | 185 | | | | | 190 | | | |

| | | | | | | | | | | | | | | | | |
|---|---|---|---|---|---|---|---|---|---|---|---|---|---|---|---|---|
| atc | ttc | agt | ggg | ctg | ggc | gtg | ctg | gtc | gac | ctc | atc | gac | aac | cgc | gac | 624 |
| Ile | Phe | Ser | Gly | Leu | Gly | Val | Leu | Val | Asp | Leu | Ile | Asp | Asn | Arg | Asp | |
| | | 195 | | | | | 200 | | | | | 205 | | | | |

| | | | | | | | | | | | | | | | | |
|---|---|---|---|---|---|---|---|---|---|---|---|---|---|---|---|---|
| caa | ctg | ctc | agt | ttc | ctc | gac | gac | gaa | atc | tcc | gac | tcg | ctc | agc | tac | 672 |
| Gln | Leu | Leu | Ser | Phe | Leu | Asp | Asp | Glu | Ile | Ser | Asp | Ser | Leu | Ser | Tyr | |
| | 210 | | | | | 215 | | | | | 220 | | | | | |

| | | | | | | | | | | | | | | | | |
|---|---|---|---|---|---|---|---|---|---|---|---|---|---|---|---|---|
| cac | ctg | cgc | aac | aac | aac | gtg | ctg | atc | cgc | cac | aac | gar | gaa | tac | gag | 720 |
| His | Leu | Arg | Asn | Asn | Asn | Val | Leu | Ile | Arg | His | Asn | Glu | Glu | Tyr | Glu | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| cgt | gtc | gaa | ggc | ctg | gac | aac | ggg | gtg | atc | ctg | cac | ctc | aag | tcc | ggc | 768 |
| Arg | Val | Glu | Gly | Leu | Asp | Asn | Gly | Val | Ile | Leu | His | Leu | Lys | Ser | Gly | |
| | | | | 245 | | | | | 250 | | | | | 255 | | |

```
aag aag atc aag gcc gac gcc ttc ctg tgg agc aac ggc cgt acc ggc     816
Lys Lys Ile Lys Ala Asp Ala Phe Leu Trp Ser Asn Gly Arg Thr Gly
        260                 265                 270 aat acc gac aag ctg ggc ctg gag aac atc ggt ctc aag gcc aat ggt     864
Asn Thr Asp Lys Leu Gly Leu Glu Asn Ile Gly Leu Lys Ala Asn Gly
    275                 280                 285 cgc gga cag atc cag gtc gac gag cac tac cgt acc gaa gtc agc aam     912
Arg Gly Gln Ile Gln Val Asp Glu His Tyr Arg Thr Glu Val Ser Xaa
290                 295                 300 att tat gcc gct ggt gac gtg atc ggc tgg ccg agc ctg gcc agc gcc     960
Ile Tyr Ala Ala Gly Asp Val Ile Gly Trp Pro Ser Leu Ala Ser Ala
305                 310                 315                 320 gcc tat gac cag ggt cgt tcg gcc gcg ggc agt atc acc gag aac gat    1008
Ala Tyr Asp Gln Gly Arg Ser Ala Ala Gly Ser Ile Thr Glu Asn Asp
            325                 330                 335 agc tgg cgt ttc gtc gac gac gtg ccg acc ggc atc tac acc att ccg    1056
Ser Trp Arg Phe Val Asp Asp Val Pro Thr Gly Ile Tyr Thr Ile Pro
                340                 345                 350 gag atc agt tcg gtc ggc aag acc gag cgc gaa ctg acc cag gcg aag    1104
Glu Ile Ser Ser Val Gly Lys Thr Glu Arg Glu Leu Thr Gln Ala Lys
            355                 360                 365 gtt ccc tac gag gtc ggc aag gcc ttc ttc aag ggc atg gcc cgg gca    1152
Val Pro Tyr Glu Val Gly Lys Ala Phe Phe Lys Gly Met Ala Arg Ala
370                 375                 380 cag atc gcc gtc gag aag gcc ggc atg ctg aag atc ctc ttt cac cgc    1200
Gln Ile Ala Val Glu Lys Ala Gly Met Leu Lys Ile Leu Phe His Arg
385                 390                 395                 400 gag acg ctg gaa atc ctc ggc gtg cac tgc ttc ggc tat cag gct tcg    1248
Glu Thr Leu Glu Ile Leu Gly Val His Cys Phe Gly Tyr Gln Ala Ser
                405                 410                 415 gaa atc gtc cat atc ggc cag gcg atc atg aac cag aag ggc gag gcg    1296
Glu Ile Val His Ile Gly Gln Ala Ile Met Asn Gln Lys Gly Glu Ala
            420                 425                 430 aat acc ctc aag tat ttc atc aac acc acc ttc aac tac ccg acc atg    1344
Asn Thr Leu Lys Tyr Phe Ile Asn Thr Thr Phe Asn Tyr Pro Thr Met
435                 440                 445 gcc gag gcc tac cgg gtg gcg gcc tac gac ggt ctc aat cgg ctt ttt    1392
Ala Glu Ala Tyr Arg Val Ala Ala Tyr Asp Gly Leu Asn Arg Leu Phe
    450                 455                 460 tga                                                                 1395
```

<210> SEQ ID NO 2
<211> LENGTH: 464
<212> TYPE: PRT
<213> ORGANISM: Azotobacter vinelandii
<220> FEATURE:
<221> NAME/KEY: misc_feature
<222> LOCATION: (5)..(5)
<223> OTHER INFORMATION: The 'Xaa' at location 5 stands for Lys, or Asn.
<220> FEATURE:
<221> NAME/KEY: misc_feature
<222> LOCATION: (304)..(304)
<223> OTHER INFORMATION: The 'Xaa' at location 304 stands for Lys, or Asn.

<400> SEQUENCE: 2

```
Met Ala Val Tyr Xaa Tyr Asp Val Val Ile Gly Thr Gly Pro Ala
 1               5                  10                  15

Gly Glu Gly Ala Ala Met Asn Ala Val Lys Ala Gly Arg Lys Val Ala
                20                  25                  30

Val Val Asp Asp Arg Pro Gln Val Gly Gly Asn Cys Thr His Leu Gly
```

-continued

```
                35                  40                  45
Thr Ile Pro Ser Lys Ala Leu Arg His Ser Val Arg Gln Ile Met Gln
 50                  55                  60

Tyr Asn Asn Pro Leu Phe Arg Gln Ile Gly Glu Pro Arg Trp Phe
 65                  70                  75                  80

Ser Phe Ala Asp Val Leu Lys Ser Ala Glu Gln Val Ile Ala Lys Gln
                 85                  90                  95

Val Ser Ser Arg Thr Gly Tyr Tyr Ala Arg Asn Arg Ile Asp Thr Phe
                100                 105                 110

Phe Gly Thr Ala Ser Phe Cys Asp Glu His Thr Ile Glu Val Val His
                115                 120                 125

Leu Asn Gly Met Val Glu Thr Leu Val Ala Lys Gln Phe Val Ile Ala
130                 135                 140

Thr Gly Ser Arg Pro Tyr Arg Pro Ala Asp Val Asp Phe Thr His Pro
145                 150                 155                 160

Arg Ile Tyr Asp Ser Asp Thr Ile Leu Ser Leu Gly His Thr Pro Arg
                165                 170                 175

Arg Leu Ile Ile Tyr Gly Ala Gly Val Ile Gly Cys Glu Tyr Ala Ser
                180                 185                 190

Ile Phe Ser Gly Leu Gly Val Leu Val Asp Leu Ile Asp Asn Arg Asp
                195                 200                 205

Gln Leu Leu Ser Phe Leu Asp Asp Glu Ile Ser Asp Ser Leu Ser Tyr
210                 215                 220

His Leu Arg Asn Asn Val Leu Ile Arg His Asn Glu Glu Tyr Glu
225                 230                 235                 240

Arg Val Glu Gly Leu Asp Asn Gly Val Ile Leu His Leu Lys Ser Gly
                245                 250                 255

Lys Lys Ile Lys Ala Asp Ala Phe Leu Trp Ser Asn Gly Arg Thr Gly
                260                 265                 270

Asn Thr Asp Lys Leu Gly Leu Glu Asn Ile Gly Leu Lys Ala Asn Gly
                275                 280                 285

Arg Gly Gln Ile Gln Val Asp Glu His Tyr Arg Thr Glu Val Ser Xaa
290                 295                 300

Ile Tyr Ala Ala Gly Asp Val Ile Gly Trp Pro Ser Leu Ala Ser Ala
305                 310                 315                 320

Ala Tyr Asp Gln Gly Arg Ser Ala Ala Gly Ser Ile Thr Glu Asn Asp
                325                 330                 335

Ser Trp Arg Phe Val Asp Asp Val Pro Thr Gly Ile Tyr Thr Ile Pro
                340                 345                 350

Glu Ile Ser Ser Val Gly Lys Thr Glu Arg Glu Leu Thr Gln Ala Lys
                355                 360                 365

Val Pro Tyr Glu Val Gly Lys Ala Phe Phe Lys Gly Met Ala Arg Ala
                370                 375                 380

Gln Ile Ala Val Glu Lys Ala Gly Met Leu Lys Ile Leu Phe His Arg
385                 390                 395                 400

Glu Thr Leu Glu Ile Leu Gly Val His Cys Phe Gly Tyr Gln Ala Ser
                405                 410                 415

Glu Ile Val His Ile Gly Gln Ala Ile Met Asn Gln Lys Gly Glu Ala
                420                 425                 430

Asn Thr Leu Lys Tyr Phe Ile Asn Thr Thr Phe Asn Tyr Pro Thr Met
                435                 440                 445

Ala Glu Ala Tyr Arg Val Ala Ala Tyr Asp Gly Leu Asn Arg Leu Phe
450                 455                 460
```

<210> SEQ ID NO 3
<211> LENGTH: 52
<212> TYPE: DNA
<213> ORGANISM: Artificial Sequence
<220> FEATURE:
<223> OTHER INFORMATION: Description of Artificial Sequence: Primer

<400> SEQUENCE: 3
attcatcgat gaattctatc ttatggtccc attctttact gcactgttta ca                52

<210> SEQ ID NO 4
<211> LENGTH: 71
<212> TYPE: DNA
<213> ORGANISM: Artificial Sequence
<220> FEATURE:
<223> OTHER INFORMATION: Description of Artificial Sequence: Primer

<400> SEQUENCE: 4
ggccactagt gatatcaaag cattctctcg ctggttaatt ttcctgtctc ttgtctatca        60
gcacttaaaa a                                                             71

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 5
ggttttctac aatctccaaa agag                                               24

<210> SEQ ID NO 6
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 6
gcgcgagatc ttctagaatg cttttttgata acaaaaat                               38

<210> SEQ ID NO 7
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 7
cgcgcagatc tccgcggaga gcctaaacga ttaacaaa                                38

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 8
gtcacacaac aaggtccta                                                     19

<210> SEQ ID NO 9
<211> LENGTH: 38
<212> TYPE: DNA

-continued

<213> ORGANISM: Artificial Sequence
<220> FEATURE:
<223> OTHER INFORMATION: Description of Artificial Sequence: Primer

<400> SEQUENCE: 9
gcgcgggatc ctctagaatg ccagtgttga aatcagac                          38

<210> SEQ ID NO 10
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 10
cgcgcggatc cccgcgggct ggaccatccc aaggttcc                          38

<210> SEQ ID NO 11
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 11
gcgcgggatc ctctagaatg gctgaagcaa gcatcgaa                          38

<210> SEQ ID NO 12
<211> LENGTH: 38
<212> TYPE: DNA
<213> ORGANISM: Artificial Sequence
<220> FEATURE:
<223> OTHER INFORMATION: Description of Artificial Sequence: Primer

<400> SEQUENCE: 12
cgcgcggatc cccgcggtta tgaagattct ctttcaaa                          38

<210> SEQ ID NO 13
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 13
tacgaagatc tgctgtatat aactacgatg tggtgg                            36

<210> SEQ ID NO 14
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 14
tagcactcga gttaaaaaag ccgattgaga cc                                32

METABOLICALLY ENGINEERED MICROBIAL CELL WITH AN ALTERED METABOLITE PRODUCTION

The present application is the national stage under 35 U.S.C. 371 of PCT/DK99/00397, filed 12 Jul. 1999.

TECHNICAL FIELD OF THE INVENTION

The invention is in the areas of microbial biotechnology, metabolic and genetic engineering. It relates to a microbial cell wherein the expression of a number of expressible enzyme activities have been either increased or decreased or eliminated in order to alter the rate of production and/or the yield of a cellular metabolite such as an intermediate product or an end product of a metabolic pathway.

At least one, preferably two or more, of said expressible enzyme activities, when expressed, mediates a reaction involved in the assimilation of a nutrient source in said cell. Assimilation of a nutrient source may involve uptake of said source into the cell and/or conversion of said source within said cell, preferably the incorporation of said source into a biosynthetic product of said cell, said incorporation being controlled by the metabolic potential and capability of said cell.

The invention described herein below relates to a manipulation of a process of assimilation of a nutrient source, preferably ammonia, and the resulting effect thereof on the capability of a microbial cell to produce one or more primary and/or secondary metabolites such as intermediate products and/or end products of one or more metabolic pathways present in said microbial cell.

BACKGROUND OF THE INVENTION

A living cell carries out a complex network of more than a thousand different reactions simultaneously, with each sequence of reactions being strictly and sensitively controlled in a number of ways so that undesirable accumulations or deficiencies of intermediates and/or end products are normally prevented from occurring. As a result of this strict and sensitive control, reactions of great mechanistic complexity and stereochemical selectivity may proceed smoothly under normal physiological conditions such as ambient pressure, moderate temperature and a pH near neutrality.

In order to appreciate the complexity and selectivity of the control of metabolic networks, it is necessary first to consider specific reaction sequences such as metabolic pathways; the relationship between each pathway and the cellular architecture; the biological importance of each metabolic pathway; and the sensitive and efficient control mechanisms regulating intracellular reaction rates. The totality of intracellular reaction rates is also known as metabolic flux.

The person skilled in the art will be aware of many microbial primary and secondary metabolites and he will have access to relevant reference collections on the subject such as the authoritative Bergeys Manual. The person skilled in the art will also have to his disposal general biochemistry textbooks comprising state of the art insights into the complex world of cellular metabolism and biochemistry.

Metabolic engineering may be perceived as a purposeful redesigning of metabolic networks generating a change in and/or a redirection of the aerobic and/or the anaerobic metabolism of a microbial cell. State of the art metabolic engineering techniques have been described by among others Cameron and Chaplen (1997) in Curr. Opin. Biotechnol., vol. 8, pages 175–180, Hahn-Hägerdal et al. (1996) in Ann. New York Acad. Sci., vol. 782, pages 286–296, Stephanopoulos (1994) in Curr. Opin. Biotechnol., vol. 5, pages 196–200. Stephanopoulos and Sinskey (1993) in Trends Biotechnol., vol. 11, pages 392–396, and Cameron and Tong (1993) in Appl. Biochem. Biotechnol., vol. 38, pages 105–140.

Some microbial cells are potentially recognisable by a single characteristic trait in the form of e.g. a metabolic end product predominantly produced under a given set of growth conditions. Accordingly, a yeast may well be initially characterised by a production of ethanol in much the same way as a lactic acid bacterial cell may be potentially identifiable by a production of lactic acid. However, the complex environment wherein microbial cell metabolites are produced evidently leads not only to the formation of a single although predominant metabolite, but rather to a complex set of metabolic intermediates and end products. Many aspects of microbial metabolism and the regulation thereof are still far from being thoroughly understood.

Cellular metabolism comprises catabolism. i.e. those processes related to a degradation of complex macromolecular substances, and anabolism, or those processes concerned primarily with the synthesis of often quite complex organic molecules. Both catabolic and anabolic pathways can be perceived to occur in several stages of complexity—one being an interconversion of polymers and complex lipids with monomeric intermediates; another an interconversion of monomeric sugars, amino acids, and lipids with relatively simple organic compounds; and yet another stage being the ultimate degradation to, or synthesis from, inorganic compounds such as $CO_2$, $H_2O$, and $NH_3$.

Catabolic and anabolic metabolism can be further divided into an aerobic and an anaerobic metabolism. i.e. metabolism occurring either in the presence or absence of oxygen. Many microorganisms are capable of growing in both the presence and absence of oxygen. Some microbial cells are strictly aerobic and depend absolutely upon an oxidative form of metabolism known as respiration, i.e. the coupling of energy generation to an oxidation of nutrients by oxygen.

The conversion of glucose to pyruvate in a cell undergoing active respiration, i.e. an oxidative breakdown and generation of energy from nutrient sources by means of a reaction with oxygen, results in the formation of a coenzyme in a reduced form known as nicotinamide adenine dinucleotide, or NADH. NADH is reoxidised through the mitochondrial electron transport chain in a process that generates additional energy and results in an ultimate transfer of electrons to oxygen.

The coenzyme nicotinamide adenine dinucleotide in its oxidised form ($NAD^+$) contains a nicotinamide ring structure that is readily reducible and thus serves as an oxidising agent. Accordingly, nicotinamide adenine dinucleotide may consist in either a reduced form, NADH, or an oxidised form, $NAD^+$. Many dehydrogenase enzymes, such as alcohol dehydrogenases, have a strong affinity for the oxidised form, $NAD^+$. After oxidation of a substrate, the reduced form of the coenzyme. NADH, leaves the enzyme and is reoxidised by available electron-acceptor systems in the cell. The $NAD^+$ so formed can now bind to another enzyme molecule and repeat the cycle. $NAD^+$ and NADH differ from most substrates in that they are continually recycled.

By contrast to the oxidative metabolism of the respiratory chain, many microorganisms either can or must grow in anaerobic environments while deriving their metabolic energy from processes that do not involve oxygen. Most of such anaerobically growing microbial organisms derive their energy from fermentations characterised by energy-yielding catabolic pathways such as glycolysis, wherein a conversion of glucose results in formation of products such as e.g. ethanol and $CO_2$.

Cellular metabolism evidently requires and generates energy, and energy-yielding metabolic pathways generate many intermediates used in numerous biosynthetic pathways. Cells mostly obtain free energy released during catabolism in the form of ATP. The chemical energy stored as ATP may be converted to other forms of energy in a process known as energy transduction.

Glycolysis is a major catabolic pathway for degradation of carbohydrates in both aerobically and anaerobically growing microbial cells. The major input to glycolysis is glucose and the pathway, comprising a total of 10 different reactions, leads to the conversion of one molecule of glucose to two molecules of pyruvate, with the concomitant generation of ATP as well as the coenzyme NADH.

The sequence of reactions between glucose and pyruvate can be considered as two distinct phases, one comprising the first five reactions and constituting an energy input phase, in which sugar phosphates are synthesised at the expense of a conversion of ATP to a less energy rich molecule in the form of ADP, and one phase comprising the last five reactions and representing an energy output phase, in which a transfer of a phosphate group to ADP leads to regeneration of ATP. The glycolytic conversion of glucose to pyruvate also involves the concomitant reduction of two moles of $NAD^+$ to its reduced equivalent NADH.

Anaerobically growing microbial cells may reduce pyruvate produced by means of glycolysis to a variety of metabolic end products such as e.g. ethanol, lactic acid, acetic acid and carbon dioxide. Ethanol production through anaerobic fermentation of a carbon source by the yeast *Saccharomyces cerevisiae* is one of the best known biotechnological processes and accounts for a world production of approximately 30 billion liters per year. The ethanol yield is lower than a maximum, theoretical yield due to a formation of a number of additional products affecting the ethanol yield, such as e.g. biomass, acetate, pyruvate, succinate and glycerol. A de novo synthesis of the first four components results in a net formation of NADH, while a synthesis of glycerol occurs under simultaneous NADH consumption. As ethanol is synthesised without a net formation or consumption of NADH, glycerol formation plays an important physiological role under anaerobic growth. Glycerol formation leads to a reoxidation of NADH to $NAD^+$ and thereby substitutes the role of oxygen as an electron acceptor.

It is known that in anaerobic cultivations of *Saccharomyces cerevisiae* CBS8066, approximately 10% of the carbon source is directed towards the formation of glycerol (Nissen et al., 1997: Verduyn et al., 1990). A redirection of this amount of carbon towards ethanol production is clearly desirable and would presuppose a reduction in the net formation of NADH in the synthesis of biomass and organic acids.

Accordingly, for the glycolytic pathway to operate anaerobically, i.e. in the absence of oxygen. NADH must be reoxidised to $NAD^+$ by means of a transfer of electrons to a suitable electron acceptor so that a steady metabolic flux can be maintained. Microbial cells growing anaerobically have different ways of transferring such electrons. A simple route used by lactic acid bacteria consists of simply using NADH to reduce pyruvate to lactate, via the enzyme lactate dehydrogenase. NADH is reoxidised in the process:

Pyruvate+NADH↔Lactate+$NAD^-$

The lactic acid fermentation. i.e. conversion of glucose to lactic acid, is important in the manufacture of cheese. Another important fermentation involves a conversion of pyruvate to acetaldehyde and $CO_2$ and a reduction of acetaldehyde to ethanol by alcohol dehydrogenase:

Acetaldehyde+NADH↔Ethanol+$NAD^+$

When carried out by yeast cells, this fermentation generates the alcohol in alcoholic beverages. Yeast cells used in baking also carry out this form of fermentation and the $CO_2$ produced by pyruvate decarboxylation causes bread to rise while the ethanol produced evaporates during baking. Among many other useful fermentations are those leading to e.g. acetic acid in the manufacture of vinegar and propionic acid in the manufacture of Swiss cheese.

Glycerol formation in cellular metabolism has at least two physiologically important roles in *Saccharomyces cerevisiae*—it is involved in NADH reoxidation and it acts as an efficient osmolyt that protects the cell against lysis under stress conditions.

Synthesis of biomass and organic acids, i.e. succinic acid, acetic acid and pyruvac acid, results in a net formation of intracellular NADH (Oura, 1977; van Dijken & Scheffers, 1986; Nissen et al. 1997). This has to be balanced by a mechanism in which NADH is reoxidised to $NAD^+$ in order to avoid depletion of the NADH pool. Under anaerobic conditions. NADH reoxidation is not possible by means of the respiratory chain, which is not functioning under such conditions. Instead. NADH is reoxidised to $NAD^+$ via formation of glycerol, since synthesis of one molecule of glycerol from glucose leads to reoxidation of one molecule of NADH.

Glycerol is also formed and accumulated inside the cell during growth under osmotic stress conditions and acts as an efficient osmolyt that protects the cell against lysis (Ansell et al., 1997; Larsson et al. (1993)). The formation of glycerol occurs via a two step reaction from dihydroxyacetone phosphate (DHAP) that is catalysed by glycerol 3-phosphate dehydrogenase and glycerol 3-phosphate phosphatase, respectively.

DHAP+NADH→Glycerol-3-Phosphate+$NAD^+$

Glycerol-3-Phosphate→Glycerol+Phosphate

In order to be able to produce any metabolic product, the microbial cell needs an input in the form of both energy and readily assimilable nutrient sources. The metabolism of a microbial cell very much determines the capability of said cell to exploit nutrient sources present in an external environment. Consequently, the metabolism of a microbial cell is dynamic and the sensitive regulation, direction and redirection of said metabolism is indicative of the responses of said cell to changing environmental conditions.

Assimilable nutrients such as various sources of nitrogen, carbon, sulphur and phosphor exist in many different forms. Some of these forms may be readily assimilated by a microbial cell while others cannot be assimilated. In the case of nitrogen, it is essential that a microbial cell is capable of assimilating this nutrient source, as nitrogen forms part of among others i) amino acids in proteins, ii) nucleotides in DNA and RNA, iii) amino sugars in complex polysaccharides, and iv) heterocyclic compounds in various coenzymes.

As described above, catabolic and anabolic pathways occur in different stages of complexity and one of said stages involves the ultimate degradation to, or synthesis from, inorganic compounds such as $CO_2$, $H_2O$, and $NH_3$. The majority if not all microbial cells are capable of assimilating ammonia and converting this source of nitrogen into organic nitrogen compounds—i.e. any organic compound comprising a C—N bond. Ammonia is thus a central metabolite and actually serves as a substrate for no less than five different enzymes that convert it into various organic nitrogen-comprising compounds. At physiological pH, the dominant ionic species is an ammonium ion, but all of said five reactions involve the unshared electron pair of $NH_3$, which is therefore generally considered the reactive species.

Accordingly, microbial cells assimilate ammonia via reactions leading to the formation of either glutamate, glutamine, asparagine, or carbamoyl phosphate. Because carbamoyl phosphate is used only in the biosynthesis of arginine, urea, and the pyrimidine nucleotides, most of the nitrogen ending up in amino acids and other nitrogen comprising organic compounds is assimilated via the two amino acids glutamate and glutamine. The enzymes responsible for ammonia assimilation in a microbial cell are briefly introduced herein below.

Glutamate dehydrogenase catalyses the reductive amination of 2-oxoglutarate:

Microbial cells growing with ammonia as their sole nitrogen source use the above reaction as a primary route for nitrogen assimilation.

Most microbial cells contain an NADPH-specific form of the glutamate dehydrogenase enzyme, as indicated above, which acts primarily in the direction of glutamate formation. Interestingly, yeast contain both a NADH-specific form and a NADPH-specific form of the enzyme, each form being appropriately regulated, with one form, NADPH, primarily involved in nitrogen assimilation and the other, NADH, functioning primarily in catabolic metabolism.

The major source of electrons for reductive biosynthesis is NADPH, nicotinamide adenine dinucleotide phosphate. $NADP^+$ and NADPH are identical to $NAD^+$ and NADH, respectively, except that the form has an additional phosphate esterified at C-2' on the adenylate moiety. $NAD^+$ and $NADP^+$ are equivalent in their thermodynamic tendency to accept electrons and they have similar standard reduction potentials. For reasons not known, nicotinamide nucleotide-linked enzymes that act in catabolic metabolism usually use the $NAD^+$/NADH coenzyme pair, whereas those acting in anabolic pathways tend to use $NADP^+$/NADPH.

Glutamate synthase is an enzyme functionally related to glutamate dehydrogenase and catalyses a reaction comparable to that catalysed by glutamate dehydrogenase. However, glutamate synthase functions primarily in glutamate biosynthesis:

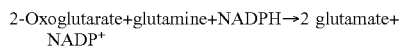

When formed by the action of glutamate dehydrogenase, glutamate can accept a second ammonia moiety to form glutamine in a reaction catalysed by the enzyme glutamine synthetase:

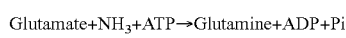

This enzyme is named a synthetase, rather than a synthase, because the reaction couples bond formation with the energy released from ATP hydrolysis. However, both enzymes are classified as ligases, but a synthase enzyme does not require ATP.

Glutamine synthetase of *E. coli* is a dodecamer, whose 12 identical subunits form two facing hexagonal arrays. The holoenzyme has a molecular weight of about 600.000. Each catalytic site is formed at an interface between polypeptide subunits within a hexamer and is made up of residues from two adjacent subunits.

Glutamine occupies a central role in the nitrogen metabolism of any microbial cell. The amide nitrogen is used in biosynthesis of several amino acids, including glutamate, tryptophan, and histidine, purine and pyrimidine nucleotides, and amino sugars. As revealed primarily based on studies in *E. coli*, several remarkable and quite extraordinary control mechanisms for glutamine synthetase mediated reactions interact with one another in very complex ways. The activity of glutamine synthetase is controlled by two distinct but mutually related mechanisms: Alosteric regulation by cumulative feedback inhibition and covalent modification of the enzyme mediated by a regulatory cascade.

Cumulative feedback inhibition involves the action of no less than eight specific feedback inhibitors. Those eight inhibitors are either metabolic end products of glutamine metabolism (tryptophan, histidine, glucosamine-6-phosphate, carbamoyl phosphate, CTP, and AMP), or they are indicators in various ways of the general status of amino acid metabolism (alanine, glycine). Quite remarkably, each 50,000-dalton subunit of glutamine synthetase contains binding sites for each of the eight inhibitors, as well as binding sites for substrates and products.

Each of the eight compounds alone gives only partial inhibition, but in combination the degree of inhibition is increased until a mixture of all eight provides a virtually complete blockage. This ensures that an accumulation of an end product of one pathway does not shut off the supply of glutamine needed for another pathway. Glutamine synthetase is also regulated by means of adenylylation. An enzyme molecule with all 12 sites adenylylated is completely inactive, whereas partial adenylylation yields a correspondingly partial inactivation.

Adenylylation and deadenylylation of glutamine synthetase involve a complex series of regulatory cascades. These regulatory cascades provide a responsive mechanism ensuring that, when the supply of activated nitrogen in the form of glutamine is sufficiently high, its further biosynthesis is shut down. In contrast, when activated nitrogen in the form of glutamine is low, 2-oxoglutarate accumulates and, provided that ATP is also abundant, stimulates the activity of glutamine synthetase by the converse mechanism.

An enzyme comparable to glutamine synthetase, asparagine synthetase, accounts for a significantly smaller amount of ammonia assimilation. Asparagine synthetase uses ammonia or glutamine in catalysing the conversion of aspartate to asparagine. The enzyme cleaves ATP differently from the way ATP is cleaved by glutamine synthetase. Asparagine synthetase also differs from glutamine synthetase in that glutamine is strongly preferred as a substrate over ammonia.

Carbamoyl phosphate synthetase is another enzyme involved in the assimilation of ammonia in microbial cells. Ammonia or glutamine may both serve as the nitrogen donor.

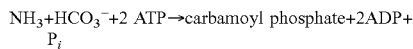

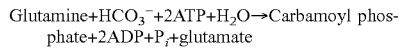

The bacterial enzyme catalyses both reactions, although glutamine is a preferred substrate. Eukaryotic microbial cells contain two forms of the enzyme. Form I is located in the mitochondria and has a preference for ammonia as substrate, whereas form II is present in the cytosol and has a strong preference for glutamine.

Several examples of metabolically engineered microorganisms are described in the patent literature. EP 0 733 712 A1 discloses a method of production of preferably an amino acid by culturing a metabolically engineered microbial cell, preferably an *Escherichia coli* cell, with a supposedly increased expression or productivity of NADPH and isolating said amino acid.

WO 96/41888 discloses a yeast cell having a modified alcohol sugar fermentation due to an altered expression of a gene encoding a NADH dependent glycerol-3-phosphate dehydrogenase activity.

EP 0 785 275 A2 discloses a yeast comprising constitutive expression of a gene encoding an enzyme activity involved in hexose transport.

EP 0 645 094 A1 discloses the use of a yeast comprising a glycolytic pathway comprising a futile cycle generated by means of a constitutive expression of genes encoding fructose-1,6-biphosphatase and phosphoenolpyruvate carboxykinase.

U.S. Pat. No. 5,545,556 discloses a yeast strain having a reduced or increased production of glycerol mediated by mutations in various gene-encoded products.

None of the above disclose a microbial cell wherein the expression of a number of expressible enzyme activities involved in nutrient assimilation are either increased or decreased or eliminated in order to alter the rate of production and/or the yield of a cellular metabolite such as an intermediate product or an end product of a metabolic pathway.

SUMMARY OF THE INVENTION

It has now surprisingly been discovered that it is possible to operably link the process of nutrient assimilation in a microbial cell such as e.g. a yeast cell with an increased production of a metabolite like e.g. ethanol. The invention is based on the unexpected and surprising finding that it is possible to operably link an energy requiring reaction such as assimilation of a nutrient source with an energy yielding reaction such as the formation of a desirable metabolic product like e.g. ethanol.

When the nutrient source is a nitrogen source such as ammonia or a nitrogen source convertible into ammonia, it is preferred to substantially reduce or eliminate the expression in a microbial cell of an enzyme, glutamate dehydrogenase, which, under normal physiological conditions, is the predominant enzyme activity involved in ammonia assimilation, and concomitantly with said reduction or elimination, increase the expression of one or both of two additional enzyme activities, glutamate synthase and glutamine synthetase, both of which are capable of assimilating ammonia into glutamate under the consumption of ATP and re-oxidation of NADH. Accordingly, overexpression of glutamate synthase and glutamine synthetase in a microbial cell, preferably a yeast cell, under anaerobic conditions, generates a reduction of intracellular ATP levels and potentially a depletion of the pool of ATP available to the cell. Under anaerobic conditions, the cell is capable of counteracting the reduction in the ATP pool by producing an increased amount of a metabolite such as e.g. ethanol via an ATP yielding reaction.

The world ethanol production reached an estimated 31.3 billion liters in 1996. Approximately 80% were produced by anaerobic fermentation of various sugar sources by *Saccharomyces cerevisiae*. Accordingly, ethanol is one of the most important biotechnological products with respect to both value and amount. Two thirds of the production is located in Brazil and in the United States with the primary objective of using ethanol as a renewable source of fuel. The demand and growth of this market is expected to give rise to a substantial growth in the ethanol production industry in the future. Hence, there are strong economic incentives to further improve the ethanol production process.

The price of the sugar source is a very important process parameter in determining the overall economy of ethanol production. Hence, it is of great interest to optimise the ethanol yield in order to ensure an efficient utilisation of the carbon source. Besides biomass and carbon dioxide, a number of by-products are formed during an anaerobic fermentation of *Saccharomyces cerevisiae* (Oura, 1977). Glycerol is the most dominant of these compounds, consuming up to 4% of the carbon source in industrial fermentations. Accordingly, it is highly desirable to eliminate formation of this compound, when it is not wanted, and redirect the metabolic flux towards ethanol production. If successfully achieved, it should in theory be possible to increase the ethanol yield by a maximum of 4%, corresponding to an increase in the world production of ethanol of 1.25 billion liters per year without any additional costs.

Although it is extremely difficult to alter or redirect a microbial metabolism, such as an anaerobic yeast metabolism, it may never the less be desirable to alter a "traditional" profile of primary and/or secondary metabolites in order to achieve a different composition or "product mix", or in order to increase or decrease or even eliminate the production of some metabolites present in said profile.

The surprising and unexpected finding described in the present invention makes it possible to i) manipulate the process of assimilation of a nutrient source such as ammonia into or in a microbial cell and ii) correlate said manipulation of said process with a provision of an altered profile of produced metabolites including e.g. ethanol and glycerol.

The correlation of assimilation of a nutrient source with primary and/or secondary metabolite production is achieved by bridging said assimilation with an altered production of a metabolite—an intermediate product or an end product of a metabolic pathway—through an extremely complex and not thoroughly understood network of metabolic reactions guiding the flux of metabolites in a microbial cell.

Accordingly, in a first aspect of the invention there is provided a microbial cell comprising i) a first expressible enzyme activity which, when expressed in said microbial cell, is controlling assimilation in said cell of a nutrient source, said expression of said first enzyme activity in said microbial cell being either novel or altered as compared to the expression of said first enzyme activity in a comparable wild-type microbial cell or a comparable isolated microbial cell, and optionally ii) a second expressible enzyme activity which, when expressed in said microbial cell, is controlling assimilation in said cell of a nutrient source, said expression of said second enzyme activity in said microbial cell being either novel or altered as compared to the expression of said second enzyme activity in a comparable wild-type microbial cell or a comparable isolated microbial cell, said second expressible enzyme activity being non-identical to said first expressible enzyme activity, and iii) a reduced expression or no expression of a third expressible enzyme activity which, when expressed in said microbial cell, is controlling assimilation in said cell of a nutrient source, said third expressible enzyme activity being non-identical to any and both of said first and second expressible enzyme activities, and further optionally iv) a fourth expressible enzyme activity which, when expressed in said microbial cell, is controlling an intracellular redox system of said cell, said expression of said fourth enzyme activity in said microbial cell being either novel or altered as compared to the expression of said fourth enzyme activity in a comparable wild-type microbial cell or a comparable isolated microbial cell, said fourth expressible enzyme activity being non-identical to each and all of said first, second and third expressible enzyme activities.

In another aspect of the invention, the microbial cell forms part of a composition further comprising a carrier. In yet another aspect there is provided a novel nucleotide sequence encoding an expressible transhydrogenase enzyme activity capable of controlling an intracellular redox system of a microbial cell. There is also provided a recombinant DNA-replicon in the form of a vector comprising said nucleotide sequence encoding said expressible transhydrogenase enzyme, and a microbial cell harbouring said nucleotide sequence or said vector. The invention also pertains to an amino acid sequence encoded by said nucleotide sequence.

In a further aspect, the invention is related to a microbial cell or a composition for use in the production of a first or a second metabolite. There is also provided a microbial cell or a composition for use in a preparation of a drinkable or an edible product. In another aspect there is provided a microbial cell or a composition for use in a production of a first or second metabolite for use in a drinkable or an edible product.

In a yet further aspect there is provided the use of a microbial cell or a composition in a production of a first or a second metabolite. The invention also pertains to the use of a microbial cell or a composition in the production of a first or second metabolite for use in a drinkable or an edible product.

In an even further aspect there is provided a method of producing a first metabolite, said method comprising the steps of i) cultivating a microbial cell or a composition comprising said cell in a suitable growth medium and under such conditions that said microbial cell is producing said first metabolite, and optionally ii) isolating said first metabolite in a suitable form, and further optionally iii) further purifying said isolated first metabolite.

In an even further aspect there is provided a method of constructing a microbial cell according to the invention, said method comprising the steps of i) operably linking a nucleotide sequence encoding said first expressible enzyme activity with an expression signal not natively associated with said nucleotide sequence, and/or ii) operably linking a nucleotide sequence encoding said second expressible enzyme activity with an expression signal not natively associated with said nucleotide sequence, and iii) eliminating said third expressible enzyme activity from said microbial cell or optionally operably linking a nucleotide sequence encoding said third expressible enzyme activity with an expression signal not natively associated with said nucleotide sequence, said expression signal generating a reduced expression of said nucleotide sequence, and iv) introducing said operably linked nucleotide sequences obtained under i) and iii), and optionally the nucleotide sequence obtained under ii), into said microbial cell, or v) introducing said operably linked nucleotide sequence obtained under i), and optionally the nucleotide sequence obtained under ii), into said microbial cell obtained under iii) wherein said third expressible enzyme activity has been eliminated.

Preferred embodiments of the above-mentioned aspects of the invention are described herein below.

DETAILED DESCRIPTION OF THE INVENTION

Attempts have been made to increase ethanol formation in yeast by elimination of glycerol synthesis through deletions of GPD1 and GPD2, encoding the two existing isoenzymes of glycerol 3-phosphate dehydrogenase (Björkqvist et al. 1997). The double deletion mutant is unable to grow under anaerobic conditions due to accumulation of intracellular NADH. NADH is accumulated since no alternative pathways to reoxidise NADH under these growth conditions exist in S. cerevisiae. Elimination of the capability of generating glycerol results in a strain with a high sensitivity to osmotic stress. Osmotic stress is caused by growth of a cell in an industrial growth medium high in concentrations of various carbon sources and salts. Deletion of one of the genes results neither in a significant reduction in glycerol formation nor in an increased ethanol formation (Liden et al., 1997: Nissen et al., 1998a,b).

Consequently, metabolic engineering of the synthesis of glycerol has so far not proved successful and no significant increase in ethanol production in a metabolically engineered S. cerevisiae strain has been reported.

It has now surprisingly been found that it is possible to implement a strategy comprising a reduction of a surplus of NADH formed by catabolic metabolism concomitantly with an increased consumption of ATP in the synthesis of biomass.

Ammonia is often used as a nitrogen source in industrial fermentations of S. cerevisiae. Following transport across the membrane into the cytoplasm, ammonia or the ammonium ion is converted into glutamate by assimilation with 2-oxoglutarate. In wild-type cells this reaction is catalysed by an NADPH-dependent glutamate dehydrogenase encoded by GDH1 (Moye et al., 1985):

$$2\text{-Oxoglutarate} + NH_4^+ + NADPH \rightarrow Glutamate + NADP^+$$

Two other glutamate dehydrogenases, encoded by GDH2 and GDH3, are also present in S. cerevisiae. Gdh2p normally catalyses the opposite reaction as that of Gdh1p under formation of NADH (Miller and Magasanik, 1990; Miller and Magasanik, 1991; Coschigano et al., 1991: Courchesne and Magasanik, 1988). This reaction occurs when nitrogen sources other than ammonium and glutamine are used. The reaction may also play a role in ammination reactions during synthesis of various amino acids.

The activity of Gdh2p is 70 times lower than the activity of Gdh1p, when ammonium is used as nitrogen source (Nissen et al. 1997). It has been demonstrated, as described herein below and in Example 1, that formation of glycerol can be reduced by deleting GDH1 and overexpressing GDH2. These manipulations result in a genetically modified yeast strain synthesising glutamate under consumption of NADH rather than NADPH (Nissen et al., 1998a). However, this reduction in glycerol formation did not result in an overall increase in the ethanol yield. The function of NADPH-dependent Gdh3p is unknown. No activity of a NADPH-dependent glutamate dehydrogenase can be measured in cells with a deletion in GDH1 when ammonium is used as nitrogen source, suggestion an involvement of this enzyme primarily when other nitrogen sources are used (Nissen et al. 1998a; Avendaňo et al., 1997).

Interestingly, there exist another system capable of synthesising glutamate in *S. cerevisiae*. This system consists of two coupled reactions, catalysed by glutamate synthase, encoded by GLT1, and glutamine synthetase, encoded by GLN1 (Cogoni et al. 1995, Miller and Magasanik, 1983). The reactions mediated by said enzymes are briefly illustrated below.

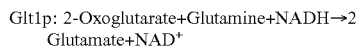

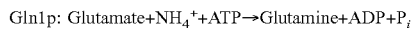

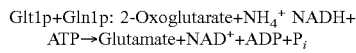

In wild-type cells, the activity of Glt1p is 80 times lower than the activity of Gdh1p. Hence, the system can be expected to have a very limited effect on the assimilation of ammonium in a yeast cell.

If GDH1 is deleted from a yeast cell, the cell becomes unable to assimilate ammonium by the means of NADPH-dependent glutamate dehydrogenase activity. This leads to a decrease in the maximum specific growth rate to half of that observed for a wild-type yeast cell (Nissen et al. 1998a), this is probably due to a limitation in glutamate synthesis, since other enzymes potentially involved in this process are expressed at very low levels, as described herein above.

A double mutant in GDH1 and GLT1 is unable to grow on ammonium as nitrogen source, indicating that glutamate synthase potentially could have a role as a backup system in the synthesis of glutamate (Miller and Magasanik, 1990). Thus, it was hypothesised that by overexpressing GLT1 and GLN1 in a Δgdh1 mutant, it should be possible to alleviate and/or eliminate the limiting effect of glutamate synthesis on $\mu_{max}$ and obtain a *S. cerevisiae* strain with a reduced surplus formation of NADH and an increased consumption of ATP in biomass synthesis.

It has been demonstrated that deletion of GDH1, encoding the NADPH-dependent glutamate dehydrogenase 1, in a wild-type strain of *S. cerevisiae* resulted in an increase in ethanol formation and a decrease in glycerol formation (Nissen et al. 1998a,b). Unfortunately, the ethanol productivity was significantly affected by the deletion since the maximum specific growth rate of the Δgdh1 mutant was approximately half of that of the wild-type strain.

The present invention has demonstrated for the first time that overexpression of GLN1, encoding glutamine synthetase, and GLT1, encoding glutamate synthase, in a Δgdh1 mutant results in a significant increase in the maximum specific growth rate, as compared to the Δgdh1 mutant, as well as a substantially increased yield of ethanol.

Consequently, a novel pathway for glutamate synthesis has been shown to substitute the role of an NADPH-dependent glutamate dehydrogenase in the assimilation of ammonium and 2-oxoglutarate to glutamate.

The maximum specific growth rate of a strain according to the invention, TN19, was 90% of the maximum specific growth rate of the wild-type and this clearly limits the increase in the specific ethanol productivity that was obtained. This problem can most likely be solved by increasing the specific activities of Gln1p and Glt1p even more. In one embodiment of the invention, a five-fold increase in the specific activity of glutamate synthase was obtained by insertion of the PGK promoter into chromosome IV in front of the structural gene of the enzyme. This level of activity can be increased significantly by e.g. inserting more copies of the gene into the chromosome by means of e.g. amplification. It is also possible to subject the expression system in question to a detailed genetic and/or biochemical analysis in order to find ways of increasing the expression.

In an earlier study, it was demonstrated that overexpression of GDH2, encoding the NADH-dependent glutamate dehydrogenase, in a Δgdh1 mutant led to an increase in the maximum specific growth rate from 0.22 $h^{-1}$ to 0.39 $h^{-1}$ (Nissen et al. 1998a). The specific activity of Gdh2p in this strain was 0.625 units per mg TCP, ten-fold higher than in the wild-type, which illustrates that the activity of Glt1p and Gln1p should be increased further in order to achieve the same maximum specific growth rate as the wild-type.

The limited increase in the fermentation time of TN19 compared to TN1 might not be a serious problem, as it is the substrate cost that is a primary factor determining the overall economy of ethanol production. This means that the observed increase in the ethanol yield of TN19, combined with the relative small reduction of the maximum specific growth rate, represents a breakthrough in and a valuable contribution to an optimisation of microbial ethanol production.

Furthermore, the results obtained in this study showed that even though it is very difficult to perform a metabolic engineering process, the proposed strategy of increasing the ethanol yield in *S. cerevisiae* by metabolic engineering of pathways involved in nutrient assimilation and biomass synthesis is a major success.

Accordingly, it has been demonstrated that a mere reduction of glycerol formation via metabolic engineering of NADH- and NADPH-consuming reactions does not necessarily result in an increased flux towards ethanol, and said reduced glycerol formation must accordingly, as convincingly demonstrated herein by the provision of impressive results representing a breakthrough in microbial ethanol production, be combined with an increased consumption of ATP in biomass formation in order to redirect carbon flux from glycerol towards an increased production of ethanol.

The microbial cell according to the invention comprises an altered composition of expressible enzyme activities and/or an altered expression thereof. In principle, any microbial cell capable of i) assimilating a nutrient source, ii) metabolising said source, and iii) producing a biosynthetic product in the form of e.g. one or more primary and/or secondary metabolites, forms part of the invention. The expressible enzyme activities such as a first and/or second expressible enzyme activity are preferably operably linked to an expression signal not natively associated with said activities.

In a preferred embodiment there is provided a microbial cell comprising
  i) an increased expression of said first expressible enzyme activity controlling assimilation in said cell of a nutrient source, said first expressible enzyme activity being operably linked to an expression signal not natively associated with said first enzyme activity, and optionally
  ii) an increased expression of said second expressible enzyme controlling assimilation in said cell of a nutrient source, said second expressible enzyme activity being operably linked to an expression signal not natively associated with said second enzyme activity, and
  iii) a reduced expression or no expression of said third expressible enzyme activity which, when expressed in said microbial cell, is controlling assimilation in said cell of a nutrient source, said third expressible enzyme activity being optionally operably linked to an expression signal not natively associated with said third enzyme activity, and further optionally
  iv) a fourth expressible enzyme controlling an intracellular redox system of said cell, said fourth expressible enzyme activity being operably linked to an expression signal not natively associated with said fourth enzyme activity.

In another preferred embodiment, the microbial cell of the invention comprises a further expressible enzyme activity, said further expressible enzyme activity, when expressed, mediates an energy yielding first reaction resulting in a production of a first metabolite said first reaction being operably linked to an energy requiring second reaction resulting in assimilation of a nutrient source. The microbial cell is preferably one wherein said energy requiring second reaction resulting in assimilation of a nutrient source is controlled at least by said first and/or second expressible enzyme activity.

In yet another embodiment there is provided a microbial cell comprising a further expressible enzyme activity, said further expressible enzyme activity, when expressed, mediates an energy yielding first reaction resulting in a production of a first metabolite, said further expressible enzyme activity, when expressed at an increased level, results in an increased production of said first metabolite, said increased expression of said further expressible enzyme activity and/or said increased production of said first metabolite is operably linked to an increased expression of said first and/or second expressible enzyme activity.

The expression of said further expressible enzyme activity preferably results in the production of an intermediate or an end product of a metabolic pathway such as metabolites like e.g. lactic acid, acetic acid, propionic acid or ethanol, or a combination thereof. The energy yielding first reaction may accordingly be mediated by a dehydrogenase enzyme such as e.g. an organic acid dehydrogenase such as a lactate dehydrogenase, or by an alcohol dehydrogenase mediating the formation of ethanol from acetaldehyde.

A primary metabolite is any metabolite forming part of a major metabolic pathway shared by a number of comparable microorganisms such as microorganisms within the same species or subspecies. Major metabolic pathways are understood to comprise glycolysis, citric acid cycle, gluconeogenesis, pentose phosphate pathway, urea cycle, and the like.

A secondary metabolite is any organic compound forming part of minor pathways that are "branched off" the above-mentioned major metabolic pathways. The secondary metabolites may well be produced by some members within a species and not by others. An introduction to secondary metabolites is provided by Herbert (1981) in "The Biosynthesis of Secondary Metabolites" (Chapman and Hall, London, England).

The microbial cell in question may thus be a microbial eukaryote or a microbial prokaryote. Among microbial eukaryotes are many yeast and fungal cells preferred, such as yeast cells of the species *Saccharomyces, Schizosaccharomyces* and *Pichia*, such as e.g. *Saccharomyces cerevisiae, Schizosaccharomyces pombe, Pichia pastoris* and the like, as well as algae such as e.g. *Chlamydomonas reinhardi*, slime moulds such as e.g. *Diclyostelium discoideum* and filamentous fungi. Preferred filamentous fungi are species of *Neurospora* and *Aspergillus* such as e.g. *Neurospora crassa, Aspergillus nidulans, Aspergillus niger, Aspergillus oryzae* and *Penicillium chrysogenum*. Particularly preferred are also many industrially relevant yeast cells, slime moulds and filamentous fungi providing a production of products such as e.g. antibiotics, steroids, pigments, enzymes, organic alcohols and acids, amino acids, polysaccharides and the like.

Among preferred microbial prokaryotes are bacterial cells such as Gram-positive species such as e.g. *Bacillus subtilis, Bacillus thuringensis, Bacillus licheniformis, Bacillus amyloliquefaciens, Bacillus cereus, Bacillus lentus* and *Bacilus stearothermophilus*, species of *Corynebacterium* and *Propionibacterium* as well as Gram-negative species such as *Escherichia coli*. Particularly preferred are also lactic acid bacterial species such as e.g. *Lactococcus lactis, Lactococcus lactis* subsp. *lactis, Lactococcus lactis* subsp *cremoris, Lactococcus lactis* subsp. *diacetylactis, Leuconostoc* species, *Lactobacillus* species, *Pediococcus* species and similar industrially relevant species like e.g. *Bifidobacterium*.

The nutrient source is any nutrient source capable of sustaining microbial growth by e.g. being assimilated into a biosynthetic product that can be utilised by a microbial cell or be converted i.e. metabolised into a further biosynthetic product, said utilisation and/or metabolism involving one or more energy yielding metabolic reactions. Consequently, it will be understood that any nutrient source that is assimilable and metabolisable by a microbial cell forms part of the invetnion. The step of assimilation shall be understood to comprise both uptake of said source into said cell as well as conversion of said source into a biosynthetic product—an intermediate metabolite—within said cell. In a more narrow scope of the understanding of the term, assimilation shall be meant preferably to comprise the assimilation that takes place within the cell without necessarily being limited to this step of the assimilation process.

In a preferred embodiment of the invention there is provided means for an increased efficiency of an uptake of a nutrient source into a microbial cell and/or an increased efficiency of assimilation within said cell. The term efficiency shall be understood to comprise, that both uptake and/or intracellular conversion takes place at a faster rate, i.e. increased amounts of nutrients are taken up and/or metabolised per unit time, or per unit cell time per unit cell mass, in said cell according to the invention, as compared to a comparable wild-type cell or a comparable isolated cell. The person skilled in the art will be aware as to how a trans-membrane transport and an internal turnover of an assimilated nutrient source may be monitored.

The nutrient source is preferably a nitrogen source, a carbon source, a sulphur source, or a phosphor source, more preferably a nitrogen source. Preferred assimilable nitrogen sources comprise ammonia, ammonium ions, nitrite ions, and nitrate ions. The assimilable nitrogen source according to the invention is more preferably ammonia and ammonium ions and most preferably ammonia. It will be understood that the invention pertains to all nitrogen containing nutrient sources capable of being converted into ammonia by oxidation including biological oxidation or by reduction including biological reduction. The skilled person will be aware of the fact that biological oxidations and/or reductions may well occur in the absence of oxygen as a final electron acceptor.

The microbial cell according to the invention comprises a first expressible enzyme activity which, when expressed in said microbial cell, is controlling assimilation in said cell of a nutrient source, preferably a nitrogen source such as e.g. ammonia, said expression of said first enzyme activity in said microbial cell being either novel or altered as compared to the expression of said first enzyme activity in a comparable wild-type microbial cell or a comparable isolated microbial cell.

In a preferred embodiment, the microbial cell comprises a first and a second expressible enzyme activity which, when expressed in said microbial cell, are controlling assimilation in said cell of a nutrient source, preferably a nitrogen source such as e.g. ammonia, said expression of said first and second enzyme activities in said microbial cell is either novel to said cell or altered as compared to the expression of said first and second enzyme activities in a comparable wild-type microbial cell or a comparable isolated microbial cell, said first and second expressible enzyme activities being non-identical to one another.

An expressible enzyme activity mediated facilitation of assimilation of a nutrient source is understood to comprise the capability of said microorganism to carry out a metabolic reaction leading to assimilation in the form of uptake and/or intracellular conversion of said nutrient source. An intracellular conversion is understood to comprise the synthesis of a biosynthetic product by fusion of said nutrient source—in the uptakable form such as a directly assimilable form or in a subsequently processed form—with a metabolite being synthesised by said cell, said fusion generating a metabolisable biosynthetic product. It is particularly preferred that the expressible enzyme activity according to the invention, when expressed, is mediating a biosynthetic reaction.

An altered expression of said first and/or second expressible enzyme activity in the microbial cell according to the invention shall be understood to comprise any expression that differs with respect to the rate of product formation or with respect to the amount of product formed as compared to a comparable microbial cell. Accordingly, if a wild-type microbial cell is subjected to the metabolic engineering manipulations according to the invention, the skilled person will compare the expression of said first and/or second expressible enzyme activities provided in the metabolically engineered cell with the expression of the same activities in the wild-type microbial cell.

Generally, the person skilled in the art will preferably analyse—and compare with one another—similar or near identical microbial cells such as identical cells with and without an expressible enzyme activity according to the invention. This is standard laboratory practise and the person skilled in the art will know how to conduct such an analysis so that it may form a basis for a direct comparison of e.g. an expressed enzyme activity or an expressed coenzyme or an expressed redox system within the meaning of those terms as set out herein below.

Preferably, the person skilled in the art will want to compare microbial cells to cells of at least the same species and more preferably to compare said cells to cells of at least the same subspecies.

Accordingly, if an isolated microbial cell such as e.g. an industrial strain or a strain in a culture collection is subjected to the metabolic engineering manipulations according to the invention, the skilled person will compare the expression of said first and/or second expressible enzyme activities provided in the metabolically engineered cell with the expression of the same activities in the industrial strain or the microbial cell of the culture collection.

The skilled artisan will know how to culture comparable strains such as strains of the same species or subspecies under identical or substantially similar conditions so as to provide a basis for performing the comparison between the relevant enzyme activities. The person skilled in the art will also know how to perform an enzymatic assay for use in said comparison and being indicative of the formation of a biosynthetic product resulting from the action of said first and/or second expressible activities, when expressed, and he will be aware of the potential of transcriptional and/or translational fusions in monitoring expression of said expressible enzyme activities under comparable conditions. The skilled person will also be able to perform immunoassays including quantitative immunoprecipitations. An analysis of gene expression is available in e.g. Old and Primrose (1985): Principles of Gene Manipulation— An introduction to genetic engineering (Third edition). Blackwell Scientific Publications, Oxford, England.

The altered expression of said first and/or second expressible enzyme activity in the microbial cell according to the invention shall preferably be understood to comprise an increased expression as compared to the expression in a comparable microbial cell. Accordingly, any of said first or second expressible enzyme activity, when expressed, is, independently of the other, increased by a factor of at least 1.02, such as a factor of at least 1.04, for example 1.06, such as 1.08, for example 11.10, such as at least 1.12, for example 1.14, such as 1.16, for example 1.18, such as 1.2, for example 1.25, such as 1.3, for example 1.4, such as 1.5, for example 1.6, such as 1.7, for example 1.8, such as 1.9, for example 2.0, such as 2.25, for example 2.5, such as 3, for example 3.5, such as a factor of at least 4, for example 4.5, such as 5, for example 6, such as 7, for example 8, such as 9, for example 10, such as 15, for example 20, such as 25, for example 30, such as 35, for example 40, such as 50, for example 60, such as 80, for example at least 100, such as 150, for example 200, such as 250, for example 300, such as 350, for example 400, such as 500, for example 600, such as 800, for example at least 1000, such as 1500, for example 2000, such as 2500, for example 3000, such as 3500, for example 4000, such as at least 5000, for example 6000, such as 8000, for example at least 10000, such as 15000, for example 20000, such as at least 25000, for example 30000, such as 35000, for example 40000, such as a factor of at least 50000.

However, an altered expression shall not be limited to an increased expression. A reduced expression of said expressible activities should also be understood to be comprised by the term altered expression.

A biosynthetic reaction mediated by said first or second expressible enzyme activity, when expressed, is preferably a reaction capable of being carried out by action of a metabolite synthase enzyme, more preferably by an allosteric metabolite synthase enzyme, and even more preferably is said reaction carried out by an expressible enzyme activity which, when expressed, is exhibited by a glutamate synthase.

In a particularly preferred embodiment of the invention, said glutamate synthase activity is that of GLT1 of *Saccha-*

*romyces cerevisiae* such as e.g. that of TN17 deposited under DSM Accession Number 12275 or an activity functionally equivalent therewith. A functionally equivalent activity is any activity capable of carrying out the same reaction with the provision of a similar outcome as that resulting from the reaction being carried out by the above-mentioned GLT1 encoded polypeptide of *Saccharomyces cerevisiae*. When the expressible enzyme activity is an activity exhibited by a glutamate synthase, the microbial cell is preferably a yeast cell and more preferably a *Saccharomyces cerevisiae* cell.

Another biosynthetic reaction mediated by said first or second expressible enzyme activity, when expressed, is preferably a reaction capable of being carried out by action of a metabolite synthetase enzyme, and more preferably is said reaction carried out by an expressible enzyme activity which, when expressed, is exhibited by a glutamine synthetase.

It is evident that, as described herein above, an extremely complex and intricate enzyme being regulated as strictly and sensitively as glutamine synthetase does not form an obvious candidate for redirecting the metabolic flux of biosynthetic reactions related to the assimilation of ammonia in a microbial cell.

In a particularly preferred embodiment of the invention, said glutamine synthetase activity is that encoded by GLN1 of *Saccharomyces cerevisiae* such as e.g. that of TN15 deposited under DSM Accession Number 12274 or an activity functionally equivalent therewith. A functionally equivalent activity is any activity capable of carrying out the same reaction with the provision of a similar outcome as that resulting from the reaction being carried out by the above-mentioned GLN1 encoded activity of *Saccharomyces cerevisiae*. When the expressible activity is an activity exhibited by a glutamate synthase, the microbial cell is preferably a yeast cell and more preferably a *Saccharomyces cerevisiae* cell.

Accordingly, in a particularly preferred embodiment there is provided a microbial cell, preferably a yeast cell, wherein said first expressible enzyme activity is a metabolite synthase activity, more preferably an allosteric metabolite synthase activity, and even more preferably a glutamate synthase activity and wherein said second expressible enzyme activity is a metabolite synthetase activity, preferably a glutamine synthetase activity.

In another preferred embodiment is said first and/or second expressible enzyme activity a ligase activity or an NADH-dependent glutamate dehydrogenase activity or a NADPH-dependent glutamate dehydrogenase activity.

The microbial cell according to the invention may—in addition to an expressible first and/or second enzyme activity—also comprise a third expressible enzyme activity, said activity, when expressed in said microbial cell, preferably a yeast cell, is controlling assimilation in said cell of a nutrient source, said expression of said third enzyme activity in said microbial cell, preferably a yeast cell, being either novel or altered as compared to the expression of said third enzyme activity in a comparable wild-type microbial cell or a comparable isolated microbial cell, said third expressible enzyme activity being non-identical to any and both of said first and second expressible enzyme activities.

There is also provided an embodiment of the invention wherein said third expressible enzyme activity has been deleted from and no longer is present in said cell. It is particularly preferred to delete said third expressible enzyme activity when the microbial cell is a yeast cell, but the activity may also be deleted from any other eukaryotic microbial cell or from a prokaryotic microbial cell.

Reference is made to the above-mentioned comments and arguments concerning a definition of terms such as assimilation, nutrient source, altered expression and comparable microbial cell. The interpretations indicated herein above also apply with respect to said expressible third enzyme activity.

Accordingly, in one preferred embodiment according to the invention, the third expressible enzyme activity is preferably a metabolite dehydrogenase activity, and more preferably a glutamate dehydrogenase activity which is either present in said microbial cell and preferably in a reduced amount, more preferably in a substantially reduced amount, or eliminated from said cell by means of e.g. deletion of a nucleotide sequence encoding said activity or by effectively repressing the expression of said expressible third enzyme activity.

Consequently, an altered expression in said microbial cell according to the invention of said third expressible enzyme activity, preferably a glutamate dehydrogenase activity and even more preferably a NADPH dependent glutamate dehydrogenase activity, shall be understood to comprise a decreased expression as compared to the expression of said activity in a comparable microbial cell. Accordingly, the expression of said third expressible enzyme activity, when expressed, is decreased by at least 1 percent, such as decreased by at least 2 percent, for example 4 percent, such as 6 percent, for example at least 8 percent, for example at least 10 percent, such as 12 percent, for example 14 percent, such as 16 percent, such as at least 18 percent, for example at least 20 percent, such as 22 percent, for example 24 percent, such as 26 percent, such as at least 28 percent, for example at least 30 percent, such as 32 percent, for example 34 percent, such as 36 percent, for example 38 percent, such as at least 40 percent, for example 42 percent, such as 44 percent, for example 46 percent, such as 48 percent, such as at least 50 percent, for example 52 percent, such as 54 percent, for example 56 percent, such as 58 percent, such as at least 60 percent, for example 62 percent, such as 64 percent, for example 66 percent, such as 68 percent, such as at least 70 percent, for example 72 percent, such as 74 percent, for example 76 percent, such as 78 percent, such as at least 80 percent, for example 82 percent, such as 82 percent, for example 84 percent, such as 86 percent, such as at least 88 percent, for example 90 percent, such as 92 percent, for example 94 percent, such as 96 percent, for example at least 98 percent, such as 99 percent, for example 99.2 percent, such as at least 99.4 percent, for example 99.6 percent, such as 99.8 percent, for example 99.9 percent, such as 99.92 percent, for example 99.94 percent, such as 99.96 percent, for example 99.98 percent, such as 99.99 percent, for example decreased to such an extend that said expression is unassayable using standard state of the art assays and/or said expression is effectively repressed and/or substantially eliminated.

However, an altered expression shall not be limited to a decreased expression. An increased expression of said third expressible enzyme activity shall also be understood to be comprised by the term altered expression.

In a particularly preferred embodiment of the invention said glutamate dehydrogenase activity is that of a GDH1 encoded polypeptide of *Saccharomyces cerevisiae* such as e.g. TN1, or an activity functionally equivalent therewith. A functionally equivalent activity is any activity capable of carrying out the same reaction with the provision of a similar outcome as that resulting from the reaction being carried out by the above-mentioned GDH1 encoded polypeptide of *Saccharomyces cerevisiae*. When the glutamate dehydrogenase activity is encoded by GDH1 of *Saccharomyces cerevisiae*, the microbial cell is preferably a yeast cell and more preferably a *Saccharomyces cerevisiae* cell.

Microbial cells pertaining to the invention have been deposited with the DSM under Accession Numbers 12267, 12268, 12274, 12275, 12276 and 12277 as *Saccharomyces cerevisiae* strains TN4, TN9, TN15, TN17, TN19, and TN22, respectively.

Accordingly, said third expressible enzyme activity, preferably in the form of a glutamate dehydrogenase activity and when expressed, is either expressed at a substantially reduced level, not expressed at all in said cell due to e.g. an efficient repression of expression, or the activity has been eliminated altogether from said cell. It is particularly preferred that a DNA sequence encoding said third expressible enzyme activity, preferably a glutamate dehydrogenase activity, and/or expression signals directing expression thereof, has been partly or wholly deleted from a chromosomal replicon and/or an extrachromosomal replicon harboured by said microbial cell.

In a particularly preferred embodiment of the invention, there is provided a microbial cell wherein the expression of said first and/or second expressible enzyme activity is increased, preferably substantially increased, whereas the expression of said third expressible enzyme activity is decreased, preferably substantially decreased. Reference is made to levels of such increased and decreased expression as indicated herein above.

A microbial cell according to the invention, such as a microbial cell, preferably a yeast cell, wherein the expression of said first and/or second expressible enzyme activity is increased, preferably substantially increased, whereas the expression of said third expressible enzyme activity is decreased, preferably substantially decreased, may in one embodiment produce a first metabolite, such as e.g. ethanol, said production of said first metabolite, preferably ethanol, is increased as compared to an expression of said metabolite in a comparable wild-type or isolated cell, said increase is increased by a factor of at least 1.005, for example 1.010, such as 1.015, for example 1.020, such as a factor of at least 1.025, for example a factor of at least 1.030, such as 1.035, for example 1.040, such as 1.045, for example 1.050, such as 1.055, for example 1.060, such as at least 1.065, for example a factor of at least 1.070, such as 1.075, for example 1.080, such as 1.085, for example a factor of at least 1.090, such as 1.095, for example 1.100, such as 1.105, for example 1.110, such as 1.115, for example 1.120, such as at least 1.125, for example a factor of at least 1.130, such as 1.135, for example 1.140, for example 1.145, such as 1.150, for example 1.155, such as at least 1.160, for example a factor of at least 1.165, such as a factor of at least 1.170, for example a factor of at least 1.175, such as 1.180, for example 1.185, such as 1.190, for example 1.195, such as a factor of at least 1.200, for example 1.21, such as 1.22, for example 1.23, such as 1.24, for example 1.25, such as 1.26, for example 1.27, such as 1.28, for example 1.29, such as a factor of at least 1.30, for example 1.35, such as 1.40, for example 1.45, such as 1.50, for example 1.55, such as 1.60, for example 1.65, such as 1.70, for example 1.75, such as 1.80, for example 1.85, such as 1.90, for example 1.95, such as a factor of at least 2.0, for example 2.2, such as 2.4, for example 2.6, such as 2.8, for example 3.0, such as 3.2, for example 3.4, such as 3.6, for example 3.8, such as at least 4.0, for example 4.2, such as 4.4, for example 4.6, such as 4.8, for example at least 5.0, such as 5.2, for example 5.4, such as 5.6, for example 5.8, such as at least 6.0, for example 6.2, such as 6.4, for example 6.6, such as 6.8, for example at least 7.0, for example 7.2, such as 7.4, for example 7.6, such as 7.8, for example 8.0, such as 8.2, for example 8.4, such as 8.6, for example 8.8, such as at least 9.0, for example 9.2, such as 9.4, for example 9.6, such as 9.8, for example a factor of at least 10.0.

Said microbial cell, most preferably yeast, having an increased production of a first metabolite has, in another preferred embodiment, a decreased production of a second metabolite, preferably glycerol. Said decreased production of said second metabolite, preferably glycerol, is decreased by at least 0.5 percent, for example at least 1 percent, such as at least 2 percent, for example 4 percent, such as 6 percent, such as at least 8 percent, for example at least 10 percent, such as 12 percent, for example 14 percent, such as 16 percent, such as at least 18 percent, for example at least 20 percent, such as 22 percent, for example 24 percent, such as 26 percent, such as at least 28 percent, for example at least 30 percent, such as 32 percent, for example 34 percent, such as 36 percent, for example 38 percent, such as at least 40 percent, for example 42 percent, such as 44 percent, for example 46 percent, such as 48 percent, such as at least 50 percent, for example 52 percent, such as 54 percent, for example 56 percent, such as 58 percent, such as at least 60 percent, for example 62 percent, such as 64 percent, for example 66 percent, such as 68 percent, such as at least 70 percent, for example 72 percent, such as 74 percent, for example 76 percent, such as 78 percent, such as at least 80 percent, for example 82 percent, such as 82 percent, for example 84 percent, such as 86 percent, such as at least 88 percent, for example 90 percent, such as 92 percent, for example 94 percent, such as 96 percent, for example at least 98 percent, such as 99 percent, for example 99.2 percent, such as at least 99.4 percent, for example 99.6 percent, such as 99.8 percent, for example 99.9 percent, such as 99.92 percent, for example 99.94 percent, such as 99.96 percent, for example 99.98 percent., such as 99.99 percent, for example an expression level being decreased to such an extend that said expression of said third activity is unassayable using standard state of the art assays and/or said expression is effectively repressed and/or substantially eliminated.

In another particularly preferred embodiment, the maximum specific growth rate of said cell according to the invention is substantially unaltered as compared to a comparable wild-type microbial cell or to a comparable isolated microbial cell. However, a microbial cell characterised by a decrease in the maximum specific growth rate is also preferred according to the invention, such as a microbial cell, preferably a yeast cell, having a maximum specific growth rate that is decreased by less than 1 percent, such as 1.5 percent, for example 2.0 percent, such as by less than 2.5 percent, for example 3.0 percent, such as 3.5 percent, for example by less than 4.0 percent, such as 4.5 percent, for example 5.0 percent, such as by less than 5.5 percent, for example 6.0 percent, such as 6.5 percent, for example by less than 7.0 percent, such as 7.5 percent, for example 8.0 percent, such as by less than 8.5 percent, for example 9.0 percent, such as 9.5 percent, for example by less than 10.0 percent, such as 12 percent, for example 14 percent, such as by less than 16 percent, for example 18 percent, such as 20 percent, for example by less than 25 percent.

In a further embodiment, the microbial cell comprising said first and/or second expressible enzyme activity and optionally said third expressible enzyme activity, if said activity has not been eliminated from said cell by removal, deletion or otherwise, may further optionally comprise a fourth expressible enzyme activity. Accordingly, there is provided, in one embodiment of the invention, a microbial cell according to the invention further comprising said fourth expressible enzyme activity whereas, in another embodiment, said fourth expressible activity is not present in said microbial cell.

Said fourth expressible enzyme activity, when expressed, is controlling an intracellular redox system of said cell, said expression of said fourth enzyme activity in said microbial cell being either novel or altered as compared to the expression of said fourth enzyme activity in a comparable wild-type microbial cell or a comparable isolated microbial cell, said fourth expressible enzyme activity being non-identical to each and all of said first, second and third expressible enzyme activities.

In a particularly preferred embodiment of the invention, said fourth expressible enzyme activity is encoded by a nucleotide sequence designated SEQ ID NO:1 as illustrated herein below. Said nucleotide sequence was cloned into a multi copy plasmid, Yep24-pPGK. This plasmid was constructed from Yep24 and contains the promoter and terminator of PGK and was provided by Mikael Anderlund (Walfridsson et al., 1997). CTH was ligated into YEp24 behind the strong constitutive promoter of PGK resulting in plasmid Yep24-pPGK-CTH. This plasmid was transferred into strain TN2 resulting in strain TN4.

The terms altered expression and comparable microbial cell as introduced herein above do also apply to said fourth expressible enzyme activity. The term intracellular redox system shall be understood to comprise any redox system comprising a coenzyme that is present in corresponding oxidised and reduced forms. Preferred intracellular redox systems are coenzymes in corresponding oxidised/reduced forms such as e.g. $NAD^+/NADH$ and $NADP^+/NADPH$.

The term maintenance of an intracellular redox system shall be understood to comprise the action exerted by any expressible enzymatic activity which, when expressed, is providing an input to such a system by e.g. acting in a pathway leading to the synthesis of one or more components of said system or by acting in a recycling or indeed any cyclical reaction involving such components, preferably a reaction involving an oxidisation of a reduced coenzyme and/or a reduction of an oxidised coenzyme.

By exerting any one of the above-mentioned actions said fourth expressible enzyme activity is controlling a redox system. The above-described maintenance of said redox system may well lead to an increased rate of synthesis of any one or more components of said system. Said maintenance may also lead to an increase in the pool of any one component being comprised in said redox system, notably an increase in the pool of the reduced and/or oxidised form of a coenzyme.

Maintenance shall also be understood to comprise any effect that leads to a decrease in the pool of components of a redox system, notably a decrease in the pool of the reduced and/or oxidised form of a coenzyme.

The person skilled in the art will know how to assess an increase or decrease of any form of a coenzyme or of any redox system and he will know that he must compare the levels of that same coenzyme or redox system in a comparable wild-type microbial cell or an isolated microbial cell grown under identical or substantially similar conditions that allow for a direct comparison of said levels by exploiting state of the art monitoring techniques such as those described by Weuster and de-Graff (1996) in Adv. Biochem. Eng. Biotechnol., vol. 54, pages 75–108 and by Wiechert and de-Graff (1996) in Adv. Biochem. Eng. Biotechnol., vol. 54, pages 109–154. The person skilled in the art will preferably analyse similar or near identical microbial cells with and without said fourth expressible enzyme activity.

Accordingly, the terms increase and decrease relate to a level of expression or synthesis or to a concentration of a coenzyme and/or a redox system. The term level is used interchangeably in the art with terms such a synthesis rate and concentration. The person skilled in the art will be familiar with such terms and attach the correct meaning to their use in different contexts.

By acting to increase and/or decrease the rate of synthesis and/or the pool of a redox system component, the fourth expressible enzyme activity is controlling said intracellular redox system. The term alteration in this context shall be understood to comprise any change or deviation from the presence and/or amount of a redox system present in a comparable wild-type microorganism or an a comparable isolated microbial cell.

Any redox system can generally be perceived to contribute to the provision of a certain redox level in a cell. The totality of all such redox systems in a cell determines the redox level of said cell. The redox level of a cell thus comprises the presence and/or amount of the totality of a reducing power and an oxidising power present in said cell. Accordingly, an alteration of an intracellular redox system can be measured either by monitoring the increase or decrease of a specific redox system, i.e. an increase or decrease in both the oxidised form as well as in the reduced form of a coenzyme constituting said redox system, or alternatively, said alteration can be monitored by measuring an overall cellular redox level.

In one preferred embodiment according to the invention, said fourth expressible enzyme activity provides the means for transfering reducing or oxidizing potential from one redox system to another. Alteration of an intracellular redox system may thus result in an increase or decrease in either the oxidised form or the reduced form of a coenzyme. It may also result in either one of those forms being increased while the other form is decreased. Any such alteration can be measured either by monitoring the increase or decrease of any one specific redox system, i.e. an increase or decrease in either an oxidised form and/or a reduced form of said coenzyme. Alternatively, said alteration can be monitored by measuring an overall intracellular redox level.

The person skilled in the art will be aware of such alterations leading to an increased or decreased redox level and, as exemplified herein and explained further in detail below, the skilled person will be aware of the state of the art techniques available for monitoring an intracellular redox level.

In one embodiment therefore, when said fourth expressible enzyme activity is present in said microbial cell and expressed therein, it results in an increased or decreased level, preferably an increased level, of at least one intracellular coenzyme in its oxidised or reduced form. Said coenzyme in its oxidised/reduced form is preferably selected from the group consisting of $FAD/FADH_2$, $NAD^+/NADH$ and $NADP^+/NADPH$.

Accordingly, the level of at least one intracellular coenzyme in its oxidised or reduced form is either increased or decreased, preferably increased, by a factor of at least 1.005, for example 1.010, such as 1.015, for example 1.020, such as a factor of at least 1.025, for example a factor of at least 1.030, such as 1.035, for example 1.040, such as 1.045, for example 1.050, such as 1.055, for example 1.060, such as at least 1.065, for example a factor of at least 1.070, such as 1.075, for example 1.080, such as 1.085, for example a factor of at least 10.090, such as 1.095, for example 1.100, such as 1.105, for example 10.110, such as 1.115, for example 1.120, such as at least 1.125, for example a factor of at least 1.130, such as 1.135, for example 1.140, for example 1.145, such as 1.150, for example 1.155, such as at least 1.160, for example a factor of at least 1.165, such as a factor of at least 1.170, for example a factor of at least 1.175, such as 1.180, for example 1.185, such as 1.190, for example 1.195, such as a factor of at least 1.200, for example 1.21, such as 1.22, for example 1.23, such as 1.24, for example 1.25, such as 1.26, for example 1.27, such as 1.28, for example 1.29, such as a factor of at least 1.30, for example 1.35, such as 1.40, for example 1.45, such as 1.50, for example 1.55, such as 1.60, for example 1.65, such as 1.70, for example 1.75, such as 1.80, for example 1.85, such as 1.90, for example 1.95, such as a factor of at least 2.0, for example 2.2, such as 2.4, for example 2.6, such as 2.8, for example 3.0, such as 3.2° for example 3.4, such as 3.6, for example 3.8, such as at least 4.0, for example 4.2, such as 4.4, for example 4.6, such as 4.8, for example at least 5.0, such as 5.2, for example 5.4, such as 5.6, for example 5.8, such as at least 6.0, for example 6.2, such as 6.4, for example 6.6, such as 6.8, for example at least 7.0, for example 7.2, such as 7.4, for example 7.6, such as 7.8, for example 8.0, such as 8.2, for example 8.4, such as 8.6, for example 8.8, such as at least 9.0, for example 9.2, such as 9.4, for example 9.6, such as 9.8, for example a factor of at least 10.0.

Although an increase is preferred, it shall be understood that the term alteration is by no means limited to an increase in the level of at least one intracellular coenzyme in its oxidised or reduced form. Said alteration shall also comprise any decrease in the level of at least one intracellular coenzyme in its oxidised or reduced form.

In an embodiment of the invention wherein the expression of said fourth expressible enzyme activity results in an increase or a decrease in the level i.e. concentration of an intracellular redox system as a whole, i.e. an increase or decrease of both of two corresponding oxidised and reduced forms of a coenzyme, said alteration is an increase or decrease, preferably an increase, by a factor of at least 1.005, for example 1.010, such as 1.015, for example 1.020, such as a factor of at least 1.025, for example a factor of at least 1.030, such as 1.035, for example 1.040, such as 1.045, for example 1.050, such as 1.055, for example 1.060, such as at least 1.065, for example a factor of at least 1.070, such as 1.075, for example 1.080, such as 1.085, for example a factor of at least 1.090, such as 1.095, for example 1.100, such as 1.105, for example 1.110, such as 1.115, for example 1.120, such as at least 1.125, for example a factor of at least 1.130, such as 1.135, for example 1.140, for example 1.145, such as 1.150, for example 1.155, such as at least 1.160, for example a factor of at least 1.165, such as a factor of at least 1.170, for example a factor of at least 1.175, such as 1.180, for example 1.185, such as 1.190, for example 1.195, such as a factor of at least 1.200, for example 1.21, such as 1.22, for example 1.23, such as 1.24, for example 1.25, such as 1.26, for example 1.27, such as 1.28, for example 1.29, such as a factor of at least 1.30, such as 1.35, for example 1.40, for example 1.45, such as 1.50, for example 1.55, such as 1.60, for example 1.65, such as 1.70, for example 1.75, such as 1.80, for example 1.85, such as 1.90, for example 1.95, such as a factor of at least 2.0, for example 2.2, such as 2.4, for example 2.6, such as 2.8, for example 3.0, such as 3.2, for example 3.4, such as 3.6, for example 3.8, such as at least 4.0, for example 4.2, such as 4.4, for example 4.6, such as 4.8, for example at least 5.0, such as 5.2, such as 5.4, such as 5.6, for example 5.8, such as at least 6.0, for example 6.2, such as 6.4, for example 6.6, such as 6.8, for example at least 7.0, for example 7.2, such as 7.4, for example 7.6, such as 7.8, for example 8.0, such as 8.2, for example 8.4, such as 8.6, for example 8.8, such as at least 9.0, for example 9.2, such as 9.4, for example 9.6, such as 9.8, for example a factor of at least 10.0.

Said fourth expressible enzyme activity may well result in an increase or a decrease, preferably an increase, of more than one intracellular redox system. It shall be understood that in one embodiment of the invention, said fourth expressible enzyme activity, when expressed, is resulting in an increased level of at least one intracellular redox system.

In a particularly preferred aspect of the invention, said fourth expressible enzyme activity is an intracellular transhydrogenase activity, preferably a pyridine nucleotide transhydrogenase activity, and more preferably a pyridine nucleotide transhydrogenase activity such as that of CTH of *Azotobacter vinelandii* as harboured by *Saccharomyces cerevisiae* TN4 deposited under DSM Accession Number 12267, or a functionally equivalent activity. The term functional equivalent activity is defined herein above and does also apply to the context in which the term is used here.

The pyridine nucleotide transhydrogenase activity is either endogenous or heterologous to said microbial cell wherein it is expressed and said activity is either exhibited by a polypeptide which is membrane-bound in a natural host organism or located i.e. present in the cytoplasm of a natural host organism, said natural host organism preferably being selected from the group of mammalian cells, plant cells, eukaryotic and prokaryotic cells including microbial and bacterial cells such as e.g. Gram-positive microbial prokaryote and a Gram-negative microbial prokaryote.

Expression of said pyridine nucleotide transhydrogenase activity in said microbial cell in one preferred embodiment of the invention results in an increased conversion of NADPH and NAD to NADH and NADP. In another embodiment said expression of said pyridine nucleotide transhydrogenase activity results in an increased consumption of NADPH and an increased formation of NADH. In another embodiment the expression has the effect of increasing the consumption of NADH and increasing the formation of NADPH. In yet another embodiment the expression results in an increased formation of NADH and/or NADP. However, said expression may also result in a decreased formation of NADPH and/or a decreased NADPH/NADP retio. The pyridine nucleotide transhydrogenase activity is preferably expressed in said microbial cell under anaerobic growth conditions and preferably results in the ratio of NADPH/NADP being lower than the ratio of NADH/NAD.

In another preferred embodiment, the transhydrogenase activity, preferably an activity that is membrane-bound in a natural host organism, is inserted into the plasma membrane of a microbial cell, preferably a yeast cell. The transhydrogenase activity would mediate a reaction consuming NADP and generating NADPH. In a particularly preferred embodiment, an *E. coli* transhydrogenase is expressed in a yeast cell and leads to an increased level of NADPH. The expression of the *E. coli* transhydrogenase is coupled to a proton gradient across the membrane of the natural host organism and a similar coupling is likely to be established when the membrane-bound *E. coli* transhydrogenase enzyme is integrated into the plasma membrane of a yeast cell such as e.g. *Saccharomyces cerevisiae*.

In a particularly preferred embodiment, the fourth expressible enzyme activity is that of CTH comprised in *Saccharomyces cerevisiae* strain TN4 deposited under Accession Number DSM 12267.

The microbial cell according to invention is preferably one suitable for storage in the form of a frozen or freeze-dried preparation such as a lyophilisate from which the microbial cell is partly or wholly reconstitutable.

In yet another embodiment of the invention, the microbial cell has been metabolically engineered as described above and is capable of alternative NADH re-oxidation. Said alternative NADH re-oxidation is mediated at least by the combined expression of said above-mentioned first and second expressible enzyme activities. In one preferred embodiment said alternative NADH-reoxidation is mediated by overexpression of said first and second expressible enzyme activities in a microbial cell having a substantially decreased expression of said third expressible enzyme activity, or a microbial cell wherein said expression has been repressed or eliminated or deleted. Said fourth expressible enzyme activity may optionally be expressed concomitantly with an overexpression of said first and second expressible enzyme activities and a substantially reduced and preferably eliminated expression of said third expressible enzyme activity. In one preferred embodiment of the invention, said first, second, third and fourth expressible enzyme activities are those of a glutamate synthase, a glutamine synthetase, a glutamate dehydrogenase and a transhydrogenase, respectively.

Alternative NADH re-oxidation shall be understood to comprise the introduction of a novel major pathway for NADH re-oxidation or a generation of a substantially altered pathway for NADH-reoxidation in a microbial cell. Alteration in respect of a pathway for alternative NADH oxidation shall be understood in the context of the rate of a reaction mediating a conversion of one metabolite to another, said reaction also resulting in NADH re-oxidation. The rate of said re-oxidation reaction in a microbial cell capable of alternative NADH re-oxidation is substantially increased as compared to the rate of said reaction in a comparable microbial cell. The definition of the term comparable in respect of microbial cells is already introduced herein above.

Alternative NADH re-oxidation is an example of a microbial cell wherein the expression of a transhydrogenase, in combination with several additionally preferred expressible enzyme activities, are capable of generating a purposeful redesigning of a complex network of metabolic reactions. The redesigned microbial cell is invented by replacing or supplementing a normally dominant first metabolic reaction with a second reaction that is normally insignificant in relation to reaction rate and/or product formation as compared to said first dominant reaction. However, by significantly increasing said second reaction while at the same time significantly decreasing or even eliminating said first reaction, it is possible to achieve an alternative NADH re-oxidation. In a further embodiment of the invention, there is also provided a microbial cell capable of alternative NADPH re-oxidation or alternative NADP reduction.

In another aspect of the invention, there is provided a composition comprising the microbial cell and a carrier, preferably a physiologically acceptable carrier and more preferably a water-based liquid such as a broth suitable for culturing said microbial cell. The composition in a preferred embodiment is a fermentation starter culture.

There is also provided the aspect of a nucleotide sequence encoding a novel and industrially relevant transhydrogenase enzyme activity, said sequence comprising SEQ ID NO:1, as illustrated herein below, or part thereof, including functionally equivalent derivatives thereof encoding a transhydrogenase enzyme activity, preferably but not limited to conservative nucleotide substitutions and/or nucleotide deletions and/or nucleotide insertions. Said functionally equivalent derivatives may thus be at least 99.9 percent identical to SEQ ID NO:1, such as at least 99.8 percent identical to SEQ ID NO:1, for example at least 99.7 percent identical, such as at least 99.6 percent identical, for example at least 99.5 percent identical, such as at least 99.4 percent identical, for example at least 99.3 percent identical, such as at least 99.2 percent identical, for example at least 99.1 percent identical, such as at least 99 percent identical to SEQ ID NO:1, for example at least 98.5 percent identical to SEQ ID NO:1, such as at least 98.0 percent identical, for example 97.5 percent identical, such as at least 97.0 percent identical to SEQ ID NO:1, for example at least 96.5 percent identical, such as at least 96.0 percent identical, for example at least 95.5 percent identical, such as at least 95.0 percent identical, for example at least 94.5 percent identical, such as at least 94.0 percent identical, for example at least 93.5 percent identical, such as at least 93.0 percent identical to SEQ ID NO:1, for example at least 92.5 percent identical, such as at least 92.0 percent identical, for example at least 91.5 percent identical, such as at least 91.0 percent identical, for example at least 90.5 percent identical, such as at least 90.0 percent identical, for example at least 85.0 percent identical to SEQ ID NO:1. In one embodiment, SEQ ID NO:1 is a sequence that is synthesised partly or wholly in vitro.

In a further aspect of the invention there is provided a recombinant DNA-replicon in the form of a vector comprising the nucleotide sequence designated SEQ ID. NO: 1 including functionally equivalent derivatives. The nucleotide sequence designated SEQ ID. NO: 1 is preferably operably linked to an expression signal comprised in said replicon, said expression signal directing expression of said nucleotide sequence. There is also provided a microbial cell microbial cell harbouring the nucleotide sequence designated SEQ ID NO:1 or a recombinant replicon in the form of a vector harbouring said nucleotide sequence.

The recombinant DNA-replicon is preferably one capable of replicating in a yeast cell and/or in a prokaryotic microbial cell such as a lactic acid bacterial cell. Preferred yeast vectors comprise a selectable marker and one or more sites in a nucleotide sequence specific for a restriction endonuclease. An autonomously replicating sequence (ARS) mediates replication of said replicon when harboured in a yeast cell. The vector is preferably based on a plasmid selected from the group consisting of a yeast episomal plasmid (Yep), such as the 2 μm plasmid, a yeast replicating plasmid (Yrp), a yeast centromeric plasmid (Ycp) and a yeast-integrating plasmid (Yip). A particularly preferred replicon is the one harboured by *Saccharomyces cerevisiae* strain TN4 deposited under Accession Number DSM 12267.

Vectors capable of being maintained in a prokaryotic microbial cell such as a lactic acid bacterial cell are well described in the literature and preferably contain a replicon directing e.g. rolling circle replication or θ-replication, a selectable marker such as a nonsense mutation preventing selection and/or replication unless suppressed by a suppresser comprised by a cell comprising said vector, and one or more sites cleavable by a restriction endonuclease.

In a further aspect of the invention, there is provided an amino acid sequence encoded by the nucleotide sequence designated SEQ ID NO: 1, or any functionally equivalent derivative thereof, said amino acid sequence comprising the sequence SEQ ID NO:2, as illustrated herein below, or a part thereof, including any functionally equivalent derivatives exhibiting transhydrogenase activity, preferably, but not limited to, functionally equivalent derivatives comprising conservative amino acid substitutions.

Said functionally equivalent derivative of said amino acid sequence designated SEQ ID NO: 2 may thus be at least 99 percent identical to SEQ ID NO:2, such as at least 98 percent identical to SEQ ID NO:2, for example at least 97 percent identical, such as at least 96 percent identical, for example at least 95 percent identical, such as at least 94 percent identical, for example at least 93 percent identical, such as at least 92 percent identical, for example at least 91 percent identical, such as at least 90 percent identical to SEQ ID NO:2, for example at least 89 percent identical to SEQ ID NO:2, such as at least 88 percent identical, for example 87 percent identical, such as at least 86 percent identical to SEQ ID NO:2, for example at least 85 percent identical to SEQ ID NO:2. In one embodiment, SEQ ID NO:2 is a sequence that is synthesised partly or wholly in vitro.

In a further aspect of the invention there is provided a microbial cell, preferably a yeast cell or a bacterial cell, or a composition comprising said cell, for use in a production of a first metabolite such as a primary or secondary metabolite, preferably a primary metabolite and more preferably an alcohol or an acid, such as e.g. ethanol, glycerol, acetic acid and propionic acid, ethanol being particularly preferred.

When the first metabolite is a secondary metabolite, said secondary metabolite is preferably selected from the group of secondary metabolites consisting of a β-lactam, a polyketide, a terpene, a steroid, a quinone, a coumarin, a flavonoid, an alkaloid, a piperidine, a pyridine, and the like.

Said production of said first metabolite is preferably substantially increased as compared to the production of said first metabolite in a comparable wild-type cell or a comparable isolated microbial cell. Accordingly, said microbial cell production of said first metabolite is increased at least by a factor of 1.02, such as a factor of at least 1.04, for example 1.06, such as 1.08, for example 1.10, such as at least 1.12, for example 1.14, such as 1.16, for example 1.18, such as 1.2, for example 1.25, such as 1.3, for example 1.4, such as 1.5, for example 1.6, such as 1.7, for example 1.8, such as 1.9, for example 2.0, such as 2.25, for example 2.5, such as 3, for example 3.5, such as a factor of at least 4, for example 4.5, such as 5, for example 6, such as 7, for example 8, such as 9, for example 10, such as 15, for example 20, such as 25, for example 30, such as 35, for example 40, such as 50, for example 60, such as 80, for example at least 100, such as 150, for example 200, such as 250, for example 300, such as 350, for example 400, such as 500, for example 600, such as 800, for example at least 1000, such as 1500, for example 2000, such as 2500, for example 3000, such as 3500, for example 4000, such as at least 5000, for example 6000, such as 8000, for example at least 10000, such as 15000, for example 20000, such as at least 25000, for example 30000, such as 35000, for example 40000, such as a factor of at least 50000.

It may furthermore be advantageous to produce and/or purify by means of any state of the art down-stream processing technique said first metabolite in an organism such as e.g. a fungal cell, a yeast cell or a bacterial cell. Any of said eukaryotic or prokaryotic cells for use in said production preferably qualify for GRAS status ("Generally Regarded As Safe") with the Federal Drug Administration of the United States of America.

In another embodiment, there is provided a microbial cell, preferably a yeast cell, for use in said production of said first metabolite, said cell further producing a second metabolite, preferably glycerol, said production of said second metabolite being substantially decreased as compared to the production of said second metabolite in a comparable wild-type cell or a comparable isolated microbial cell.

Accordingly, said production of said second metabolite is decreased by at least 2 percent, such as 4 percent, for example at least 6 percent, such as 8 percent, for example at least 10 percent, such as 12 percent, for example 14 percent, such as 16 percent, for example 18 percent, such as at least 20 percent, for example 24 percent, such as at least 30 percent, for example 35 percent, such as at least 40 percent, for example 50 percent, such as 60 percent, for example at least 70 percent, such as 80 percent, for example at least 90 percent, such as decreased by at least 92 percent, for example 94 percent, such as 96 percent, for example 98 percent, such as decreased by 99 percent or decreased to such an extent that said second metabolite is virtually unassayable using state of the art assays for identifying and/or quantifying said second metabolite.

When the microbial cell is a prokaryotic cell such as e.g. a lactic acid bacterial cell for use in the production of a first metabolite, said first metabolite is selected from the group consisting of lactic acid and an aroma component such as acetoin, acetaldehyde, 2,3-butylene glycol, or diacetyl.

In one embodiment, the microbial cell or the composition according to the invention is preferably used in a production of a first metabolite or used in a method of generating alternative intracellular NADH re-oxidation. Accordingly, the microbial cell is providing a novel or, in terms of efficiency and/or overall rate of reaction, a much improved pathway for alternative NADH re-oxidation for the purpose of providing, supplementing and/or increasing a pool of intracellular NAD, said provision, supplementation and/or increase being used in a process of altering, directing and/or redirecting the flux of primary and/or secondary metabolites in said cell.

In another embodiment there is provided a microbial cell for use in a production of a first metabolite, said cell harbouring a novel or, in terms of efficiency and/or overall rate of reaction, a much improved pathway for alternative NAD reduction for the purpose of providing, supplementing and/or increasing a pool of intracellular NADH, said provision, supplementation and/or increase being used in a process of altering, directing and/or redirecting the flux of primary and/or secondary metabolites in said cell.

In yet another embodiment of the invention, there is provided a microbial cell for use in the production of a first metabolite, said cell harbouring a novel or, in terms of efficiency and/or overall rate of reaction, a much improved pathway for alternative NADPH re-oxidation for the purpose of providing, supplementing and/or increasing a pool of intracellular NADP, said provision, supplementation and/or increase being used in a process of altering, directing and/or redirecting the flux of primary and/or secondary metabolites in said cell.

In a still further embodiment of the invention, there is provided a microbial cell for use in the production of a first metabolite, said cell harbouring a novel or, in terms of efficiency and/or overall rate of reaction, a much improved pathway for alternative NADP reduction for the purpose of providing, supplementing and/or increasing a pool of intracellular NADPH, said provision, supplementation and/or increase being used in a process of altering, directing and/or redirecting the flux of primary and/or secondary metabolites in said cell.

In a yet further aspect of the invention there is provided a microbial cell according to invention for use in a preparation of a drinkable or an edible product. There is also provided a microbial cell for use in a production of a first metabolite for use in a drinkable or an edible product, preferably a product having desirable organoleptic qualities. In one embodiment, said first metabolite has and/or provides a desirable organoleptic quality to said product. In a particularly preferred embodiment, said first metabolite is ethanol.

The microbial cell for use in a production of a first metabolite according to the invention, in one embodiment, further produces a second metabolite, the production of said second metabolite being substantially decreased as compared to the production of said second metabolite in a comparable wild-type cell or a comparable isolated microbial cell, said decreased production resulting in a provision of a desirable organoleptic quality to said product. In a further embodiment said product is a functional food.

In yet another aspect of the invention there is provided the use of a microbial cell or a composition in a production of a first metabolite, said metabolite being a primary metabolite or a secondary metabolite, a metabolite endogenous to said microbial cell or a gene product heterologous to said microbial cell.

In a preferred embodiment there is provided a use of a microbial cell wherein said production of said first metabolite is substantially increased as compared to the production of said first metabolite in a comparable wild-type cell or a comparable isolated microbial cell. Said production of said first metabolite is increased at least by a factor of 1.01, such as 1.02, for example 1.03, such as a factor of at least 1.04, for example 1.05, such as 1.06, for example 1.07, such as 1.08, for example 1.09, such as 1.10, for example 1.11, such as at least 1.12, for example 1.14, such as 1.16, for example 1.18, such as 1.2, for example 1.25, such as 1.3, for example 1.4, such as 1.5, for example 1.6, such as 1.7, for example 1.8, such as 1.9, for example 2.0, such as 2.25, for example 2.5, such as 3, for example 3.5, such as a factor of at least 4, for example 4.5, such as 5, for example 6, such as 7, for example 8, such as 9, for example 10, such as 15, for example 20, such as 25, for example 30, such as 35, for example 40, such as 50, for example 60, such as 80, for example at least 100, such as 150, for example 200, such as 250, for example 300, such as 350, for example 400, such as 500, for example 600, such as 800, for example at least 1000, such as 1500, for example 2000, such as 2500, for example 3000, such as 3500, for example 4000, such as at least 5000, for example 6000, such as 8000, for example at least 10000, such as 15000, for example 20000, such as at least 25000, for example 30000, such as 35000, for example 40000, such as a factor of at least 50000.

It is preferred that the microbial cell is a yeast cell or a prokaryotic microbial cell and that said first metabolite is an alcohol or an acid, preferably ethanol, acetic acid, lactic acid or propionic acid.

In a preferred use there is provided a microbial cell, preferably a yeast cell, further producing a second metabolite, said production of said second metabolite being substantially decreased as compared to the production of said second metabolite in a comparable wild-type cell or a comparable isolated microbial cell. Particularly preferred is a use wherein said second metabolite is glycerol or an undesirable aroma component naturally produced by a lactic acid bacterial cell.

The production of said second metabolite, preferably glycerol or an undesirable aroma component produced by a lactic acid bacterial cell, is reduced in a preferred use of said microbial cell by at least by at least 2 percent, such as 4 percent, for example at least 6 percent, such as 8 percent, for example at least 10 percent, such as 12 percent, for example 14 percent, such as 16 percent, for example 18 percent, such as at least 20 percent, for example 24 percent, such as at least 30 percent, for example 35 percent, such as at least 40 percent, for example 50 percent, such as 60 percent, for example at least 70 percent, such as 80 percent, for example at least 90 percent, such as decreased by at least 92 percent, for example 94 percent, such as 96 percent, for example 98 percent, such as decreased by 99 percent or decreased to such an extent that said second metabolite is virtually unassayable using state of the art assays for identifying and/or quantifying said second metabolite.

Another preferred use of said microbial cell is in preparation of a drinkable or edible product or in a production of a first metabolite for use in said drinkable or edible product, said first metabolite having and/or providing a desirable organoleptic quality to said product. Preferably the first metabolite is ethanol or, when the microbial cell is a lactic acid bacterial cell, an aroma component produced by said lactic acid bacterial cell, preferably acetoin and/or diacetylactis.

A much preferred use of said microbial cell in said preparation of said drinkable or edible product is that of a microbial cell according to the invention, preferably a yeast cell or a lactic acid bacterial cell, further producing a second metabolite, said production of said second metabolite being substantially decreased as compared to the production of said second metabolite in a comparable wild-type cell or a comparable isolated microbial cell, said decreased production resulting in a provision of a desirable organoleptic quality to said product, said decrease is at least 2 percent, such as 4 percent, for example at least 6 percent, such as 8 percent, for example at least 10 percent, such as 12 percent, for example 14 percent, such as 16 percent, for example 18 percent, such as at least 20 percent, for example 24 percent, such as at least 30 percent, for example 35 percent, such as at least 40 percent, for example 50 percent, such as 60 percent, for example at least 70 percent, such as 80 percent, for example at least 90 percent, such as decreased by at least 92 percent, for example 94 percent, such as 96 percent, for example 98 percent, such as decreased by 99 percent or decreased to such an extent that said second metabolite is virtually unassayable using state of the art assays for identifying and/or quantifying said second metabolite.

There is also provided a use of a microbial cell, preferably a yeast cell or a lactic acid bacterial cell, in a preparation of a functional food.

In a yet further aspect of the invention there is provided a method of producing a first metabolite, said method comprising the steps of
i) cultivating a microbial cell in a suitable growth medium and under such conditions that said microbial cell is producing a first metabolite and optionally
ii) isolating said first metabolite in a suitable form, and further optionally
iii) purifying said isolated first metabolite.

The method comprises the culturing of any microbial cell including a microbial eukaryote and a microbial prokaryote. Among microbial eukaryotes, yeast cells and fungal cells are preferred, such as yeast cells like e.g. *Saccharomyces cerevisiae, Schizosaccharomyces pombe, Pichia pastoris* and the like, as well as algae such as e.g. *Chlamydomonas reinhardi*, slime moulds such as e.g. *Dictyostelium discoideum* and filamentous fungi. Preferred filamentous fungi according to the method are species of *Neurospora* and *Aspergillus* such as e.g. *Neurospora crassa, Aspergillus nidulans, Aspergillus niger, Aspergillus cryzae* and *Penicillium chrysogenum*. Particularly preferred are many industrially relevant yeast cells, slime moulds and filamentous fungi providing a source of production of products such as e.g. antibiotics, steroids, pigments, enzymes, organic alcohols and acids, amino acids, polysaccharides and the like.

The method also pertains to the culturing of microbial prokaryotes such as Gram-positive species such as e.g. *Bacillus subtilis, Bacillus thuringensis, Bacillus licheniformis, Bacillus lentus* and *Bacilus stearothermophilus* and Gram-negative species such as *Escherichia coli*. Particularly preferred are also lactic acid bacterial species such as e.g. *Lactococcus lactis, Lactococcus lactis* subsp. *lactis, Lactococcus lactis* subsp. *cremoris, Lactococcus lactis* subsp. *diacetylactis, Leuconostoc* species, *Lactobacillus* species, *Pediococcus* species and similar industrially relevant species like e.g. *Bifidobacterium*.

Embodiments of this aspect of the invention comprise a method wherein said first metabolite is either a primary metabolite or a secondary metabolite. The metabolite may be produced in a cell also capable of further producing e.g. an endogenous or a heterologous product selected from the group consisting a protease, an amylase, a cellulase, a β-glucanase, an endoglucanase, a phosphatase, a xylanase, a lipase, a β-lactamase, a β-galactosidase, a βglucoronidase, and a xylosidase. When the microbial cell is a lactic acid bacterium, said metabolite is preferably diacetyl, acetoin, or lactic acid.

The method according to the invention pertains in one embodiment to an increased production of said first metabolite, such as a substantially increased production, as compared to the production of said first metabolite in a comparable wild-type cell or a comparable isolated microbial cell. Accordingly, there is provided a method by which said production of said first metabolite is increased at least by a factor of 1.01, such as 1.02, for example 1.03, such as a factor of at least 1.04, for example 1.05, such as 1.06, for example 1.07, such as 1.08, for example 1.09, such as 1.10, for example 1.11, such as at least 1.12, for example 1.14, such as 1.16, for example 1.18, such as 1.2, for example 1.25, such as 1.3, for example 1.4, such as 1.5, for example 1.6, such as 1.7, for example 1.8, such as 1.9, for example 2.0, such as 2.25, for example 2.5, such as 3, for example 3.5, such as a factor of at least 4, for example 4.5, such as 5, for example 6, such as 7, for example 8, such as 9, for example 10, such as 15, for example 20, such as 25, for example 30, such as 35, for example 40, such as 50, for example 60, such as 80, for example at least 100, such as 150, for example 200, such as 250, for example 300, such as 350, for example 400, such as 500, for example 600, such as 800, for example at least 1000, such as 1500, for example 2000, such as 2500, for example 3000, such as 3500, for example 4000, such as at least 5000, for example 6000, such as 8000, for example at least 10000, such as 15000, for example 20000, such as at least 25000, for example 30000, such as 35000, for example 40000, such as a factor of at least 50000.

When being isolated or when being isolated and purified, said metabolite is isolated or isolated and purified according to any available state of the art techniques for isolating or isolating and purifying a metabolite.

In one preferred embodiment of the invention, the method pertains to the production in a yeast cell or in a lactic acid bacterial cell of a first metabolite such as a primary or secondary metabolite, preferably a primary metabolite and more preferably an alcohol or an acid, such as e.g. ethanol, glycerol, acetic acid and propionic acid, with ethanol being particularly preferred. In a much preferred embodiment, the microbial cell according to the method is a yeast cell and the first metabolite is ethanol. When said first metabolite is a secondary metabolite, said secondary metabolite is preferably selected from the group of secondary metabolites consisting of a β-lactam, a polyketide, a terpene, a steroid, a quinone, a coumarin, a flavonoid, an alkaloid, a piperidine, a pyridine, and the like.

In another embodiment of the method according to the invention, there is provided a microbial cell, preferably a yeast cell or a lactic acid bacterial cell, said cell further producing a second metabolite, the production of said second metabolite being substantially decreased as compared to the production of said second metabolite in a comparable wild-type cell or a comparable isolated microbial cell. In one embodiment, said decrease of said production of said second metabolite is at least 2 percent, such as 4 percent, for example at least 6 percent, such as 8 percent, for example at least 10 percent, such as 12 percent, for example 14 percent, such as 16 percent, for example 18 percent, such as at least 20 percent, for example 24 percent, such as at least 30 percent, for example 35 percent, such as at least 40 percent, for example 50 percent, such as 60 percent, for example at least 70 percent, such as 80 percent, for example at least 90 percent, such as decreased by at least 92 percent, for example 94 percent, such as 96 percent, for example 98 percent, such as decreased by 99 percent or decreased to such an extent that said second metabolite is virtually unassayable using state of the art assays for identifying and/or quantifying said second metabolite.

In one preferred embodiment the second metabolite is glycerol when said cell is a yeast cell having a substantially increased production of a first metabolite, preferably ethanol. In another preferred embodiment, when the cell is a lactic acid bacterial cell, the second metabolite is an undesirable aroma component naturally produced by a lactic acid bacterial cell.

In one embodiment of the method according to the invention the microbial cell is a lactic acid bacterial cell and said first metabolite is selected from the group consisting of lactic acid and a desirable aroma component such as acetoin and diacetyl. In another embodiment, the microbial cell is a Gram-positive bacterial cell, preferably a cell capable of producing an enzyme such as e.g. a protease, an amylase, a cellulase, a β-glucanase, an endoglucanase, a phosphatase, a xylanase, a lipase, a β-lactamase, a β-galactosidase or a xylosidase.

There is also provided a method for generating an alternative re-oxidation of a reduced coenzyme, said method, in one embodiment, consisting essentially of providing in a microbial cell a novel or, in terms of efficiency and/or overall rate of reaction, a much improved pathway for alternative NADH and/or NADPH re-oxidation for use in providing, supplementing and/or increasing a pool of intracellular NAD and/or NADP, said provision, supplementation and/or increase being used in a process of altering, directing and/or redirecting the flux of primary and/or secondary metabolites in said cell.

Also, there is provided a method for generating an alternative reduction of an oxidised coenzyme, said method consisting essentially of providing in a microbial cell a novel or, in terms of efficiency and/or overall rate of reaction, a much improved pathway for alternative NAD and/or NADP reduction for the purpose of providing, supplementing and/or increasing a pool of intracellular NADH and/or NADPH, said provision, supplementation and/or increase being used in a process of altering, directing and/or redirecting the flux of primary and/or secondary metabolites in said cell.

In a yet further aspect of the invention, there is provided a method of constructing a microbial cell according to the invention, said method comprising the steps of i) operably linking a nucleotide sequence encoding said first expressible enzyme activity with an expression signal not natively associated with said nucleotide sequence, and/or ii) operably linking a nucleotide sequence encoding said second expressible enzyme activity with an expression signal not natively associated with said nucleotide sequence, and iii) eliminating said third expressible enzyme activity from said microbial cell, or optionally operably linking a nucleotide sequence encoding said third expressible enzyme activity with an expression signal not natively associated with said nucleotide sequence, said expression signal generating a reduced expression of said nucleotide sequence, and iv) introducing said operably linked nucleotide sequences obtained under i) and iii), and optionally the nucleotide sequence obtained under ii), into said microbial cell, or v) introducing said operably linked nucleotide sequence obtained under i), and optionally the nucleotide sequence obtained under ii), into said microbial cell obtained under iii) wherein said third expressible enzyme activity has been eliminated.

Said expression signal may direct a substantially constitutive expression, a constitutive α-pression during growth of said cell in a particular growth phase, an inducible expression in response to the presence and/or level of an inducer or the absence and/or level of a repressor. The expression signal is preferably a regulatable expression signal such as a regulatable transcription initiation signal and/or a regulatable translational initiation signal, such as an expression signal regulatable in response to an alteration in a value, level and/or concentration of a factor such as a physiological growth parameter, preferably a parameter selected from the group consisting of pH, temperature, salt content including osmolarity, anaerobicity, aerobicity including oxygen level, energy level including a membrane potential and a proton motive force.

The expression signal is preferably a promoter being either growth phase regulated, inducible and/or repressible and/or, in a natural host organism, directing expression of a gene encoding a gene product involved in mediating a reaction of a biosynthetic pathway and/or a major metabolic pathway, preferably a pathway selected from the group of pathways consisting of glycolysis, gluconeogenesis, citric acid cycle, and pentose phosphate pathway.

The expression signal may be further regulated by an upstream activating sequence (UAS), by an enhancer element or by a silencer element. The person skilled in the art will be aware of general molecular biology techniques for use in the construction in vitro of a recombinant DNA molecule. Such techniques are described e.g. in Sambrook et al. (1989) and in Old and Primrose (ibid.). Said skilled artisan will further be aware of the academic literature including general textbooks on molecular biology and genetic engineering and he will be able to combine various expression signals such as putative or recognised promoter regions with a range of regulatory nucleotide sequences generally known to exert an effect on the level of gene expression. The skilled person is able to monitor gene expression by construction of suitable transcriptional and/or translational fusions of an expression signal to a reporter gene generally available in the art. An expression signal can be a cloned expression signal or an in vitro synthesised expression signal. Expression signals in prokaryotic microbial cells are known to comprise so-called -35 and -10 regions and numerous examples of such regions are available from various databases.

Expression signals may be optimised by increasing the promoter strength, by adjusting translational initiation sequences, by optimising the choice of codons by using so-called highly expressed codons, by adjusting the secondary structure of the mRNA, by increasing the efficiency of transcriptional termination, by increasing or decreasing a copy number of a vector, or by increasing or decreasing the stability of said vector.

The microbial cell is preferably a fungal cell, a yeast cell, or a bacterial cell. *Saccharomyces cerevisiae, Schizosaccharomyces pombe* and *Pichia pastoris* are preferred yeast cells and a among bacterial cells are lactic acid bacteria preferred, particularly lactic acid bacterial species such as e.g. *Lactococcus lactis, Lactococcus lactis* subsp. *lactis, Lactococcus lactis* subsp. *cremoris, Lactococcus lactis* subsp. *diacetylactis, Leuconostoc* species, *Lactobacillus* species, *Pediococcus* species and similar industrially relevant species like e.g. *Bifidobacterium*.

Also preferred are algae such as e.g. *Chlamydomonas reinhardi*, slime moulds such as e.g. *Dictyostelium discoideum* and filamentous fungi such as species of *Neurospora* and *Aspergillus* such as e.g. *Neurospora crassa* and *Aspergillus nidulans, Aspergillus niger, Aspergillus crytae* and *Penicillium chrysogenum*. Particularly preferred are also many industrially relevant yeast cells, slime moulds and filamentous fungi providing a production of products such as e.g. antibiotics, steroids, pigments, enzymes, organic alcohols and acids, amino acids, polysaccharides and the like.

Among preferred microbial prokaryotes are bacterial cells such as Gram-positive species such as e.g. *Bacillus subtilis, Bacillus thuringensis, Bacillus licheniformis, Bacillus lentus* and *Bacilus stearothermophilus*, as well as Gram-negative species such as *Escherichia coli*. Particularly preferred are also lactic acid bacterial species such as e.g. *Lactococcus lactis, Lactococcus lactis* subsp. *lactis, Lactococcus lactis* subsp. *cremoris, Lactococcus lactis* subsp. *diacetylactis, Leuconostoc* species *Lactobacillus* species, *Pediococcus* species and similar industrially relevant species like e.g. *Bifidobacterium*.

In one embodiment of the method, the microbial cell is a yeast cell and the first expressible enzyme activity is a glutamate synthase activity, preferably a glutamate synthase activity encoded by GLT1 of *Saccharomyces cerevisiae* TN17 as deposited under DSM Accession Number 12275, or a functionally equivalent activity. The second expressible enzyme activity is a glutamine synthetase activity, preferably a glutamine synthetase activity encoded by GLN1 of *Saccharomyces cerevisiae* TN15 as deposited under DSM Accession Number 12274, or a functionally equivalent activity. The third expressible enzyme activity, when present in said cell, is a glutamate dehydrogenase activity and preferably an activity encoded by GDH1 of *Saccharomyces cerevisiae*. There is also provided a method wherein said cell is *Saccharomyces cerevisiae* TN19 as deposited under DSM Accession Number 12276. The method may comprise a further step of freezing or freeze-drying the microbial cell in the preparation of a reconstitutable lyophilisate.

In one presently preferred embodiment the microbial cell is a lactic acid bacteria as exemplified herein, and said fourth expressible enzyme activity is, at least in its native host organism, a cytoplasmic transhydrogenase, said expression of said cytoplasmic transhydrogenase resulting in an altered and/or novel product formation and/or metabolite production of said lactic acid bacteria.

An example of said novel product and/or metabolite formation is given herein below. Lactic acid bacteria metabolise pyruvate through a number of different pathways. The metabolite is converted into lactate by lactate dehydrogenase, into acetyl-CoA and $CO_2$ by pyruvate dehydrogenase, into formate by pyruvate formate lyase and into acetolactate and $CO_2$ by acetolactate decarboxylase. The carbon flux distribution through these pathways is dependent on the external growth conditions. This control is exerted through changes in the intracellular NADH/NAD$^+$ ratio (C. Garrigues, P. Loubicre, N. D. Lindley and M. Cocaign-bousquet (1997). *J. Bacteriology* 179, 5282–5287; F. Lopez de Felipe, M. Kleerebezem. W. M. de Vos and J. Hugenholtz (1998). *J. Bacteriology* 180, 3804–3808). This is illustrated by the observations from physiological studies of lactic acid bacteria that are listed below.

Lactic acid bacteria with an increased formation of the secondary metabolite diacetyl are relevant for a number of industrial applications. It has been shown that overexpression of NADH-oxidase from *Streptococcus mutans* in *L. lactis* results in a shift from homolactic (production of lactic acid) to mixed acid fermentation (production of lactic acid, acetic acid, acetoin and diacetyl) under aerobic growth conditions. This effect is ascribed to a decrease in the intracellular NADH/NAD$^+$ ratio of the recombinant strain (F. Lopez de Felipe, M. Kleerebezem, W. M. de Vos and J. Hugenholtz (1998), *J. Bacteriology* 180, 3804–3808). Expression of the cytoplasmic transhydrogenase in lactic acid bacteria is expected to have a similar effect on the NADH/NAD$^+$ ratio if the reaction occurs in the direction from NADH to NADPH.

It has been shown that the product formation by *L. lactis* changes when the carbon source is shifted from glucose to lactose and that this effect is due to a lower flux through glycolysis, resulting in a lower NADH/NAD$^+$ ratio (C. Garrigues, P. Loubiere, N. D. Lindley and M. Cocaign-bousquet (1997). *J. Bacteriology* 179, 5282–5287). Thus, under anaerobic growth conditions on glucose the majority (93%) of the carbon source was converted into lactate, while only 4% of the carbon source was converted into lactate when lactose was used as carbon source. The remaining part was converted into formate, acetate and ethanol. The authors state that lactate formation is reduced due to a 3-fold lower NADH/NAD$^+$ ratio during growth on lactose as compared with glucose, resulting in deactivation of lactate dehydrogenase. Instead, the carbon flux towards the pyruvate node is redirected towards formation of acetate, ethanol and formate in order to synthesise ATP and reoxidise NADH. Expression of the cytoplasmic transhydrogenase in lactic acid bacteria is expected to have a similar effect on the NADHINAD+ ratio if the reaction occurs in the direction from NADH to NADPH. Thus, it is expected that cultivation of a transhydrogenase-containing recombinant strain of lactic acid bacteria under anaerobic growth conditins will result in production of several new byproducts besides lactate.

Since lactate dehydrogenase is activated by a high NADH/NAD$^+$ ratio it is expected that the flux towards lactate can be increased by expressing transhydrogenase in lactic acid bacteria under conditions where the transhydrogenase reaction occurs in the direction from NADPH to NADH.

The invention will be further exemplified in the below provided examples directed to preferred embodiments of the invention. It will be understood that the invention is by no means limited to said examples. The examples include figures illustrating the invention and the legends to said figures are listed below.

FIGURE LEGENDS

Figure 3:
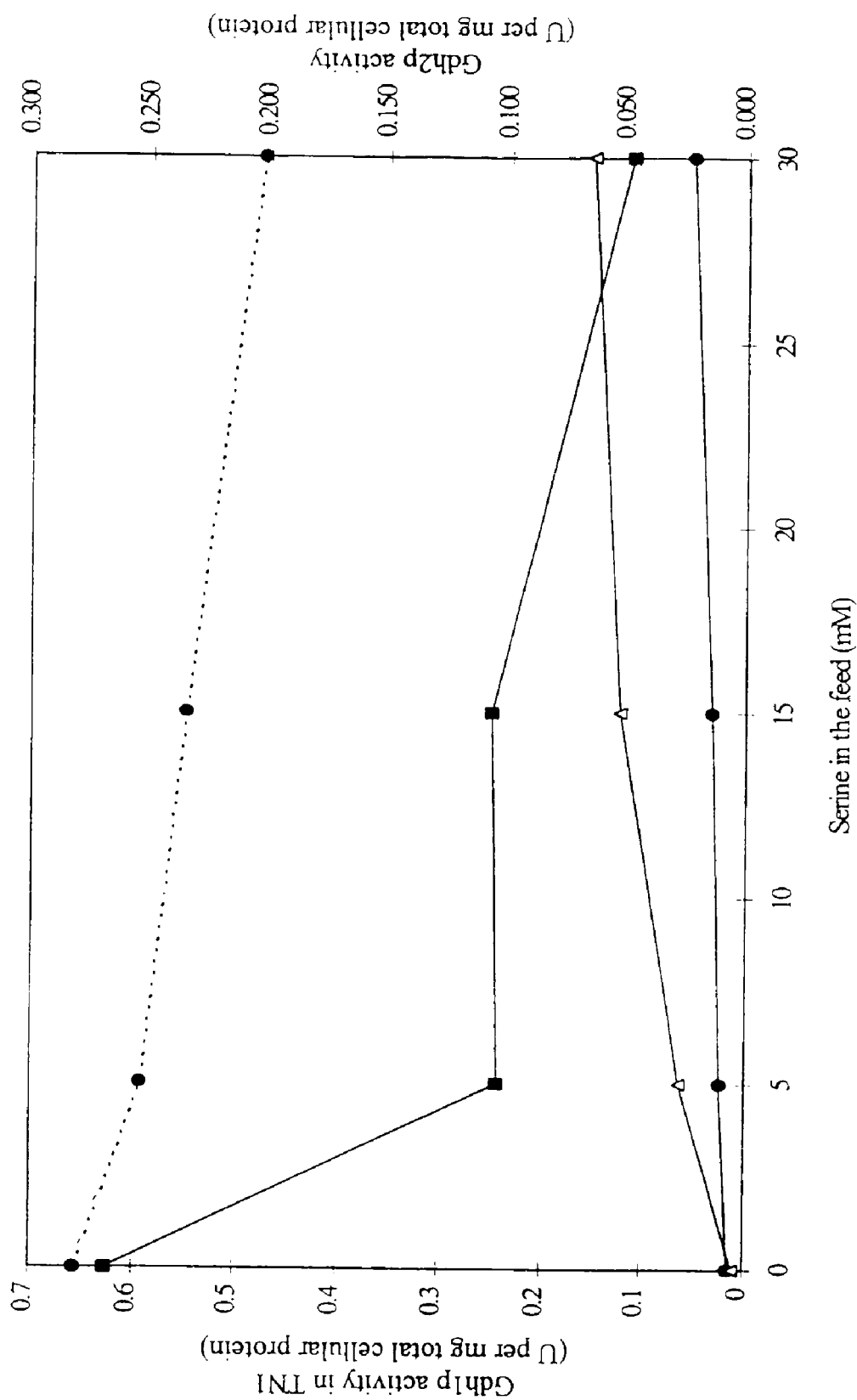

FIG. 3 shows the specific enzyme activities of the NADPH-dependent and NADH-dependent glutamate dehydrogenases in protein extracts from biomass samples withdrawn from the continuous cultivations of strains TN1, TN9 and TN12 with increasing amounts of serine in the feed. Dotted line, ●: Gdh1p activity in TN1. Normal line, ●: Gdh2p activity in TN1. Normal line, ■: Gdh2p activity in TN9. Normal line, Δ: Gdh2p activity in TN12.

Figure 4:
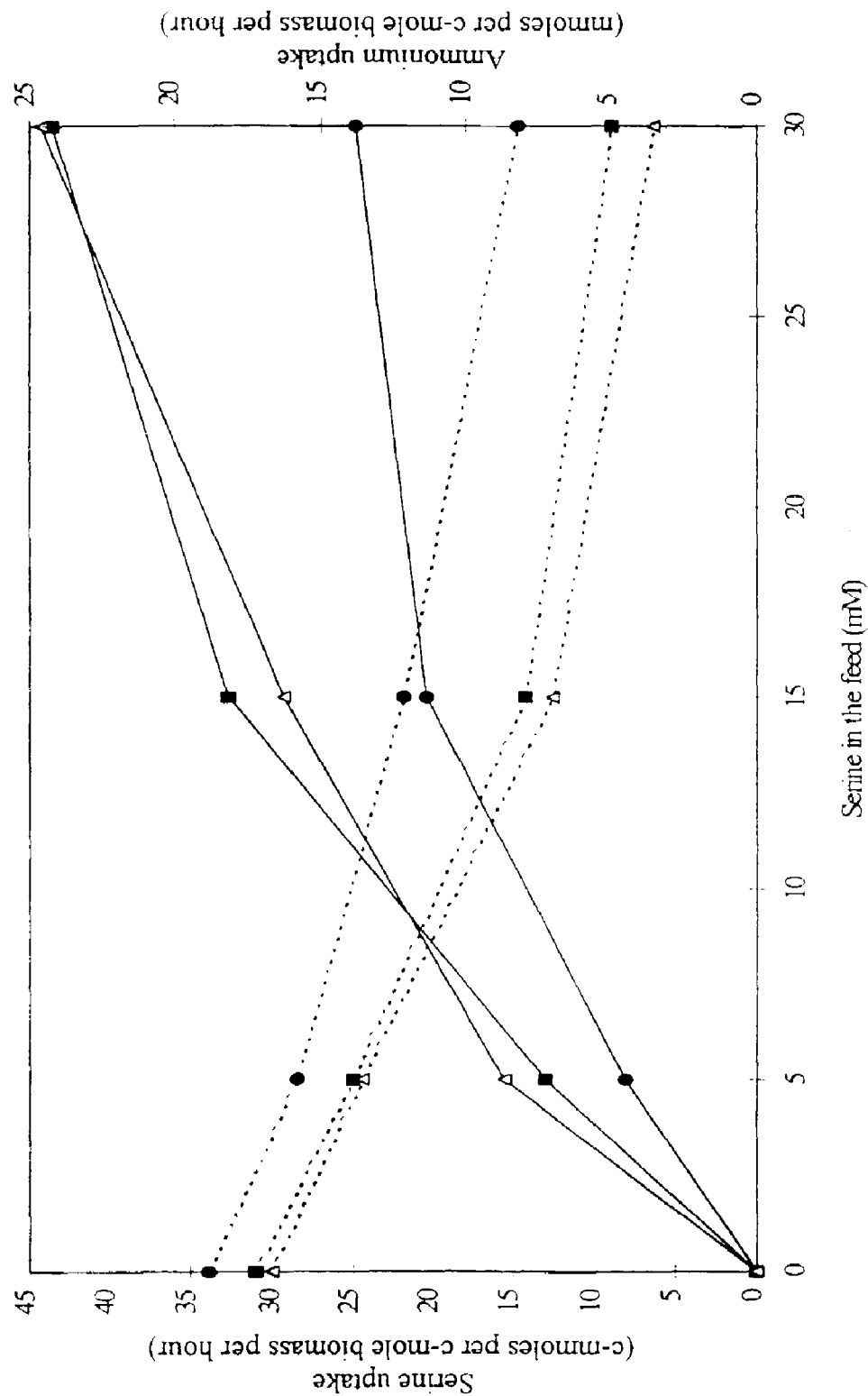

FIG. 4 shows the specific uptake rates of ammonium and serine in the continuous cultivations of strains TN1, TN9 and TN12 with increasing amounts of serine in the feed. Dotted lines: uptake of ammonium. Normal lines: uptake of serine. ●: TN1, ■: TN9, Δ: TN12.

Figure 5:
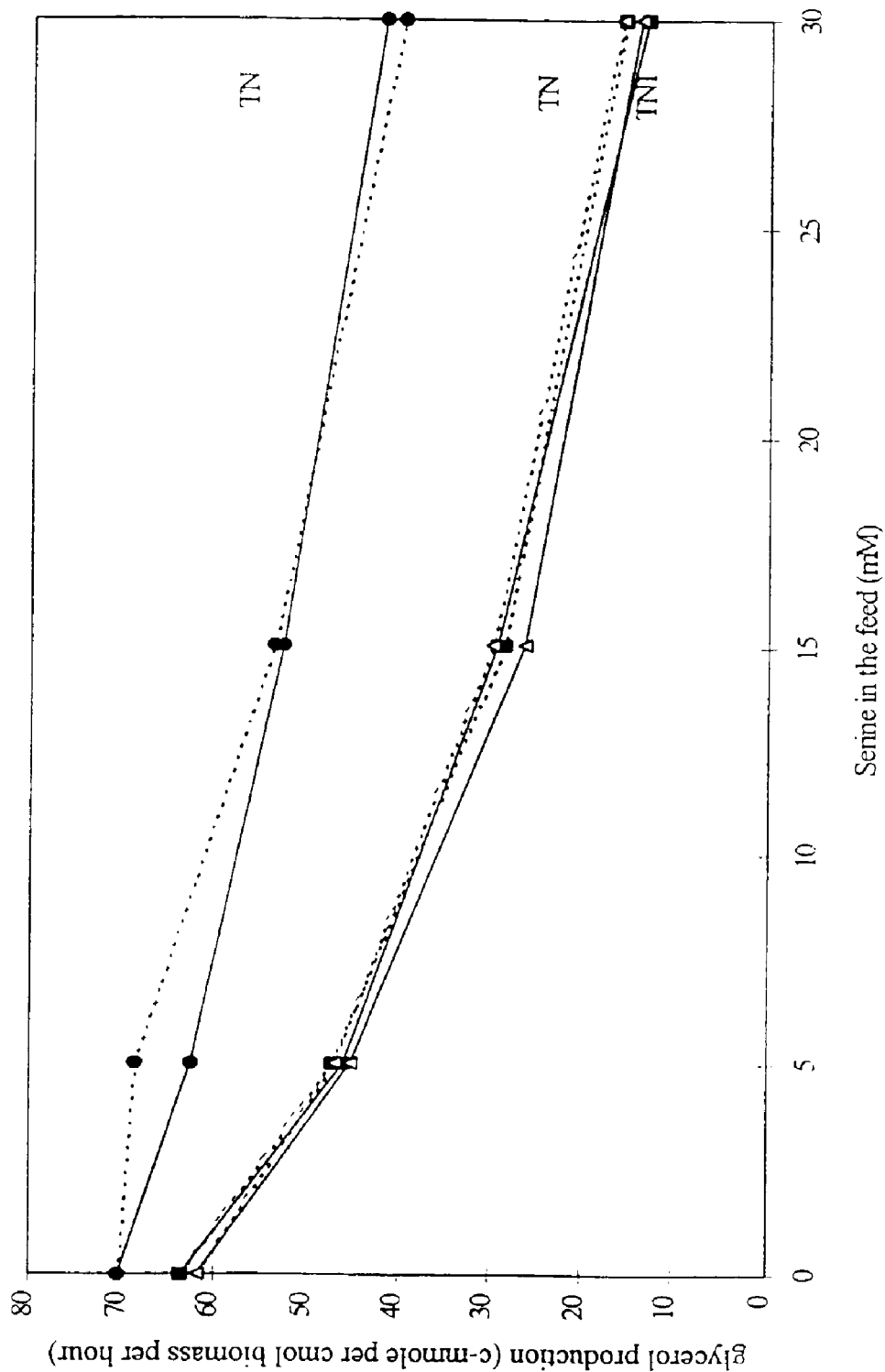

FIG. 5 shows the measured specific production rates of glycerol (normal lines) and the calculated specific production rates of glycerol (dotted lines) in the continuous cultivations of strains TN1, TN9 and TN12 with increasing amounts of serine in the feed. ●: TN1, ■: TN9, Δ: TN12.

Figure 6:
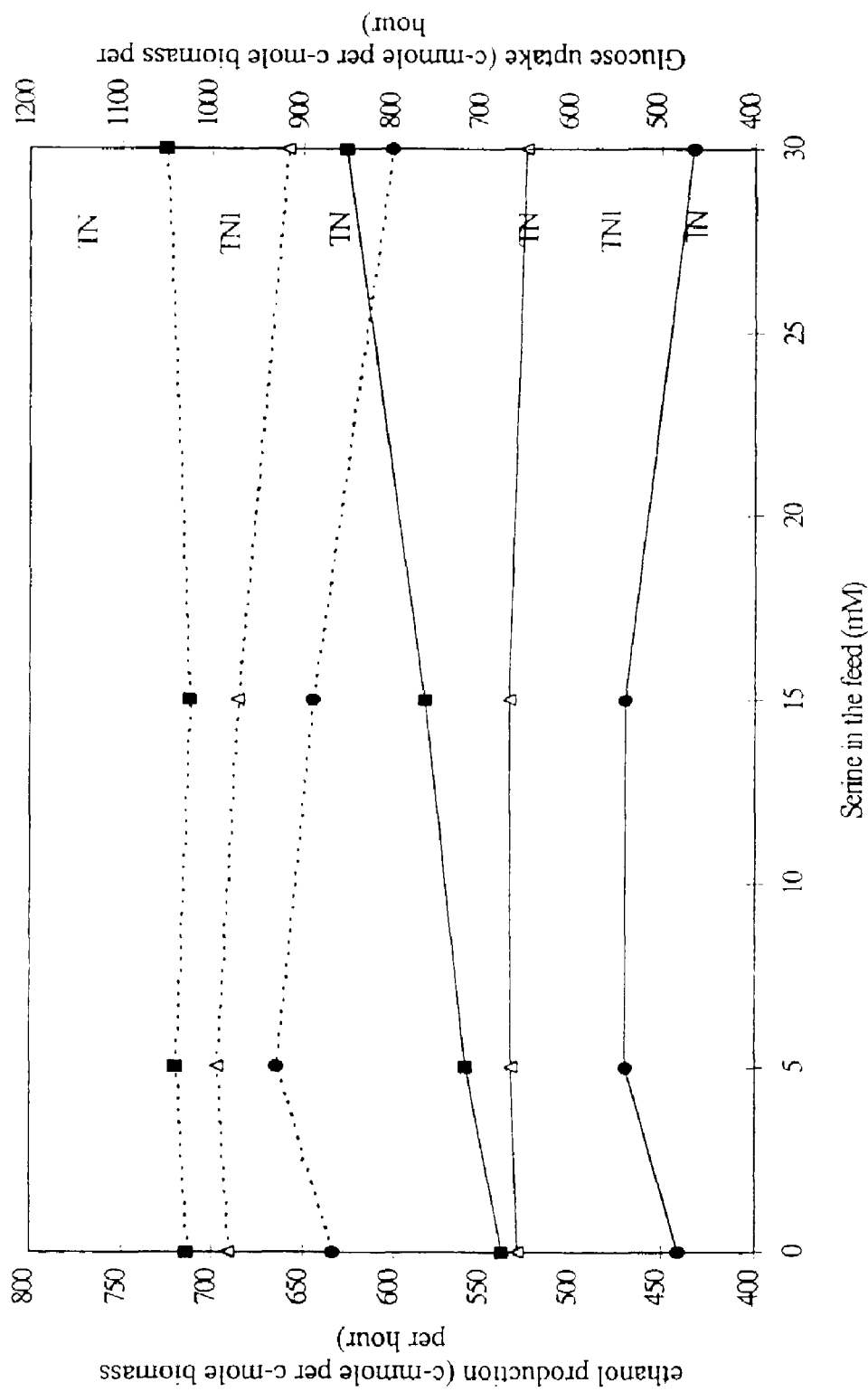

FIG. 6 shows the specific uptake rates of glucose (dotted lines) and the specific production rates of ethanol (normal lines) in the continuous cultivations of strains TN1, TN9 and TN12 with increasing amounts of serine in the feed. ●: TN1, ■: TN9, Δ: TN12.

Figure 7:
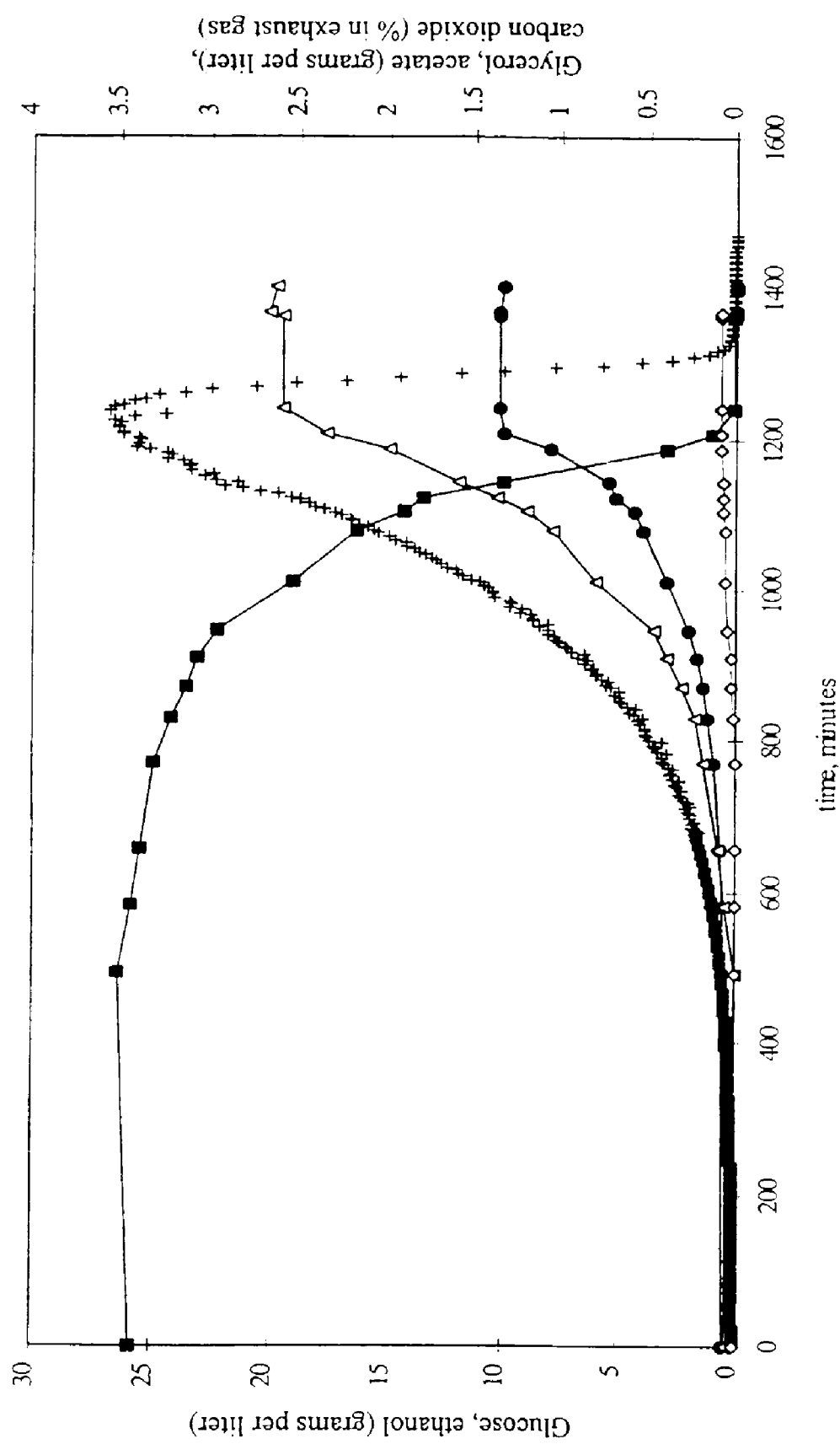

FIG. 7 shows the consumption of glucose (■), and production of ethanol (●), glycerol (Δ), acetate (◊) and carbon dioxide (X) versus time in one of the anaerobic, glucose-limited batch cultivations of strain TN1 with ammonium as nitrogen source.

Figure 8:
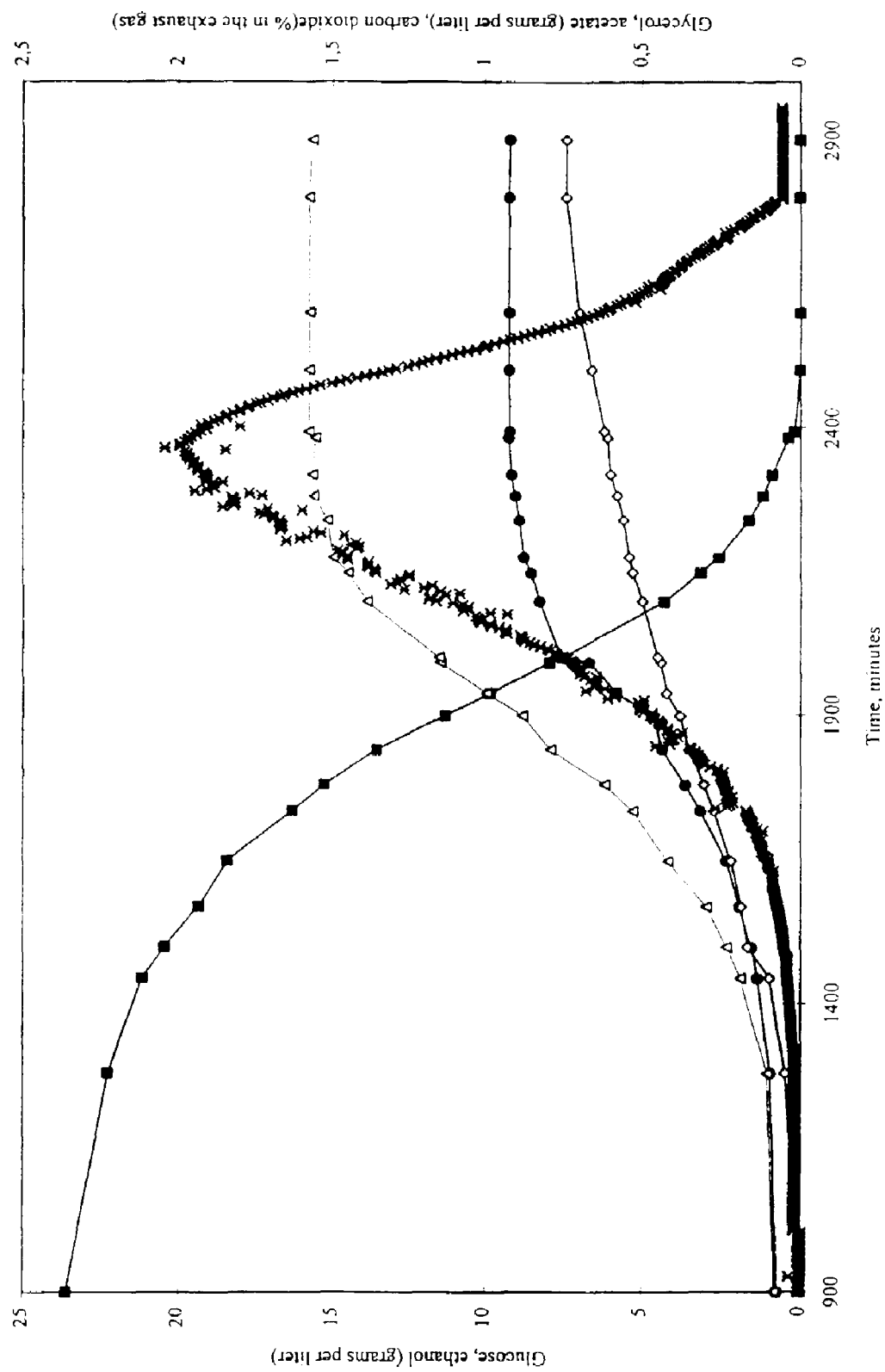

FIG. 8 shows the consumption of glucose (■), and production of ethanol (●), glycerol (Δ), acetate (◊) and carbon dioxide (X) versus time in one of the anaerobic, glucose-limited batch cultivations of strain TN1 with serine as nitrogen source.

Figure 9:
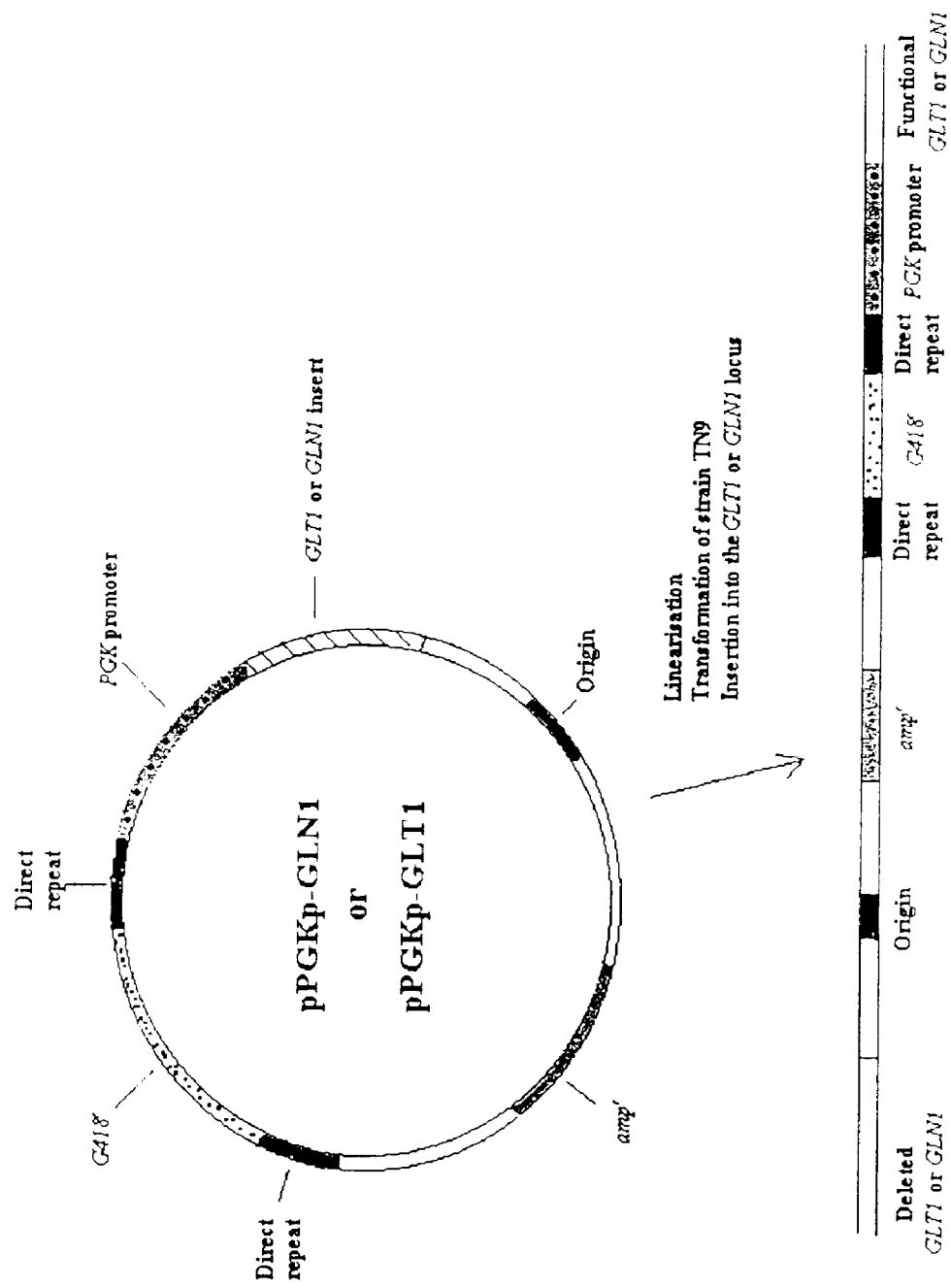

FIG. 9 shows plasmids pPGK-GLN1 and pPGK-GLT1 constructed in this study and used to integrate the strong constitutive promoter of PGK into the chromosome in front of GLN 1 and GLT1, respectively.

Figure 10:
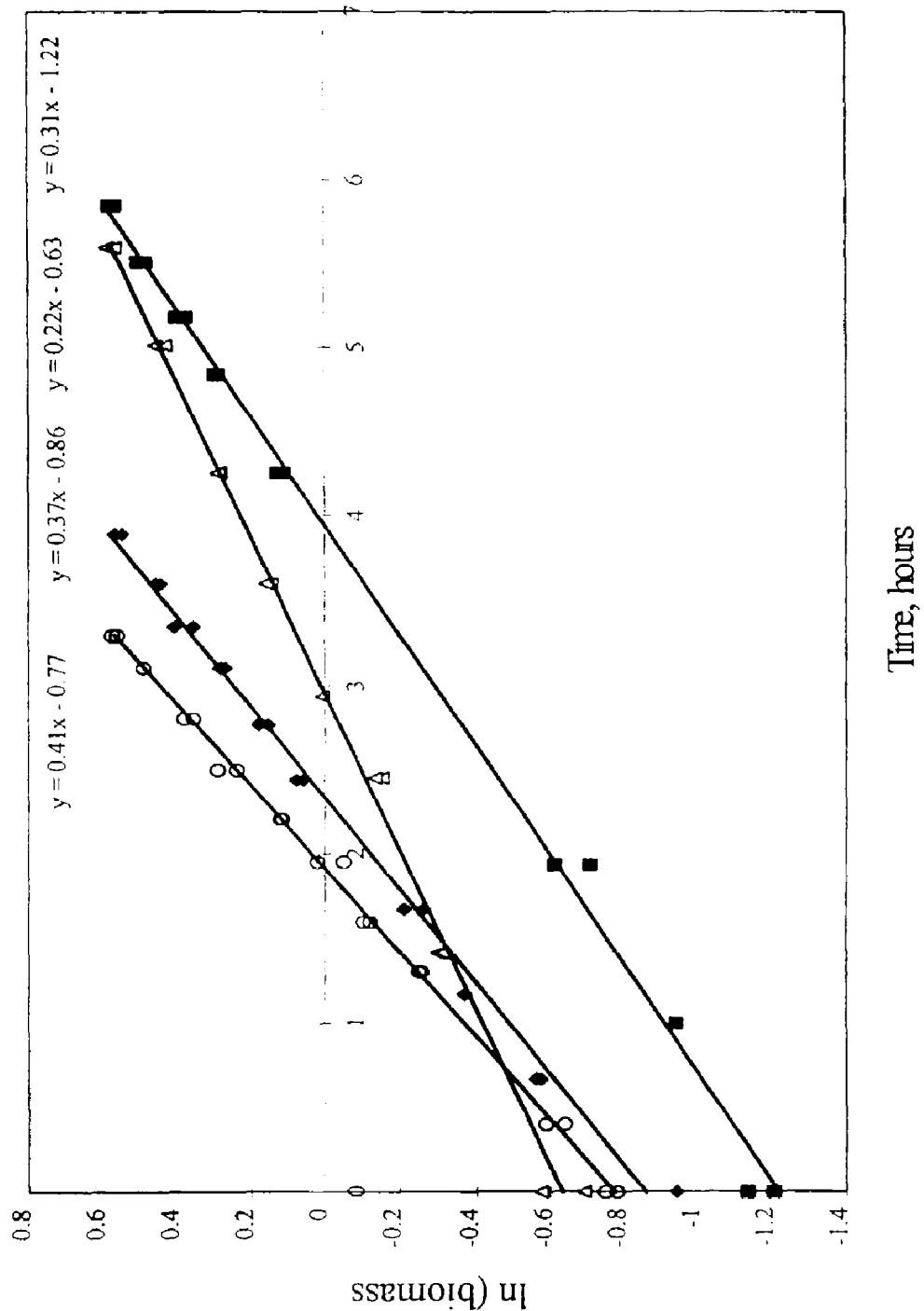

FIG. 10 shows the natural logarithm of the biomass concentrations of strains TN1 (○), TN9 (Δ), TN17 (■) and TN19 (♦) versus time during exponential growth in the anaerobic, glucose-limited batch cultivations. The equations show the slopes and intersections with the second axis of the trendlines through the measured values. The slopes are equal to the maximum specific growth rates of the strains.

Figure 11:
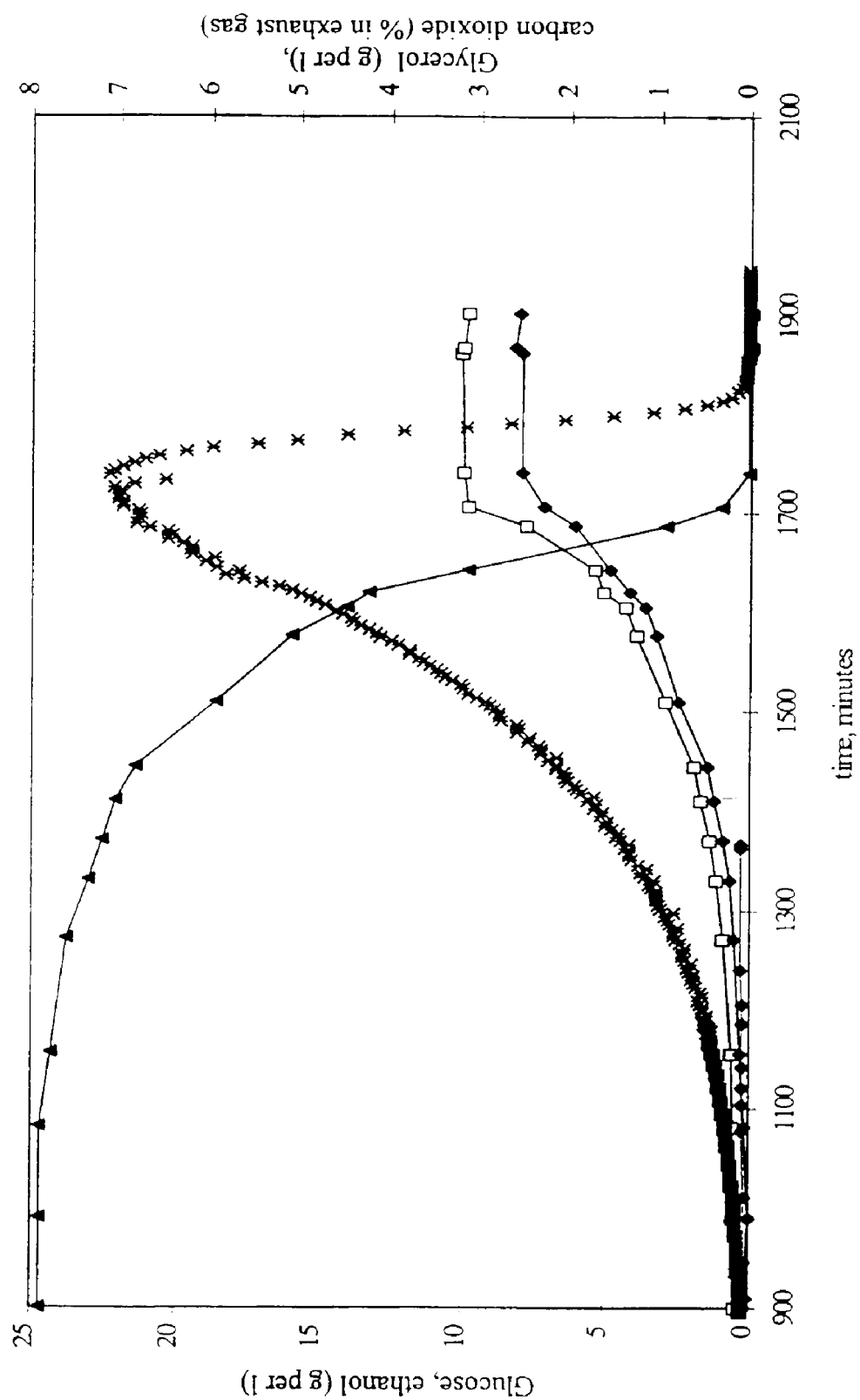

FIG. 11 shows the consumption of glucose (▲) and production of ethanol (□), glycerol (♦) and carbon dioxide (X) in one of the anaerobic batch cultivations of strain TN1.

Figure 12:
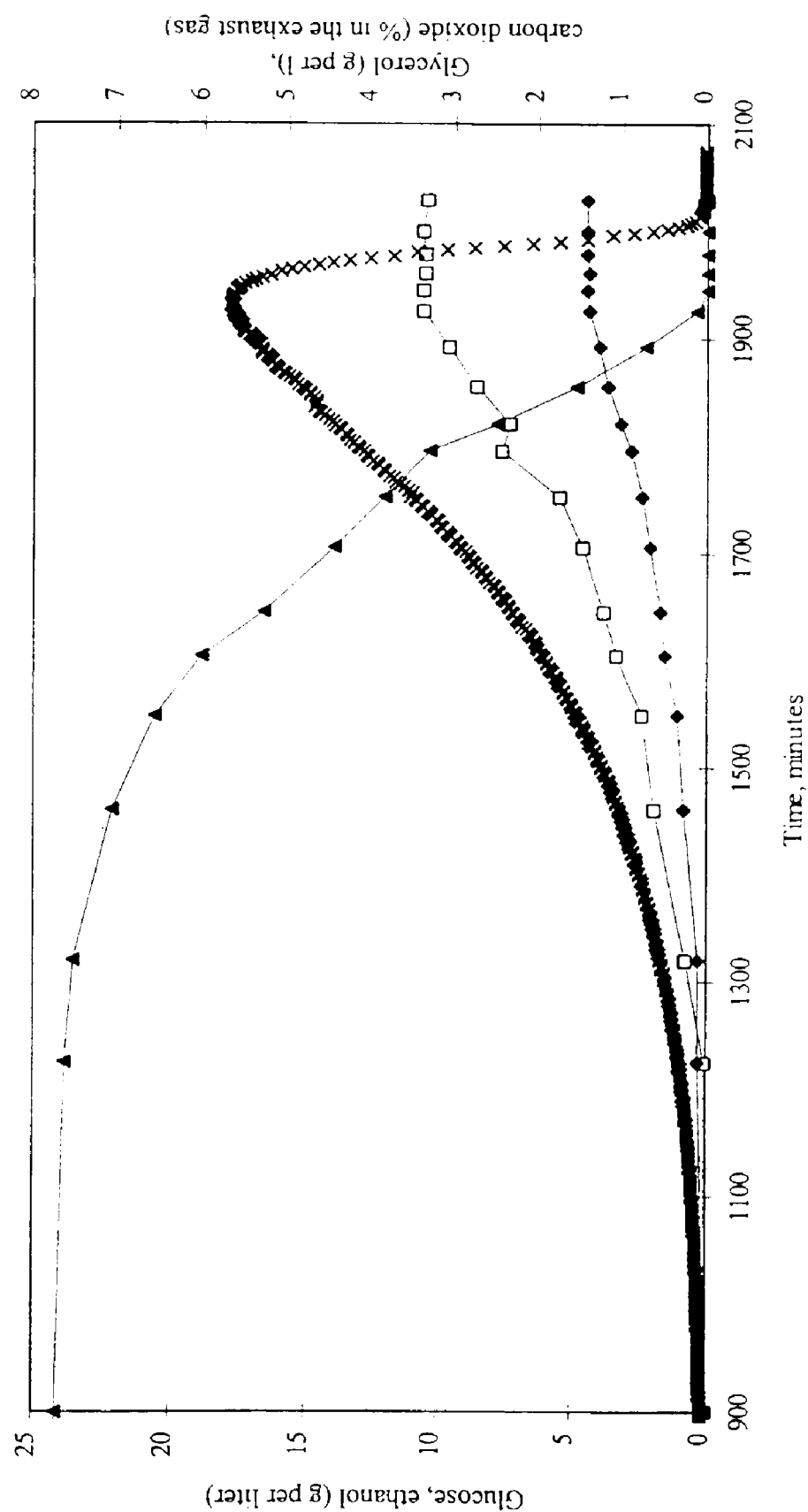

FIG. 12 shows the consumption of glucose (▲) and production of ethanol (□), glycerol (♦) and carbon dioxide (X) in one of the anaerobic batch cultivations of strain TN9.

Figure 13:
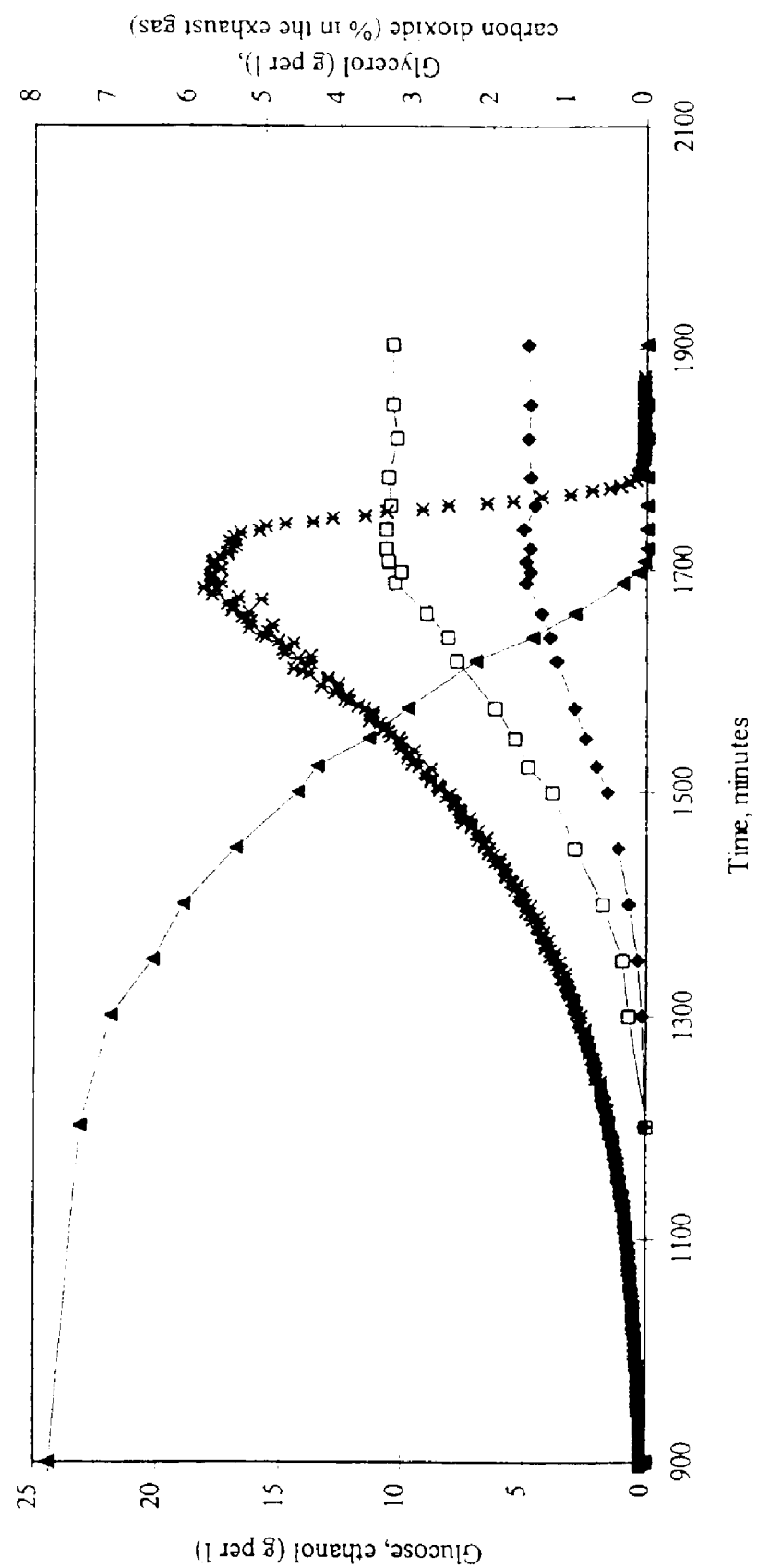

FIG. 13 shows the consumption of glucose (▲) and production of ethanol (□), glycerol (♦) and carbon dioxide (X) in one of the anaerobic batch cultivations of strain TN19.

EXAMPLE 1

Expression of NADH-dependent and NADPH-dependent Glutamate Dehydrogenase Activities in Yeast Introduction This example comprises a study of strains of *Saccharomyces cerevisiae* with a deletion in GDH1 and a concomitant constitutive or inducible overexpression of GDH2. The effect on growth rates, enzyme activities and product formation is reported. Batch and continuous cultivations of the novel genetically engineered strains were carried out in high performance bioreactors.

Materials and Methods

Microorganisms and their maintenance. All *Saccharomyces cerevisiae* strains were generated from *Saccharomyces cerevisiae* T23D. The strain was kindly provided by Jack Pronk from the Department of Microbiology and Enzymology, Kluyver Laboratory of Biotechnology, Delft University of Technology, The Netherlands. The yeast strains were maintained at 4° C. on YPG agar plates, monthly prepared from a lyophilised stock kept at −80° C. *Escherichia coli* DH5α (F$^-$F80dlacZ DM15 D(lacZYA-argF) U169 deoR recA1 endA1 hsdR17($r_k^-m_k^+$)supE44 i$^-$ $^{thi}$-1 gyra96 relA1) (GIBCO BRL, Gaithersburg, Md., USA) was used for subcloning.

Preparation of DNA. Plasmid DNA from *E. coli* was prepared with Qiagen columns (Qiagen GmbH, Dûsseldorf, Germany) following the manufacturer's instructions. For the purification of DNA fragments used for cloning experiments, the desired fragments were separated on 0.8% agarose gels, excised and recovered from agarose using the Qiagen DNA isolation kit (Qiagen GmbH, Dûsseldorf, Germany). Chromosomal DNA from *Saccharomyces cerevisiae* was extracted as follows. Cells were grown in medium in shake flasks and harvested at OD=1.5, 10 mg of wet cells were resuspended in 0.5 ml Tris-Cl (pH 8.0) and quenched with 0.5 ml glass beads (size 250–500 microns) in the presence of 0.5 ml Tris-saturated phenol (pH 8.0). The DNA was extracted from the phenol phase with chloroform, precipitated with 98% ethanol and resuspended in TE buffer. RNA in the extract was removed by treatment with RNAaseA (purchased from Promega) and finally the DNA was purified by precipitation with ethanol/lithium chloride and resuspended in TE buffer. The DNA primers were purchased from DNA Technology (Aarhus, Denmark).

Deletion of GDH1. Plasmid pGDH1del was kindly donated by professor F. K. Zimmermann (Boles et al., 1993). In pGDH1del a 1.0 kb fragment of GDH1 has been replaced by a 11.1 kb fragment containing the open reading frame of URA3. The construct was linearised with ClaI/PvuII prior to transformation. Correct deletion of GDH1 was verified by PCR analysis and by measurements of GDH1p activity in protein extracts from transformants. No NADPH-dependent glutamate dehydrogenase activity could be detected in correct transformants.

Figure 1:
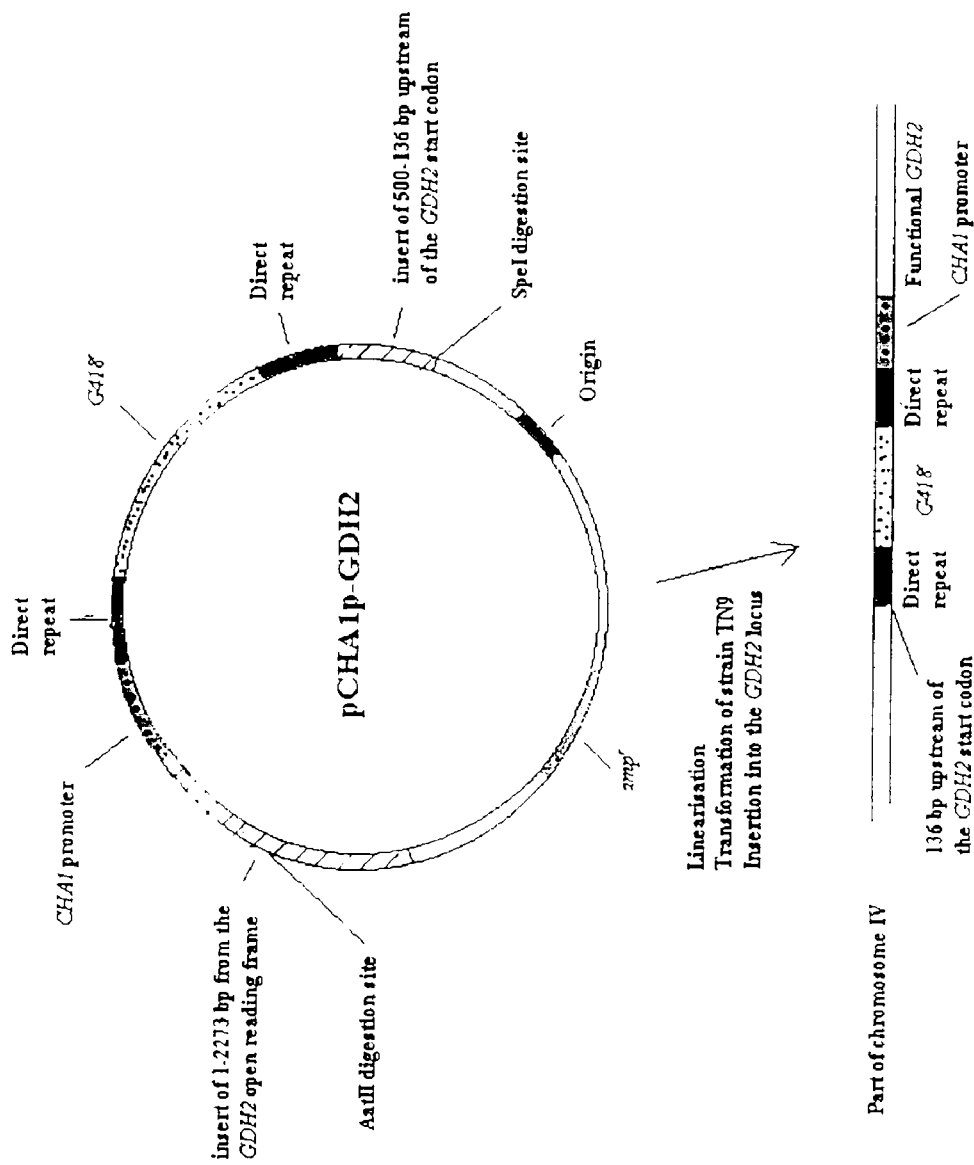
FIG. 1 shows plasmid pCHA 1-GDH2 integration into the GDH2 locus.

Overexpression of GDH2. The CHA1 promoter was cloned by PCR using pfu polymerase (New England Biolabs) and the primers CHA1 start (5'-ATT CAT CGA TGA ATT CTA TCT TAT GGT CCC ATT CTT TAC TGC ACT GTT TAC A-3'), SEQ ID NO:3, consisting of restriction enzyme sites for ClaI and EcoRI in front of nucleotides -364 to -329 upream of CHA1) and CHA1 stop (5'-GGC CAC TAG TGA TAT CAA AGC ATT CTC TCG CTG GTT AAT TTT CCT GTC TCT TGT CTA TCA GCA CTT AAA AA-3'), SEQ ID NO:4, consisting of restriction enzyme sites for SpeI, EcoRV and BsmI in front of nucleotides -1 to -45 upstream of CHA1). The resulting DNA fragment was isolated after gel electrophoresis on a 0.8% agarose gel and subcloned into the SmaI site in vector pUC19, resulting in plasmid pCHA1. The CHA1 promoter was isolated by from pCHA1 by digestion with BsmI and HineII (located in the multi-cloning site of pUC19). Plasmid YEpMSP3, containing the open reading frame of GDH2 (Boles et al., 1993), was kindly donated by Professor F. K. Zimmermann. The plasmid was digested with MscI and BsmI and ligated with the HincII/BsmI CHA1p fragment, resulting in a plasmid with insertion of the CHA1 promoter in front of the GDH2 start codon. This construct was digested with BamHI and a fragment, consisting of the CHA1 promoter and 2.27 kb of the open reading frame of GDH2, was isolated. Plasmid pFA6A-kanMX3 contains the geniticin resistance gene, G418', flanked by two direct repeats and two multi-cloning sites (Wach et al., 1994). A EcoRI/MscI DNA fragment, consisting of nucleotides -500 to -136 upstream of GDH2, was isolated from YEpMSP3 and inserted into pFA6A-kanMX3, digested with EcoRI and EcoRV. The resulting construct was linearised by digestion with BamHI and ligated with the 2.64 kb CHA1p-GDH2 fragment, resulting in plasmid pCHA1CGDH2 (FIG. 1). pCHA1GDH2 was linearised with SpeI/AatII prior to transformation. It was verified by PCR that the CHA1 promoter was inserted in front of the open reading frame of GDH2 on chromosome IV of correct transformants. For this purpose primers CHA1start and GDH2verif (5'-GGT TTT CTA CAA TCT CCA AAA GAG-3'), SEQ ID NO:5, spanning the region from nucleotides 1294 to 1271 of the GDH2 open reading frame.

Figure 2:
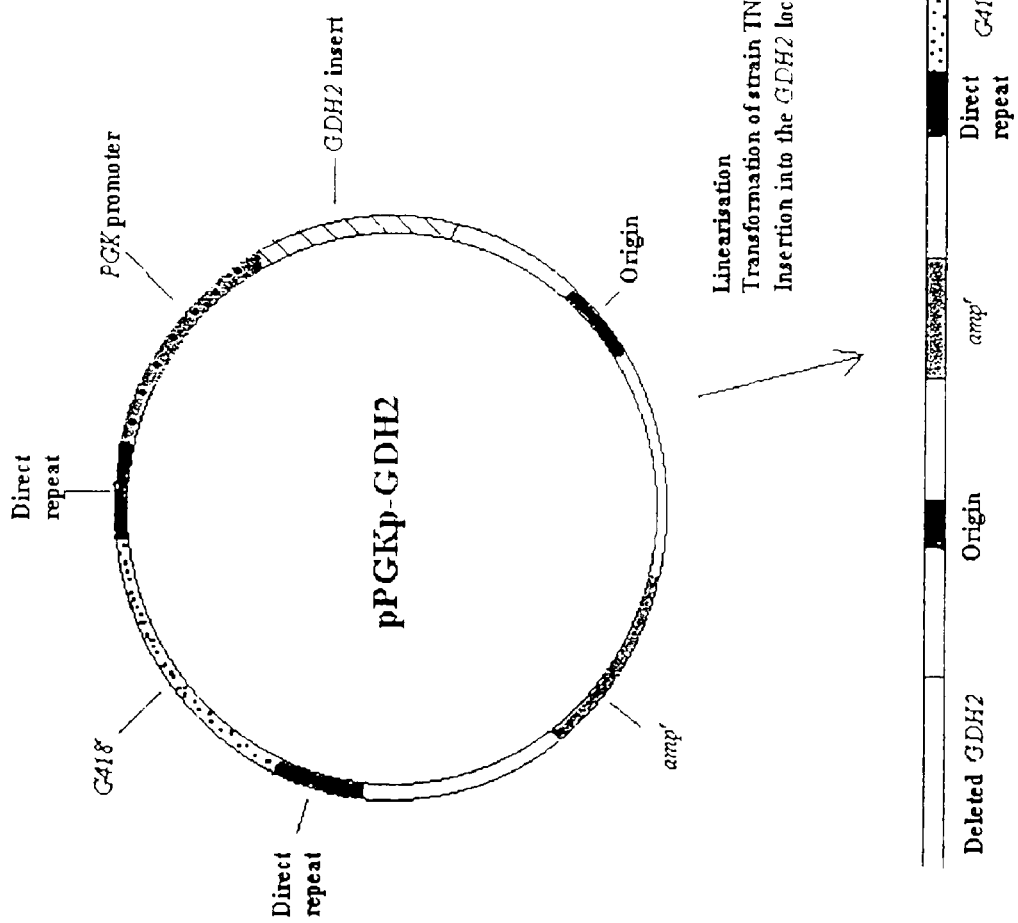
FIG. 2 shows plasmid pPGK-GDH2 integration into the GDH2 locus.

Primers Gdh2start (5'-GCG CGA GAT CTT CTA GAA TGC TTT TTG ATA ACA AAA AT-3'), SEQ ID NO:6, containing restriction enzyme sites for BglII and XbaI in front of nucleotides 1 to 21 of GDH2, and Gdh2stop (5'-CGC GCA GAT CTC CGC GGA GAG CCT AAA CGA TTA ACA AA-3'), SEQ ID NO:7, containing restriction enzyme sites for BglII and SacII in front of nucleotides 1221 to 1201 of GDH2, were used to clone parts of the structural gene of GDH2 by PCR with pfu polymerase (New England Biolabs). A DNA fragment of the correct size was isolated from a 0.8% agarose gel after electrophoresis and digested with BglII overnight. The fragment was ligated into the unique BglII digestion site of plasmid Yep24-pPGK behind the PGK promoter and in front of the PGK terminator (Walfridsson et al., 1997), resulting in plasmid Yep24-pPGK-GDH2. A 2.65 kb SmaI/SacII DNA fragment, consisting of the PGK promoter and the cloned part of GDH2 was isolated from Yep24-pPGK-GLT1. The fragment was ligated into plasmid pFA6A-kanMX3 (Wach et al., 1994), digested with EcoRV and SacII, resulting in plasmid pPGK-GDH2 (FIG. 2). The plasmid was linearised by digestion with TthIII1 prior to transformation. Correct insertion of the plasmid into the GDH2 locus on chromosome IV was verified by PCR analysis of chromosomal DNA extracted from transformants with resistance towards geniticin. For this purpose primers PGKverif (5'-GTC ACA CAA CAA GGT CCT A-3'), SEQ ID NO:8, spanning the region from nucleotides -420 to -400 upstream of the PGK start codon, and Gdh2verif (described above) were used.

Transformation of *E. coli* and *S. cerevisiae*. *E. coli* DH5α was transformed by electro-transformation using the Bio-Rad electroporation equipment (Biorad Laboratories. Richmond, USA). Transformants were selected on L broth plates containing 100 mg/ml ampicillin. *S. cerevisiae* cells were made competent for plasmid uptake by treatment with lithium acetate and polyethyleneglycol (Schiestl & Gietz, 1989). 5 µg of DNA was used for each transformation. Transformants were plated directly on selective media except for the G418 resistant transformants. These were suspended in YPD for 24 hours prior to plating on selective media in order to obtain expression of the G418 resistance gene. Correct integration of the fragments from pHOde1 and pSUC2 into the chromosome was verified by PCR analysis using extracted DNA from the transformants.

Medium in the batch and continuous cultivations. The strains of S. cerevisiae were cultivated in a mineral medium prepared according to Verduyn et al. (1990). Vitamins were added by sterile filtration following heat sterilisation of the medium. The concentrations of glucose and $(NH_4)_2SO_4$ initially in the batch cultivations were 25 g per l and 3.75 g per l, respectively. The concentration of glucose in the feed to the continuous cultivations was 25 g per l while the concentration of $(NH_4)_2SO_4$ was varied from 3.75 g per l to 0 g per l. The serine concentration in the feed was varied from 0 g per l to 3.16 g per l so that the sum of the ammonium and serine concentrations was 60 mM in all cultivations. Growth of S. cerevisiae under anaerobic conditions requires the supplementary addition to the medium of ergosterol and unsaturated fatty acids, typically in the form of Tween 80 (Andreasen & Stier, 1953; Libudzisz et al. 1986). Ergosterol and Tween 80 were dissolved in 96% (v/v) ethanol and the solution was autoclaved at 121° C. for 5 min. The final concentrations of ergosterol and Tween 80 in the medium were 4.2 mg per g DW and 175 mg per g DW, respectively. To prevent foaming 75 µl per l antifoam (Sigma A-5551) was added to the medium. The medium reservoir for the continuous cultivations was extensively sparged with $N_2$ containing less than 5 ppm $O_2$ after preparation and was then sealed. To avoid formation of a vacuum when withdrawing medium form the reservoir it was connected to a gas impermeable bag filled with $N_2$ containing less than 5 ppm $O_2$.

Experimental set-up for the batch and continuous cultivations. Anaerobic batch and continuous cultivations were performed at 30° C. and at a stirring speed of 800 rpm in in-house manufactured bioreactors. The working volume of the batch reactors and the continuous cultivation reactors were 4.5 liters and 1.0 liters, respectively. pH was kept constant at 5.00 by addition of 2 M KOH. The bioreactors were equipped with off-gas condensers cooled to 2° C. The bioreactors were continuously sparged with $N_2$ containing less than 5 ppm $O_2$, obtained by passing $N_2$ of a technical quality (AGA 3.8), containing less than 100 ppm 0, through a column (250×30 mm) filled with copper flakes and heated to 400° C. The column was regenerated daily by sparging it with $H_2$ (AGA 3.6). A mass flow controller (Bronkhorst HiTec F201C) was used to keep the gas flow into the bioreactors constant at 0.50 l nitrogen per min per liter Norprene tubing (Cole-Parmer Instruments) was used throughout in order to minimise diffusion of oxygen into the bioreactors. The bioreactors were inoculated to an initial biomass concentration of 1 mg per l with precultures grown in unbaffled shake flasks at 30° C. and 100 rpm for 24 hours. The anaerobic batch cultivations of strains TN1, TN9, TN12 and TN22 were each carried out three times with identical results. Steady state in the continuous cultivations was obtained after growth for 10–11 residence times. This was verified by measuring a constant formation of $CO_2$ and medium components, e.g. ethanol, glycerol and acetate, by the yeast throughout 2–3 residence times.

Determination of dry weight. Dry weight was determined gravimetrically using nitrocellulose filters (pore size 0.45 µm; Gelman Sciences). The filters were predried in a microwave oven (Moulinex FM B 935Q) for 10 min. A known volume of culture liquid was filtered and the filter was washed with an equal volume of demineralised water followed by drying in a microwave oven for 15 min. The relative standard deviation (RSD) of the determinations was less than 1.5% based on triple determinations (n=3).

Analysis of medium compounds. Cell-free samples were withdrawn directly from the bioreactor through a capillary connected to a 0.45 µm filter. Samples were subsequently stored at −40° C. Glucose, ethanol, glycerol, acetic acid, pyruvic acid, succinic acid and 2-oxoglutarate were determined by HPLC using an HPX-87H Aminex ion exclusion column (RSD<0.6%, n=3). The column was eluted at 60° C. with 5 mM $H_2SO_4$ at a flow rate of 0.6 ml per min. Pyruvic acid, acetic acid and 2-oxoglutarate were determined with a Waters 486 UV meter at 210 nm whereas the other compounds were determined with a Waters 410 refractive index detector. The two detectors were connected in series with the UV detector first. The $CO_2$ concentration in the off-gas was determined using a Brüel & Kjær 1308 acoustic gas analyser (RSD=0.02%) (Christensen et al, 1995). Ammonium was determined using a commercially available assay (Boehringer Mannheim Cat. No. 1 112 732). Serine was determined as described by Barkholt and Jensen, 1989. In a separate experiment the off gas from the bioreactor was bubbled through liquid nitrogen and the ethanol concentration in the frozen mixture of water, ethanol and acetaldehyde was determined by HPLC after evaporation of the $N_2$. Hereby the loss of ethanol through the reflux condenser of the bioreactor was determined to be between 4% and 9% of the ethanol formed by the bioreaction depending on the dilution rate (Schulze, 1995). In the carbon balances the measured ethanol fluxes were corrected for this loss through evaporation.

Measurement of enzyme activities. Culture liquid was withdrawn from the bioreactor into an ice cooled beaker, centrifuged and washed twice with 10 mM potassium phosphate buffer (pH 7.5, 2° C.) containing 2 mM EDTA. Subsequently the cells were resuspended in 4.2 ml 100 mM potassium phosphate buffer (pH 7.5, 2° C.) containing 2 mM $MgCl_2$ followed by immediate freezing in liquid nitrogen and storage at −40° C. Prior to analysis 0.22 ml of 20 mM DTT was added to the samples whereafter they were distributed into precooled 2 ml eppendorf tubes containing 0.75 ml glass beads (size 0.25–0.50). The cells were disrupted in a bead mill for 12.5 min. (0° C.). The test tubes were centrifuged (20000 rpm, 20 min., 0° C.) whereafter the supernatants were pooled in one test tube. During the following analyses the extract was kept on ice. Enzyme assays were performed at 30° C. using a Shimadzu UV-260 spectrophotometer at 30° C. Reaction rates, corrected for endogenous rates, were proportional to the amount of extract added. All enzyme activities are expressed as micromole of substrate converted per minute per mg total cellular protein as determined by the Lowry method. Glutamate dehydrogenase ($NAD^+$ and $NADP^+$) (EC 1.4.1.5 and EC 1.4.1.4, respectively) were assayed as described by Bruinenberg et al. (1983a). Glutamate synthase (GOGAT) (EC 1.4.1.14) was assayed as described by Holmes et al. (1989).

Results

Construction of strains with a deletion in GDH1 and an overexpression of GDH2. The object of the study was to analyse whether the NADH-dependent glutamate dehydrogenase, encoded by GDH2, could substitute the NADPH-dependent isoenzyme, encoded by GDH1, in assimilation of ammonium and 2-oxoglutarate into glutamate in *S. cerevisiae*. This should lead to a reduction in surplus formation of NADH in biomass synthesis and thus, to a *S. cerevisiae* strain with a reduced formation of glycerol and possibly an increased formation of ethanol. To obtain this, strain were constructed with a deletion in GDH1 and an overexpression of GDH2. GDH1 was deleted as described earlier (Boles et al., 1993) in the haploid strain TN2 derived from *S. cerevisiae* CBS8066 (Nissen et al., 1998). The resulting strain was denounced TN9. In order to obtain a strain with a stable, constitutive overexpression of GDH2, the promoter of PGK, encoding phosphoglycerate kinase, was inserted in front of the start codon of GDH2 on chromosome IV. PGK encodes one of the most abundant mRNA and protein species in the cell, accounting for 1% to 5% of the total cellular mRNA and protein during growth on fermentative carbon sources (Dobson et al. 1982). Insertion of the promoter was obtained by homologue recombination of a 4.8 kbp SpeI/xxx fragment from pPGKGDH2 into the GDH2 locus in strain TN9 (see materials and methods). The resulting strain was denounced TN22. The promoter of CHA1, encoding the catabolic L-serine dehydratase, has been reported to be inducible by low amounts of serine (Bornæs et al., 1993). To study to effect of varying levels of Gdh2p activity in a strain background with no activity of Gdh1p, the CHA1 promoter was inserted into chromosome IV in front of the open reading frame of GDH2 in strain TN9. The serine inducible promoter was chosen to avoid the use of inducible promoters that were dependent on addition of a second carbon source besides glucose since this would complicate the comparison between cultivations with increasing concentrations of this second carbon source. Furthermore, the CHA1 promoter was reported to be induced up to 130 times by addition of 5 mM serine, which would have very little influence on the cell physiology. The insertion of the CHA1 promoter was obtained by homologue recombination of a 4.3 kbp SpeI/AatII fragment from pCHA1GDH2 into the GDH2 locus in strain TN9 (see materials an methods). The resulting strain was denounced TN12.

Continuous cultivations. Physiological studies of the genetically engineered strains were carried out in anaerobic continuous cultivations. Strain TN12 with the inducible CHA1 promoter inserted into the chromosome in front of GDH2 was cultivated until steady states had been achieved in growth media containing glucose as the primary carbon source and increasing amounts of serine from 0 mM to 30 mM. The amount of ammonium sulphate in the feed was regulated to give a final concentration of 60 mM ammonium and serine. This was done to study the degree of GDH2 induction that could be achieved with the new promoter and the effect of this induction on product formation. Similar cultivations of strains TN1 and TN9 were performed. Hereby, the effects of the increasing amounts of serine in the feed, the deletion of GDH1, and the insertion of the new promoter in front of GDH2 on the product formation could be discriminated from each other.

The specific activities of Gdh1p, Gdh2p and Glt1p were measured in vitro in cell extracts from each steady-state cultivation. The activity of Gdh1p in TN1 decreased almost linear from 0.657 to 0.475 units per mg total cellular protein (Upper mg TCP) when the serine content in the feed was increased from 0 mM to 30 mM (dotted line in FIG. 3). This fitted well with the measured decrease in ammonium uptake from 18.8 to 8.2 mmoles per c-mole biomass per hour, respectively. Earlier studies of *S. cerevisiae* have shown that a decrease in ammonium uptake results in a simultaneous reduction in Gdh1p activity in cell free extracts (ter Schure et al., 1995a). No activity of the NADPH-dependent glutamate dehydrogenase could be detected in cell free extracts from any of the continuous cultivations of TN9 and TN12. The Gdh2p activity in cell free extracts of strain TN1 increased from 0.007 Upper mg TCP when ammonium was used as the sole nitrogen source to 0.022 Upper mg TCP when 30 mM serine was present in the feed (FIG. 3). Deletion of GDH1 in TN9 resulted in a marked increase in the specific activity of Gdh2p. When ammonium was used as the sole nitrogen source the activity was determined to 0.268 Upper mg TCP, an increase of a factor 40 as compared to the activity in TN1. It has been shown that the intracellular level of glutamine results in strong repression of GDH2 expression at the transcriptional level (Miller and Magasanik, 1991). When GDH1 is deleted the synthesis of glutamate from 2-oxoglutarate and ammonium is strongly affected which probably leads to a significant decrease in the intracellular concentration of the component. Since glutamate is one of the substrates in glutamine synthesis this will result in a further decrease in the intracellular level of the amino acid. Thus, the strong increase in Gdh2p in TN9 probably was due to an elevation of glutamine repression of GDH2. Addition of increasing amounts of serine to the feed resulted in a significant reduction in the Gdh2p activity. Since the residual glucose concentrations in all cultivations of TN9 was constant at 20 c-mmoles per liter this was not due to glucose repression of GDH2 (Coschigano et al., 1991). The residual concentration of ammonium decreased from 48 mM when the compound was used as the sole nitrogen source to 28 mM when 30 mM serine was added to the medium. In an earlier study in continuous cultivations of a wild-type *S. cerevisiae* it was demonstrated that the Gdh2p activity decreased by a factor 4 when the residual ammonium concentration was reduced by this amount (ter Schure et al., 1995b). Since the intracellular glutamine concentration decreased simultaneously, this effect was not due to repression from this component. Instead, an observed increase in the intracellular concentration of 2-oxoglutarate might explain the reduction in Gdh2p activity since this component generally is thought to be the product of the reaction catalysed by the enzyme when the cells are cultivated on nitrogen sources other than ammonium. No increase in the specific activity of Gdh2p was observed in the cultivation of TN12 with ammonium as the sole nitrogen source. This clearly demonstrated that the increase of Gdh2p activity observed under these growth conditions in TN9 was due to deregulation of the GDH2 promoter. The expected induction of the CHA1 promoter by serine was not observed in the cultivations of TN12 when increasing amounts of the component was added to the feed. The presence of 5 mM serine in the medium increased the Gdh2p activity by a factor of 6 while the maximum induction was observed by addition of 30 mM serine. Here the activity of the enzyme was 13 times higher than when ammonium was used as nitrogen source. No mutations in the cloned region of the CHA1 promoter was found when the obtained PCR fragment was sequenced. As mentioned above earlier studies have shown that the promoter is induced 130 times at the transcriptional level by the presence of 5 mM serine in the growth medium. Thus, the absence of this induction in TN12 must be due to post-transcriptional regulation of the enzyme. No significant difference in the specific activity of glutamate dehydrogenase could be detected when steady states cultivations with increasing amounts of serine in the feed of the same strain were compared or when steady state cultivations of TN1, TN9 and TN12 were compared. The level of the specific activity ranged from 0.008–0.013 Upper mg TCP.

The uptake of glucose, ammonium and serine and the production of ethanol, glycerol, biomass, carbon dioxide, succinate, pyruvate and acetate by the three strains were measured at each steady state. From these measurements the product yields (in c-moles product produced per c-moles glucose and serine consumed) were calculated (Tables 1–3).

TABLE 1

| Ammonium in the feed, mM | 60 | 55 | 45 | 30 |
|---|---|---|---|---|
| Serine in the feed, mM | 0 | 5 | 15 | 30 |
| Ethanol | 0.491 | 0.503 | 0.518 | 0.523 |
| Glycerol | 0.078 | 0.067 | 0.058 | 0.050 |
| Pyruvate | 0.003 | 0.001 | 0.002 | 0.002 |
| Acetate | 0.001 | 0.003 | 0.001 | 0.002 |
| Succinate | 0.003 | 0.003 | 0.003 | 0.004 |
| Carbon dioxide | 0.239 | 0.232 | 0.233 | 0.248 |
| Biomass | 0.141 | 0.131 | 0.137 | 0.152 |
| Total | 0.956 | 0.940 | 0.952 | 0.981 |

Table 1. Product yields in the continuous cultivations of strain TN1 with increasing amounts of serine in the feed. Unit: c-moles product per c-moles of glucose and serine consumed.

TABLE 2

| Ammonium in the feed, mM | 60 | 55 | 45 | 30 |
|---|---|---|---|---|
| Serine in the feed, mM | 0 | 5 | 15 | 30 |
| Ethanol | 0.525 | 0.532 | 0.550 | 0.572 |
| Glycerol | 0.062 | 0.044 | 0.028 | 0.012 |
| Pyruvate | 0.004 | 0.003 | 0.002 | 0.003 |
| Acetate | 0.000 | 0.000 | 0.000 | 0.000 |
| Succinate | 0.003 | 0.004 | 0.003 | 0.004 |
| Carbon dioxide | 0.257 | 0.267 | 0.274 | 0.274 |
| Biomass | 0.123 | 0.122 | 0.124 | 0.106 |
| Total | 0.974 | 0.972 | 0.981 | 0.971 |

Table 2. Product yields in the continuous cultivations of strain TN9 with increasing amounts of serine in the feed. Unit: c-moles product per c-moles of glucose and serine consumed.

TABLE 3

| Strain | TN12 | | | | TN22 |
|---|---|---|---|---|---|
| Ammonium in the feed, mM | 60 | 55 | 45 | 30 | 60 |
| Serine in the feed, mM | 0 | 5 | 15 | 30 | 0 |
| Ethanol | 0.500 | 0.529 | 0.534 | 0.546 | 0.516 |
| Glycerol | 0.061 | 0.045 | 0.026 | 0.014 | 0.030 |
| Pyruvate | 0.002 | 0.002 | 0.001 | 0.001 | 0.002 |
| Acetate | 0.004 | 0.004 | 0.004 | 0.004 | 0.004 |
| Succinate | 0.003 | 0.003 | 0.003 | 0.004 | 0.004 |
| Carbon dioxide | 0.247 | 0.279 | 0.250 | 0.265 | 0.255 |
| Biomass | 0.125 | 0.128 | 0.130 | 0.138 | 0.138 |
| Total | 0.942 | 0.990 | 0.948 | 0.972 | 0.949 |

Table 3. Product yields in the continuous cultivations of strain TN12 with increasing amounts of serine in the feed and in the continuous cultivation of strain TN22 with ammonium as the sole nitrogen source.
Unit in the cultivations of TN12: c-moles product per c-moles of glucose and serine consumed. Unit in the cultivation of TN22: c-moles product per c-mole glucose consumed.

Carbon balances of the products yields in the 12 steady state cultivations showed that 95%–98% of the consumed carbon was converted into one of the listed products. The degree of reduction of the remaining 2%–5% of the consumed carbon varied between 0 and 1, indicating that the production of carbon dioxide was measured to low.

Ammonium and serine were consumed simultaneously by the three strains (FIG. 3). Thus, the presence of both nitrogen sources in the growth medium did not result in repression of the specific uptake systems of the two components. The increasing amounts of serine added to the feed resulted in an increase in the specific uptake of the compound. A model based on simple Michaelis Menten type kinetics, describing the dependence of the uptake on the extracellular serine concentration, did not fit the measurements (results not shown). Thus, other components, e.g. glucose, probably had a regulatory effect on the specific uptake of the compound. The need for nitrogen uptake in the form of ammonium decreased when increasing amounts of serine were consumed by the cells. This resulted in a reduction in the specific ammonium uptake in the cultivations (FIG. 4). The total specific uptake of nitrogen was calculated from the measurements of the ammonium and serine uptake to be constant at 17–18 mmoles nitrogen per c-mole biomass per hour in all 12 steady state continuous cultivations. This indicated a constant composition of the biomass with respect to the content of protein, RNA, DNA and carbohydrates.

Addition of serine to the medium resulted in a decrease in the specific glycerol production (FIG. 5). The serine addition reduces the cells need for de novo synthesis of the amino acid. Synthesis of one mole serine from glucose and ammonium involves the reduction of two moles $NAD^+$ to NADH and a deamination step where one mole glutamate is converted to 2-oxoglutarate. As described earlier glutamate can be regenerated from 2-oxoglutarate by either two isoenzymes of glutamate dehydrogenase, encoded by GDH1 and GDH2, under consumption of NADPH or NADH, respectively. Furthermore, glutamate can be synthesised from 2-oxoglutarate and glutamine by glutamate synthase, encoded by GLT1, under consumption of NADH (Cogoni et al., 1995). In strain TN1 all three enzymes are present while only Gdh2p and Glt1p are active in strains TN9 and TN12. Thus, addition of serine results in a reduction of surplus NADH formation of either 1 or 2 moles per mole serine in TN1 and 1 mole per mole serine in TN9 and TN12. De novo synthesis of serine in S. cerevisiae CBS8066 was calculated to 157 c-mmoles per c-mol biomass based on measurements of the content of serine and the amino acids synthesised from serine in the protein pool (Schulze, 1995). By assuming this to be similar in TN1, TN9 and TN12 the specific serine synthesis during growth on ammonium as the sole nitrogen source was 19.9 c-mmoles per c-mole biomass per hour. In the cultivations with 15 mM and 30 mM serine in the feed the specific serine uptake exceeded this value (FIG. 4). Thus, in these cultivations serine was also catabolised by the cells. As mentioned above L-serine dehydratase, encoded by CHA1, catalyses deamination of serine to pyruvate and ammonium. No increase in the secretion of pyruvate, acetate or metabolites in the tricarboxylic cycle was measured when increasing amounts of serine was added to the feed. Hence, pyruvate stemming from the deamination reaction was converted into acetaldehyde and further into ethanol under consumption of one mole NADH per mole serine. These two effects of serine addition to the medium on the reduction of surplus NADH formation resulted in the observed decrease in the specific glycerol production. This was quantified by extracting the reduction in surplus NADH formation due to serine addition from the value of the specific glycerol production measured in the continuous cultivations with ammonium as the sole nitrogen source (dotted lines in FIG. 5). In all calculations a value for the reduction in surplus NADH formation of 1 mole per mole of serine was used. The reduction in the specific glycerol formation of strains TN9 and TN12 when cultivated in media with increasing amounts of serine in the feed could be accounted for by the two effects of serine addition on surplus NADH formation since the calculated values were close to equal with the measured values. For strain TN1 the calculated specific glycerol production was equal to the measured values in the cultivations with 15 mM and 30 mM serine in the feed. In the cultivation with 5 mM serine in the feed a correct value for the specific glycerol formation could only be calculated by assuming a reduction in surplus NADH formation of 2 moles per mole serine. Hereby a specific glycerol production of 61.2 c-mmoles per c-mole biomass per hour was obtained as compared to 68.6 c-mmoles per c-mole biomass per hour when a value for the reduction in surplus NADH formation of 1 mole per mole of serine was used. This indicates that Gdh1p catalyses the regeneration of glutamate from 2-oxoglutarate when the serine uptake is low while Gdh2p catalyses the reaction with increasing levels of the amino acid. Earlier studies support this observation since it has been shown that Gdh1p catalyses the formation of glutamate during growth on ammonium as the sole nitrogen source while Gdh2p catalyses the interconversion of glutamate and 2-oxoglutarate during growth on other nitrogen sources (Courchesne and Magasanik 1988: Miller and Magasanik, 1990). The calculations clearly demonstrated the significant effect of serine addition on the cell physiology but also that formation of surplus NADH in the synthesis of biomass has a high control on glycerol formation. Furthermore, they demonstrated that the decrease in the specific glycerol production was independent of the specific activity of Gdh2p.

The specific ethanol production was also affected by addition of serine to the feed (FIG. 6). In the cultivations of TN1 the specific ethanol formation reached a maximum when 5 mM and 15 mM serine was added to the feed and then decreased slightly when the serine content was increased to 30 mM. In the cultivations of TN9 the specific ethanol production increased almost linearly from 540 to 626 c-mmoles per c-mole biomass per hour while it was constant in the cultivations of TN12. Serine addition has at least four potential influences on ethanol formation in *S. cerevisiae*. The cellular consumption of ATP is to a given extent affected by the increase in active uptake of serine, by the decrease in active uptake of ammonium and by the reduction in glycerol formation since glycerol synthesis involves consumption of one ATP per molecule. Since ATP is formed through synthesis of ethanol during anaerobic growth these effects will change the specific ethanol formation. Furthermore, as described above serine was catabolised to ethanol in some of the cultivations. The effects of serine addition on ethanol synthesis were quantified by assuming ATP consumption in the active uptake systems of serine and ammonium of one ATP per molecule. The calculated changes in ethanol formation due to the four effects was then used to calculate values for the specific ethanol formation with increasing amounts of serine in the feed from the value measured when ammonium was used as the sole nitrogen source. An increase in the specific ethanol production from 540 to 544 c-mmoles per c-mole biomass per hour and from 531 to 536 c-moles per c-mole biomass per hour was calculated for strains TN9 and TN12, respectively. For TN1 the calculated specific ethanol production decreased from 441 to 435 c-mmoles per c-mole biomass per hour. Thus, the listed direct effects of serine addition on ATP consumption and ethanol synthesis could not explain the changes in the specific ethanol production. Instead, the changes could be due to a switch in the metabolism leading to an increased ATP consumption in biomass synthesis. It has been shown in an earlier study that only glutamate synthase catalyses the formation of glutamate when GDH1 is deleted (Miller and Magasanik, 1990). Thus, a strain with a double deletion in GDH1 and GLT1 grew poorly on ammonium as the sole nitrogen source. In the study a growth medium containing high levels of glucose was used and hence, Gdh2p activity in the double mutant was repressed. By overexpressing GDH2 in the mutant a specific activity of the gene product of 0.195 units per mg TCP was obtained which led to an increase in the growth rate on ammonium to wild-type levels. In the continuous cultivation of strain TN9, carrying the deletion in GDH1, with ammonium as the sole nitrogen source the specific Gdh2p activity was 0.268 units per mg TCP due to absence of glucose repression. This strongly indicated that glutamate was synthesised by both glutamate synthase and the NADH-dependent glutamate dehydrogenase under these growth conditions. When the serine content in the medium was increased the specific Gdh2p activity decreased. Since the specific growth rate was kept constant at $0.127$ $h^{-1}$ it is reasonable to assume that also the cellular glutamate synthesis rate was constant with increasing amounts of serine in the feed. Thus, increasing amounts of the component probably was synthesised through the reaction catalysed by glutamate synthase. Here 2-oxoglutarate and glutamine is converted into two molecules of glutamate under consumption of NADH. Glutamine is then regenerated from glutamate under consumption of ammonium and ATP catalysed by glutamine synthetase. In the net reaction catalysed by the two enzymes 2-oxoglutarate and ammonium are converted into glutamate under consumption of NADH and ATP which results in an increase in ATP consumption in biomass synthesis compared to glutamate synthesis catalysed by Gdh2p. Overall, the increase in the specific ethanol formation in strain TN9 with increasing amounts of serine in the feed might be due to this increase in ATP consumption in the synthesis of glutamate. In the cultivation of TN12 with ammonium as the sole nitrogen source glutamate synthase catalysed the synthesis of glutamate since the specific Gdh2p activity was measured to 0.005 units per mg TCP. As described earlier the specific activity of the NADH-dependent glutamate dehydrogenase increased with increasing amounts of serine in the feed but the level did not exceed 0.065 units per mg TCP which probably was to low to substitute glutamate synthase in formation of glutamate. Hence, ATP consumption in biomass synthesis remained constant in the cultivations, which resulted in a constant specific ethanol formation. The NADPH-dependent glutamate dehydrogenase catalysed glutamate formation in the cultivations of TN1. Thus, an increase in ATP consumption in the assimilation of ammonium could not explain the small increase in the specific ethanol formation observed in the cultivations with 5 mM and 15 mM serine in the feed. Instead, the observed increase of approximately 6% compared to the cultivation with ammonium as the sole nitrogen source could be due to the sum of small changes in the metabolism, resulting in an increased ATP consumption in biomass synthesis. In the cultivation of TN9 with ammonium as the sole nitrogen source an increase in the specific ethanol production and a decrease in the specific glycerol production of 22% and 20%, respectively, was observed compared to the cultivation of TN1. Similar results were obtained in the cultivation of TN12. Thus, deletion of GDH1, resulting in formation of cellular glutamate by Glt1p, led to a *S. cerevisiae* strain with improved characteristics for ethanol production.

To further analyse the effect of GDH2 overexpression in a Δgdh1 mutant without the influence of serine addition a glucose-limited continuous cultivation of strain TN22 was carried out with ammonium as the sole nitrogen source at a dilution rate of 0.11 h$^{-1}$. As mentioned above TN22 has the strong, constitutive promoter of PGK inserted in front of GDH2 on chromosome IV. A specific activity of 0.381 units per mg TCP of the NADH-dependent glutamate dehydrogenase was measured in cell-free extracts from the steady state cultivation of TN22 while the activities of Gdhp1 and Glt1p was absent and 0.012 units per mg TCP, respectively. The carbon balance and the balance over the degree of reduction of the substrates and products measured in the cultivation both closed within 3.8%. Thus, it was concluded that all products secreted by the cell had been quantified correctly. The high Gdh2p activity was reflected in the measured specific production rates of ethanol and glycerol. The two rates were measured to 411 c-mmoles per c-mole biomass per hour and 24 c-mmoles per c-mole biomass per hour, respectively. The low value for the specific ethanol production was similar to the value measured in the continuous cultivation of TN1 with ammonium as the sole nitrogen source. Hence, the level of ATP consumption in the assimilation of ammonium into glutamate probably was identical in the two strains. This indicated that in TN22 the NADH-dependent glutamate dehydrogenase completely had substituted the role of glutamate synthase in glutamate synthesis that was observed in strains TN9 and TN12. The very low specific glycerol production in TN22 compared to strain TN9 and TN12 was surprising. The specific uptake of ammonium in the cultivation was 19.2 mmoles per c-mole biomass per hour which was 12% higher than in TN9. Also the biomass yield increased from 123 c-mmoles per c-mole glucose in TN9 to 138 c-mmoles per c-mole glucose in TN22. This indicated that the high Gdh2p activity resulted in a higher flux from 2-oxoglutarate and ammonium to glutamate in TN22 than in TN9, which led to an increase in NADH reoxidation through the reaction catalysed by the enzyme, and thus, a decrease in formation of glycerol. Furthermore, it indicated that the reduction in biomass Yields observed in the continuous cultivations of TN9 and TN12 compared to TN1 and TN22 (Tables 1–3) was due to a limitation in the ammonium assimilation. No changes in formation of the organic acids were observed compared to TN9 and TN12.

Batch cultivations. The anaerobic physiology of the genetically engineered S. cerevisiae strains were also studied in batch cultivations with glucose as the primary carbon source and either ammonium or serine as nitrogen source. This was done to quantify the effect of the genetic changes on the maximum specific growth rate, $\mu_{max}$, and on the product yields.

The product yields obtained in the anaerobic batch cultivations of the four strains are listed in Table 4.

TABLE 4

| Strain | TN1 | | TN9 | | TN12 | | TN22 |
|---|---|---|---|---|---|---|---|
| Serine (mM) | 0 | 60 | 0 | 60 | 0 | 60 | 0 |
| Ammonium (mM) | 60 | 0 | 60 | 0 | 60 | 0 | 60 |
| Ethanol | 0.480 | 0.491 | 0.520 | 0.534 | 0.526 | 0.531 | 0.500 |
| Glycerol | 0.097 | 0.067 | 0.060 | 0.037 | 0.066 | 0.040 | 0.067 |
| Pyruvate | 0.003 | 0.002 | 0.003 | 0.003 | 0.002 | 0.002 | 0.004 |
| Acetate | 0.003 | 0.028 | 0.004 | 0.018 | 0.019 | 0.022 | 0.001 |
| Succinate | 0.003 | 0.003 | 0.002 | 0.004 | 0.003 | 0.004 | 0.003 |
| Carbon dioxide | 0.261 | 0.262 | 0.275 | 0.278 | 0.272 | 0.275 | 0.262 |
| Biomass | 0.121 | 0.119 | 0.114 | 0.105 | 0.072 | 0.107 | 0.126 |
| Total | 0.968 | 0.972 | 0.978 | 0.979 | 0.960 | 0.981 | 0.963 |
| $\mu_{max}$ (h$^{-1}$) | 0.41 | 0.31 | 0.22 | 0.20 | 0.17 | 0.24 | 0.39 |

Table 4. Product yields in the anaerobic, glucose-limited batch cultivations of strains TN1, TN9, TN12 and TN12 with either ammonium or serine as nitrogen source. Unit in the cultivation with ammonium as nitrogen source: c-moles product per c-mole glucose consumed. Unit in the cultivation with serine as nitrogen source: c-moles product per c-moles glucose and serine consumed.

The glycerol yield decreased significantly when strain TN1 was cultivated with serine as nitrogen source as compared to the cultivation on ammonium. As for the continuous cultivations this was due to a reduction in surplus formation of NADH in biomass synthesis under these growth conditions. A dramatic increase in formation of acetate was observed and also the ethanol yield increased. The total cellular uptake of serine was 309 c-mmoles per c-mole biomass. By assuming the constant need for de novo serine synthesis of 157 c-mmoles per c-mole biomass used in the earlier calculations it could be calculated that 152 c-mmoles serine per c-mole biomass was catabolised to ethanol and acetate. The specific ethanol and acetate formation increased with 92 c-mmoles per c-mole biomass and 210 c-mmoles per c-mole biomass, respectively, when serine was used as nitrogen source instead of ammonium. Thus, degradation of serine to acetate could not account for the increase in the yield of the component alone. Formation of acetate by the NAD(P)$^+$-dependent aldehyde dehydrogenase, encoded by ALD2, has been proposed to have a physiological role in reduction of NADP$^+$ to NADPH, which is consumed in biomass synthesis (Bruinenberg et al., 1983b; Miralles and Serano, 1995). Serine is a precursor in synthesis of cysteine and phospholipids, which are synthesis pathways that require large amounts of NADPH. The presence of high concentrations of intracellular serine could potentially increase the flux through these pathways and account for the increase in NADPH formation through synthesis of acetate. The maximum specific growth rate of TN1 decreased significantly from 0.41 h$^{-1}$ to 0.31 h$^{-1}$ when the nitrogen source was switched from ammonium to serine. When serine is used as nitrogen source the nitrogen has to be made available for biomass synthesis through degradation of the amino acid to pyruvate and ammonium. This process is less efficient than direct uptake of ammonium followed by assimilation into glutamate catalysed by glutamate dehydrogenase and glutamate synthase and hence, the reduction in the specific growth rate probably was due to this difference in nitrogen assimilation. The production of ethanol, glycerol, acetate and carbon dioxide as functions of time is shown in FIGS. 7 and 8 for the cultivations of TN1 with ammonium and serine as nitrogen sources, respectively. In the cultivation on ammonium the carbon dioxide content in the exhaust gas decreased rapidly to zero within 40 minutes after depletion of glucose in the medium also formation of other products ended. Thus, the metabolism stopped when the available carbon source was consumed. In the cultivation with serine as nitrogen source the drop of the carbon dioxide content in the exhaust gas lasted 400 minutes after depletion of glucose. The measurements strongly indicated that this was due to degradation of serine to pyruvate and further into acetate whereby carbon dioxide was formed since the concentration of acetate continued to increase after depletion of glucose while the concentrations of the other products remained constant (FIG. 8). Due to capacity problems only the total consumption of serine in the cultivation was measured by quantifying the serine content in the start and end samples. Hence, it could not be calculated whether the acetate formation after glucose depletion was due to serine degradation. The slow decrease in carbon dioxide formation after depletion of glucose was not observed in the cultivations of TN9 and TN12 when serine was used as nitrogen source. This could indicate that acetate was produced in the cultivation of TN1 to form NADPH, which in turn was consumed in assimilation of ammonium, stemming from degradation of serine, by the NADPH-dependent glutamate dehydrogenase.

Biomass samples were withdrawn from the batch cultivations when the cells had reached the exponential growth phase and the specific activities of Gdh1p, Gdh2p and Glt1p were measured in the pool of proteins extracted from these samples (Table 5).

as nitrogen source. The specific activities of Gdh2p and Glt1p in the exponential growth phase were 0.055 and 0.045 units per mg TCP, respectively, while no activity of Gdh1p could be detected. Thus, the reduction in the specific growth rate of the strain probably was due to a reduction in the rate of glutamate synthesis from ammonium and 2-oxoglutarate since the total specific activity of the two enzymes was more than ten times lower that of Gdh1p in TN1. The low activity of Gdh2p compared to the activity of the enzyme in the continuous cultivations was due to transcriptional repression by glucose (Coschigano et al., 1991). As observed in the continuous cultivations assimilation of ammonium by a combination of glutamate synthase and the NADH-dependent glutamate dehydrogenase resulted in an increase in the ethanol yield and a decrease in the glycerol yield due to consumption of NADH and ATP in the synthesis of glutamate as compared to consumption of only NADPH in strain TN1. When serine was used as nitrogen source the same qualitative changes in the yields of ethanol, glycerol and acetate was observed as in the cultivations of TN1. The increase in the acetate yield from 0.004 c-moles per c-mole glucose to 0.018 c-moles per c-mole glucose and serine was lower than observed in TN1, indicating that part of the NADPH consumed by Gdh1p in TN1 was synthesised through oxidation of acetaldehyde to acetate by the cytoplasmic $NAD(P)^+$-dependent aldehyde dehydrogenase. The decrease in the biomass yield of TN9 was lower when serine was used as nitrogen source instead of ammonium. This was not observed in the cultivations of TN1 and TN12 and could was not explained by any of the measured changes in product yields or enzyme activities.

The activities of Gdh2p and Glt1p in the exponential growth phase of TN12 were 0.006 and 0.050 units per mg TCP, respectively, when ammonium was used as nitrogen source. Thus, the total activity of the enzymes in the

TABLE 5

| Strain | TN1 | | TN9 | | TN12 | | TN22 |
|---|---|---|---|---|---|---|---|
| Serine (mM) | 0 | 60 | 0 | 60 | 0 | 60 | 0 |
| Ammonium (mM) | 60 | 0 | 60 | 0 | 60 | 0 | 60 |
| Gdh1p | 1.522 | 1.197 | 0 | 0 | 0 | 0 | 0 |
| Gdh2p | 0.020 | 0.221 | 0.055 | 0.218 | 0.006 | 0.329 | 0.625 |
| Glt1p | 0.030 | 0.048 | 0.045 | 0.045 | 0.050 | 0.040 | 0.040 |

Table 5. Specific enzyme activities of the NADPH-dependent and NADH-dependent glutamate dehydrogenases and glutamate synthase in protein extracts from biomass samples withdrawn in the exponential growth phase of strains TN1, TN9, TN12 and TN22 in the glucose-limited batch cultivations with either ammonium or serine as nitrogen source.

The specific activity of the NADPH-dependent glutamate dehydrogenase decreased from 1.522 to 1.197 units per mg TCP while that of the NADH-dependent isoenzyme increased from 0.020 to 0.221 units per mg TCP when serine was used as nitrogen source instead of ammonium. Also a small increase in the specific activity of glutamate synthase was observed. This could indicate that a small shift occurred in the cofactor specificity of ammonium assimilation into glutamate towards consumption of both NADPH and NADH. Since the reduction in the glycerol yield was accounted for by the effect on surplus NADH formation of serine consumption the major part of the intracellular ammonium probably still was assimilated under consumption of NADPH by Gdh1p.

Deletion of GDH1 in TN9 resulted in a decrease in the specific growth rate to 0.22 $h^{-1}$ when ammonium was used as nitrogen source. Since activity of Gdh2p was close to zero in TN12 under these growth conditions the synthesis of glutamate was catalysed by glutamate synthase alone. This led to a small increase in the ethanol yield. As opposed to the observations from the cultivations of TN1 and TN9 on ammonium as nitrogen source a dramatic increase in the acetate yield and a corresponding reduction in the biomass yield was observed in TN12. The drop in the amount of biomass synthesised per mole of glucose suggested that a significant change in the anabolism of the cell had occurred. An important role of glutamate in the metabolism is donation of ammonium in synthesis of many amino acids through deamination to 2-oxoglutarate catalysed by the two-ammonium assimilation was even lower than observed in TN9 and resulted in a further reduction in the maximum specific growth rate to 0.15 $h^{-1}$, almost a decrease to one third of $\mu_{max}$ in TN1.

glutamate dehydrogenases. As described the specific activities of these were very low in TN12, which could limit the flux through the synthesis pathways to these amino acids and thus, the total flux towards biomass synthesis. The increase in acetate formation could be due to an increase in NADPH consumption in biomass synthesis. When serine was used as nitrogen source the specific activity of Gdh2p increased to 0.329 units per mg TCP. This represented an induction of the enzyme by a factor of more than 50 while the Gdh2p activity only increased ten times in TN1 when serine was added. Hence, the induction of the CHA1 promoter by serine was functional in TN12. The activity of Glt1p decreased slightly to 0.040 units per mg TCP. The increased activity of the NADH-dependent glutamate dehydrogenase resulted in a marked increase in the maximum specific growth rate of the strain. This clearly illustrated that the growth rate of the strain was limited by the flux towards glutamate when ammonium was used as nitrogen source. Furthermore, it demonstrated that Gdh2p was able to substitute both Gdh1p and Glt1p in synthesis of glutamate from ammonium and 2-oxoglutarate. The high Gdh2p activity also resulted in a biomass yield comparable to the values obtained in the cultivations of TN1 and TN9. This supported the theory that the low biomass yield on ammonium was due to a limitation in biomass synthesis by the deamination reaction from glutamate to 2-oxoglutarate.

In order to analyse the effect of GDH2 overexpression in TN9 without the influence of serine addition anaerobic batch cultivations of strain TN22 was carried out with glucose as carbon source and ammonium as nitrogen source. When the original GDH2 promoter was substituted by the strong, constitutive PGK promoter in TN22, a Gdh2p activity in the exponential growth phase of 0.625 was obtained. This resulted in a dramatic increase in the maximum specific growth rate from 0.22 h$^{-1}$ to 0.39 h$^{-1}$ which was very close to $\mu_{max}$ in strain TN1. Again this illustrated that the NADH-dependent glutamate dehydrogenase could fully substitute the NADPH-dependent isoenzyme if expressed at a sufficient level. The biomass yield in TN22 increased by 11% compared to TN9 and was even higher than in TN1. This resulted in a higher glycerol yield since the amount surplus NADH formed increased per c-mole of glucose that was consumed. The increase in the ethanol yield that was observed in TN9 was absent in the cultivation of TN22, which illustrated that glutamate synthesis from ammonium and 2-oxoglutarate, occurred without consumption of ATP in TN22.

Concluding remarks. The work described herein above was carried out to analyse if the activity of the GDH1 encoded NADPH-dependent glutamate dehydrogenase could advantageously be substituted by the GDH2 encoded NADH-dependent isoenzyme in a process involving assimilation of ammonia and 2-oxoglutarate into glutamate. Another objective was to analyse the effect of such metabolically engineered ammonia assimilation on the product formation in anaerobic cultivations.

The anaerobic batch cultivation of strain TN22 clearly demonstrated that high expression of GDH2 in a Δgdh1 mutant resulted in a strain wherein the physiological role of Gdh1p in a wild-type strain had been taken over by Gdh2p. Furthermore, it was shown that this change in the metabolism resulted in a reduction of glycerol formation. Thus, formation of surplus NADH in biomass synthesis exerts a major effect on glycerol synthesis. Most likely, a further reduction in the formation of undesirable metabolic products can be obtained by metabolically engineering other reactions catalysed by isoenzymes with different cofactor specificities.

The reduced glycerol yield did not result in an increase of the metabolic flux towards ethanol. Accordingly, in the metabolically engineered strains, the formation of ethanol is not limited by the flux of metabolites towards other fermentation products.

An attempt was made to study the effect of GDH2 overexpression on the anaerobic physiology in more detail by introducing the inducible promoter of CHA1 in front of GDH2 on chromosome IV. The induction of the promoter by serine was clearly evident, but very high amounts of the amino acid had to be added to the medium in order to obtain a high expression of GDH2. Addition of up to 30 mM of serine to the medium in a continuous cultivation affected the metabolism of the cells and complicated the analysis of the experiments. In batch cultivations of TN12, induction of GDH2 expression by serine resulted in a significant increase in the specific growth rate of that strain. This result reiterated the conclusion reached herein above that the activity of Gdh2p can indeed substitute that of Gdh1p in a cellular metabolism.

A significant increase in the formation of ethanol and a decrease in the formation of glycerol were observed, when GDH1 was deleted in strain TN9. This may be due to a synthesis of glutamate via two coupled reactions mediated by GLT1 encoded glutamate synthase and GLN1 encoded glutamine synthetase. Synthesis of glutamate via these two coupled reactions results in consumption of both NADH and ATP and said consumption may explain the observed changes in product formation. Unfortunately, the maximum specific growth rate of strain TN9 was also reduced by the deletion in question and thus, no overall increase in ethanol productivity was obtained. The lower growth rate was probably due to a limitation in the synthesis rate of glutamate. This is conceivable since the activity of Glt1p was much lower than the activity of Gdh1p which catalysed glutamate formation in strain TN1.

The experiments described above have demonstrated that the observed growth defect could be alleviated by an overexpression of GDH2. Accordingly, a key question is: Does an overexpression of Glt1p and Gln1p result in a strain with an increased ethanol productivity as well as a higher growth rate, as compared to a wild-type strain?

EXAMPLE 2

Metabolically Engineered Ammonia Assimilation and Ethanol Production in Yeast

Introduction

In this example, a new strategy is presented for optimisation of the ethanol yield in *Saccharomyces cerevisiae* through metabolic engineering. It is based on the physiological roles of glycerol and ethanol in oxidation of surplus NADH and in formation of ATP, respectively, under anaerobic growth conditions. Experimental results from anaerobic batch cultivations of strains developed on the basis of the strategy are presented.

Materials and Methods

Microorganisms and their maintenance. All *Saccharomyces cerevisiae* strains were generated from *Saccharomyces cerevisiae* T23D. The strain was kindly provided by Jack Pronk from the Department of Microbiology and Enzymology, Kluyver Laboratory of Biotechnology, Delft University of Technology, The Netherlands. The yeast strains were maintained at 4° C. on YPG agar plates, monthly prepared from a lyophilised stock kept at −80° C. *Escherichia coli*

DH5α (F—F80dlacZ DM 15 D(lacZYA-argF) U 169 deoR recA1 endA1 hsdR17($r_k^- m_k^+$) supE44l⁻ thi-1 gyra96 relA1) (GIBCO BRL. Gaithersburg, Md., USA) was used for subcloning.

Preparation of DNA. Plasmid DNA from *E. coli* was prepared with Qiagen columns (Qiagen GmbH, Düsseldorf, Germany) following the manufacturer's instructions. For the purification of DNA fragments used for cloning experiments, the desired fragments were separated on 0.8% agarose gels, excised and recovered from agarose using the Qiagen DNA isolation kit (Qiagen GmbH, Düsseldorf, Germany). Chromosomal DNA from *Saccharomyces cerevisiae* was extracted as follows. Cells were cultivated in medium in shake flasks and harvested at OD=1.5, 10 mg of wet cells were resuspended in 0.5 ml Tris-Cl (pH 8.0) and quenched with 0.5 ml glass beads (size 250–500 microns) in the presence of 0.5 ml Tris-saturated phenol (pH 8.0). The DNA was extracted from the phenol phase with chloroform, precipitated with 98% ethanol and resuspended in TE buffer. RNA in the extract was removed by treatment with RNAaseA (purchased from Promega) and finally the DNA was purified by precipitation with ethanol/lithium chloride and resuspended in TE buffer. The DNA primers were purchased from DNA Technology (Aarhus, Denmark).

Overexpression of GLT1. Primers Glt1start (5'-GCG CGG GAT CCT CTA GAA TGC CAG TGT TGA AAT CAG AC-3'), SEQ ID NO:9, containing restriction enzyme sites for BamHI and XbaI in front of nucleotides 1 to 21 of GLT1, and Glt1stop (5'-CGC GCG GAT CCC CGC GGG CTG GAC CAT CCC AAG GTT CC-3'). SEQ ID NO:10, containing restriction enzyme sites for BamHI and SacII in front of nucleotides 1149 to 1169 of GLT1, were used to clone parts of the structural gene of GLT1 by PCR with the pfu polymerase (New England Biolabs). A DNA fragment of the correct size was isolated from a 0.8% agarose gel after electrophoresis and digested with BamHI overnight. The fragment was ligated into the unique BglII digestion site of plasmid Yep24-pPGK behind the PGK promoter and in front of the PGK terminator (Walfridsson et al. 1997), resulting in plasmid Yep24-pPGK-GLT1. A 2.5 kb SmaI/SacII DNA fragment, consisting of the PGK promoter and the cloned part of GLT1 was isolated from Yep24-pPGK-GLT1. The fragment was ligated into plasmid pFA6A-kanMX3 (Wach et al. 1994), digested with EcoRV and SacII, resulting in plasmid pPGK-GLT1 (FIG. 9). The plasmid was linearised by digestion with EcoRV prior to transformation. Correct insertion of the plasmid into the GLT1 locus on chromosome IV was verified by PCR analysis of chromosomal DNA extracted from transformants with resistance towards geniticin. For this purpose primers PGKverif, spanning the region 420 to 400 bp upstream of the PGK start codon, and GLT1verif, spanning the region from nucleotides 124, to 1260 of GLT1, were constructed. Loop out of the geniticin resistance gene by homologues recombination of the two direct repeats flanking the gene was obtained by cultivating correct transformants for up to 100 generations in nonselective YPD medium followed by plating of approximately 50000 colonies on YPD-plates. The colonies were then replica plated to YPD plates containing 150 mg per liter geniticin and transformants without resistance towards geniticin were isolated. The loop out frequency was approximately 1 per 25000 colonies. It was verified by PCR analysis of chromosomal DNA from loop out transformants that the PGK promoter was still introduced in front of GLT1.

Overexpression of GLN1. Primers Gln1start (5'-GCG CGG GAT CCT CTA GAA TGG CTG AAG CAA GCA TCG AA-3'), SEQ ID NO: 11, containing restriction enzyme sites for BamHI and XbaI in front of nucleotides 1 to 21 of GLN1, and Gln1stop (5'-CGC GCG GAT CCC CGC GGT TAT GAA GAT TCT CTT TCA AA-3'). SEQ ID NO:12, containing restriction enzyme sites for BamHI and SacII in front of nucleotides 1093 to 1113 of GLN1, were used to clone GLN1 by PCR with the pfu polymerase (New England Biolabs). The obtained DNA fragment was used to construct plasmid pPGK-GLN1, containing GLN1 behind the promoter of PGK inserted into pFA6A-kanMX3 (FIG. 9), as described above for plasmid pPGK-GLT1, pPGK-GLN1 was linearised by digestion with KpnI prior to transformation. Correct insertion of the plasmid into the GLN1 locus on chromosome XVI was verified by PCR analysis of chromosomal DNA extracted from transformants with resistance towards geniticin. For this purpose primers PGKverif, spanning the region 420 to 400 bp upstream of the PGK start codon, and GLN1verif, spanning the region from nucleotides 52 to 70 downstream of GLT1, were constructed.

Transformation of *E. coli* and *S. cerevisiae*. *E. coli* DH5α was transformed by electro-transformation using the Bio-Rad electroporation equipment (Biorad Laboratories, Richmond, USA). Transformants were selected on L broth plates containing 100 mg/ml ampicillin. *S. cerevisiae* cells were made competent for plasmid uptake by treatment with lithium acetate and polyethyleneglycol (Schiestl & Gietz, 1989). 3 µg of DNA was used for each transformation. Transformants were suspended in YPD for 24 hours prior to plating on YPD, containing 150 mg geniticin per liter, in order to obtain expression of the G418 resistance gene.

Medium in the batch cultivations. The strains of *S. cerevisiae* were cultivated in a mineral medium prepared according to Verduyn et al. (1990). Vitamins were added by sterile filtration following heat sterilisation of the medium. The concentrations of glucose and $(NH_4)_2SO_4$ initially in the batch cultivations were 25 g per l and 3.75 g per l, respectively. Growth of *S. cerevisiae* under anaerobic conditions requires the supplementary addition to the medium of ergosterol and unsaturated fatty acids, typically in the form of Tween 80 (Andreasen & Stier, 1953: Libudzisz et al., 1986). Ergosterol and Tween 80 were dissolved in 96% (v/v) ethanol and the solution was autoclaved at 121° C. for 5 min. The final concentrations of ergosterol and Tween 80 in the medium were 4.2 mg per g DW and 175 mg per g DW, respectively. To prevent foaming 75 µl per l antifoam (Sigma A-5551) was added to the medium.

Experimental set-up for the batch cultivations. Anaerobic batch cultivations were performed at 30° C. and at a stirring speed of 600 rpm in in-house manufactured bioreactors. The working volume of the batch reactors was 4.5 liters. pH was kept constant at 5.00 by addition of 2 M KOH. The bioreactors were continuously sparged with $N_2$ containing less than 5 ppm $O_2$, obtained by passing $N_2$ of a technical quality (AGA 3.8), containing less than 100 ppm $O_2$, through a column (250×30 mm) filled with copper flakes and heated to 400° C. The column was regenerated daily by sparging it with $H_2$ (AGA 3.6). A mass flow controller (Bronkhorst HiTec F201C) was used to keep the gas flow into the bioreactors constant at 0.50 l nitrogen min⁻ liter⁻ Norprene tubing (Cole-Parmer Instruments) was used throughout in order to minimise diffusion of oxygen into the bioreactors. The bioreactors were inoculated to an initial biomass concentration of 1 mg l⁻¹ with precultures grown in unbaffled shake flasks at 30° C. and 100 rpm for 24 hours. Ethanol evaporation from the bioreactors was minimised by off-gas condensers cooled to 2° C. The anaerobic batch cultivations of strains TN1, TN9, TN15, TN17 and TN19 were each carried out three times with identical results.

Determination of dry weight. Dry weight was determined gravimetrically using nitrocellulose filters (pore size 0.45 µm: Gelman Sciences). The filters were predried in a microwave oven (Moulinex FM B 935Q) for 10 min. A known volume of culture liquid was filtered and the filter was washed with an equal volume of demineralised water followed by drying in a microwave oven for 15 min. The relative standard deviation (RSD) of the determinations was less than 1.5% based on triple determinations (n=3).

Analysis of medium compounds. Cell-free samples were withdrawn directly from the bioreactor through a capillary connected to a 0.45 µm filter. Samples were subsequently stored at −40° C. Glucose, ethanol, glycerol, acetic acid, pyruvic acid, succinic acid and 2-oxoglutarate were determined by HPLC using an HPX-87H Aminex ion exclusion column (RSD<0.6%, n=3). The column was eluted at 60° C. with 5 mM $H_2SO_4$ at a flow rate of 0.6 ml min$^{-1}$. Pyruvic acid, acetic acid and 2-oxoglutarate were determined with a Waters 486 UV meter at 210 mm whereas the other compounds were determined with a Waters 410 refractive index detector. The two detectors were connected in series with the UV detector first. The $CO_2$ concentration in the off-gas was determined using a Brüel & Kjær 1308 acoustic gas analyser (RSD=0.02%) (Christensen et al., 1995). In a separate experiment the off gas from the bioreactor was bubbled through liquid nitrogen and the ethanol concentration in the frozen mixture of water, ethanol and acetaldehyde was determined by HPLC after evaporation of the $N_2$. Hereby the loss of ethanol through the reflux condenser of the bioreactor was determined to be between 4% and 9% of the ethanol formed by the bioreaction depending on the dilution rate (Schulze, 1995). In the carbon balances the measured ethanol fluxes were corrected for this loss through evaporation.

Measurement of enzyme activities. Culture liquid was withdrawn from the bioreactor into an ice cooled beaker, centrifuged and washed twice with 10 mM potassium phosphate buffer (pH 7.5, 2° C.) containing 2 mM EDTA. Subsequently the cells were resuspended in 4.2 ml 100 mM potassium phosphate buffer (pH 7.5, 2° C.) containing 2 mM $MgCl_2$ followed by immediate freezing in liquid nitrogen and storage at −40° C. Prior to analysis 0.22 ml of 20 mM DTT was added to the samples whereafter they were distributed into precooled 2 ml eppendorf tubes containing 0.75 ml glass beads (size 0.25–0.50). The cells were disrupted in a bead mill for 12.5 min. (0° C.). The test tubes were centrifuged (20000 rpm. 20 min., 0° C.) whereafter the supernatants were pooled in one test tube. During the following analyses the extract was kept on ice. Enzyme assays were performed at 30° C. using a Shimadzu UV-260 spectrophotometer at 30° C. Reaction rates, corrected for endogenous rates, were proportional to the amount of extract added. All enzyme activities are expressed as micromole of substrate converted per minute per mg total cellular protein as determined by the Lowry method. Glutamate dehydrogenase (NAD$^+$ and NADP$^+$) (EC 1.4.1.5 and EC 1.4.1.4, respectively) were assayed as described by Bruinenberg et al. (1983a). Glutamine synthetase (EC 6.3.1.2) and glutamate synthase (GOGAT) (EC 1.4.1.14) was assayed as described by Holmes et al. (1989).

Results

Metabolic control analysis. Anaerobic physiology in continuous cultivations of *S. cerevisiae* CBS8066 has previously been analysed hy means of metabolic flux analysis and said theoretical although practically applicable analysis showed that the flux through the reaction catalysed by the NADPH-dependent glutamate dehydrogenase (reaction 25 in a proposed model) was 8.0 c-mmoles per g biomass per hour at a dilution rate of 0.3 h$^{-1}$, although the net flux from 2-oxoglutarate to glutamate was only 2.0 c-mmoles per g biomass per hour.

Accordingly, if Glt1p and Gln1p catalysed the same reaction instead of Gdh1p, one mole of NADH and one mole of ATP would be expected to be consumed per mole of glutamate synthesised, instead of consumption of one mole NADPH. The result of such a metabolic engineering would consequently be a reduction in a surplus formation of NADH.

A decrease in the formation of glycerol from 9.8 to 5.0 c-mmoles per g biomass per hour, a reduction by 49%, was predicted. Furthermore, the consumption of ATP was hypothesised to result in a 6% increase of ethanol formation, from 54.9 to 58.2 c-mmoles per g biomass per hour.

Construction of new strains. Earlier the haploid *S. cerevisiae* strain TN1 was constructed from a diploid progeny of the industrial model strain *S. cerevisiae* CBS8066 (Nissen et al., 1998b). This was done by deletion of HO, encoding an endonuclease involved in mating type switching, and isolation of stable haploids following sporulation of deletion mutants. Furthermore GDH1 was deleted in TN1 as described earlier, resulting in strain TN9 (Nissen et al., 1998a). In this study the object was to construct new strains from TN9 with a stable, constitutive overexpression of GLN1, encoding glutamine synthetase, and GLT1, encoding glutamate synthase. This was achieved by inserting the strong, constitutive promoter of PGK in front of the two genes on chromosomes XVI and IV, respectively. PGK encodes one of the most abundant mRNA and protein species in the cell, accounting for 1% to 5% of the total cellular mRNA and protein during growth on fermentative carbon sources (Dobson et al. 1982). By integrating the promoter into the chromosome, problems with plasmid loss, resulting in an unstable phenotype, could be avoided. TN9 was transformed with either of the linearised plasmids pPGK-GLN1 and pPGK-GLT1, resulting in strains TN15 and TN17, respectively. It was verified by PCR analysis that the strong, constitutive promoter of PGK had been inserted into the chromosome in front of the structural genes, encoding glutamine synthetase and glutamate synthase, respectively. TN17 was cultivated in non-selective YPD medium for 100 generations in order to remove the resistance against geniticin by homologues recombination of the direct repeats flanking the resistance gene in the chromosome. This resulted in isolation of strain TN18 which had lost the geniticin resistance but maintained the strong promoter in front of GLT1. TN18 was transformed with pPGK-GLN1 as described above, resulting in strain TN19 with the PGK promoter inserted in front of both GLN1 and GLT1 in the chromosome. Table 6 lists the phenotypes of all strains that were cultivated in batch reactors in this study.

TABLE 6

| Strain | Phenotype | Reference |
|---|---|---|
| TN1 | MATα ho-Δ1 | Nissen et al., 1998b |
| TN9 | MATα ho-Δ1 ura3-Δ20::SUC2 gdh1-Δ1:: URA3 | Nissen et al., 1998a |
| TN15 | MATα ho-Δ1 ura3-Δ20::SUC2 gdh1-Δ1:: URA3 gln1::(PGKp-GLN1) | This study |
| TN17 | MATα ho-Δ1 ura3-Δ20::SUC2 gdh1-Δ1:: URA3 glt1::(PGKp-GLT1) | This study |

TABLE 6-continued

| Strain | Phenotype | Reference |
|---|---|---|
| TN19 | MATα ho-Δ1 ura3-Δ20::SUC2 gdh1-Δ1:: URA3 glt1::(PGKp-GLT1) gln1::(PGKp-GLN1) | This study |

Table 6. Phenotypes of the strains cultivated in anaerobic batch fermentations in this study.

Glucose limited batch cultivations. The anaerobic physiology of the genetically engineered *S. cerevisiae* strains were studied in batch cultivations with glucose as the primary carbon source and ammonium nitrogen source. This was done to quantify the effect of the genetic changes on the specific enzyme activities of Gdh1p, Gdh2p, Glt1p and Gln1p, the maximum specific growth rate, $\mu_{max}$, and on the product yields.

The specific enzyme activities were measured in protein extracts from biomass samples withdrawn from the bioreactors when the cells were in the exponential growth phase (Table 7).

TABLE 7

|  | TN1 | TN9 | TN15 | TN17 | TN19 |
|---|---|---|---|---|---|
| Gdh1p | 1.522 | n.d. | n.d. | n.d. | n.d. |
| Gdh2p | 0.020 | 0.055 | 0.045 | 0.028 | 0.033 |
| Gln1p | 0.011 | 0.009 | 0.068 | 0.009 | 0.062 |
| Glt1p | 0.030 | 0.045 | 0.045 | 0.195 | 0.211 |

Table 7. Product yields of strains TN1, TN9, TN13, TN17 and TN19 in the anaerobic, glucose-limited batch cultivations that were carried out in this study. Unit: c-moles product per c-mole glucose.

As observed earlier the activity of the NADPH-dependent glutamate dehydrogenases in strain TN1 were 50–100 times higher than the remaining enzymes involved in assimilation of ammonium. This demonstrated the importance of this enzyme in wild-type cells during growth on ammonium as nitrogen source. No activity of Gdh1p could be detected in extracts from the four strains where GDH1 had been deleted. Thus, GDH3p had no physiological role in this strain background when ammonium was used as nitrogen source. The activity of the NADH-dependent glutamate dehydrogenase, encoded by GDH2, was approximately 2.5 times higher in strain TN9 than observed in the haploid wild-type. As described earlier this increase probably was due to a decrease in the intracellular concentration of glutamine since this metabolite represses expression of GDH2 at the transcriptional level (Nissen et al., 1998a). This decrease could be due to a limitation in the synthesis rate of glutamate in cells with a deletion in GDH1. Almost a similar increase in Gdh2p activity was observed in strain TN15, indicating that overexpression of the structural gene for glutamine synthetase only resulted in a limited increase in the intracellular concentration of glutamine. In strains TN17 and TN19 the Gdh2p activity was reduced to a level close to that observed in TN1. Thus, an increase in the intracellular glutamine concentration to wild-type probably was achieved by overexpression of glutamate synthase, resulting in an increase in the synthesis rate of glutamate. Insertion of the strong constitutive promoter of PGK in front of GLN1 into the chromosome of TN15 and TN19 resulted in an increase in the specific activity of glutamine synthetase from approximately 0.0100 units per mg total cellular protein (TCP) in strains TN1 and TN9 to 0.068 and 0.062 units per mg TCP, respectively. Insertion of the promoter in front of GLT1 resulted in a five-fold increase in the activity of glutamate synthase in strains TN17 and TN19 compared to the three other strains. Thus, it was concluded that the new promoter had been inserted correct into the chromosome and that this resulted in the expected increase in the specific activities of glutamine synthetase and glutamate synthase.

In FIG. 10 the production of biomass in the exponential growth phases of TN1, TN9, TN17 and TN19 as functions of time are depicted. Deletion of GDH1 resulted in a reduction in the maximum specific growth rate, $\mu_{max}$, from 0.41 h$^{-1}$ in strain TN1 to 0.21 h$^{-1}$ in strain TN9 (FIG. 10). As mentioned earlier this probably was due to a reduction in the synthesis rate of glutamate since the total specific activities of the enzymes that potentially could substitute the physiological role of Gdh1p, Gdh2p and Glt1p, was 15 times lower than the specific activity of Gdh1p in TN1. Overexpression of GLN1 in TN9, resulting in strain TN15, gave only a small increase in the maximum specific growth rate, to 0.24 h$^{-1}$ (results not shown). This very limited effect of the increase in Gln1p activity was probably due to a slightly higher flux towards synthesis of glutamine. As described earlier glutamine is one of the substrates in the reaction, catalysed by glutamate synthase, wherein glutamate is formed when GDH1 is deleted. Overexpression of GLN1 in TN15 probably removes a limitation in the glutamine supply to the reaction catalysed by Gltp, which results in the observed increase in $\mu_{max}$. Overexpression of GLT1 had a significant effect on the maximum specific growth rate of TN17. An increase to 0.31 h$^{-1}$ was observed. This clearly demonstrated that the reduction in the growth rate of TN9 was caused by a low synthesis rate of glutamate and that this limitation could be partly removed by constructing a strain with a high specific activity of glutamate synthase. Overexpression of both GLT1 and GLN1 was obtained in TN19. This led to a further increase in the maximum specific growth rate to 0.37 h$^{-1}$. Thus, the increase in the specific activity of glutamine synthetase had a more pronounced effect on the specific growth rate in a strain where the specific activity of glutamate synthase was high compared to in a strain with a wild-type level of activity. This indicated that overexpression of GLT1 alone probably resulted in depletion in the intracellular pool of glutamine, which limited the effect of the increase in the specific enzyme activity of Glt1p in TN17. This limitation was apparently removed by overexpression of the structural gene encoding glutamine synthetase.

The consumption of glucose and the production of ethanol, glycerol, acetate, pyruvate, succinate, biomass and carbon dioxide were measured in filtered samples withdrawn from the batch cultivations of TN1, TN9, TN15, TN17 and TN19. No variations between the five strains in formation of the organic acids were detected and thus, only the total yield of these metabolites is listed in Table 8.

TABLE 8

|  | TN1 | TN9 | TN15 | TN17 | TN19 |
|---|---|---|---|---|---|
| Ethanol | 0.480 | 0.520 | 0.521 | 0.530 | 0.531 |
| Glycerol | 0.097 | 0.060 | 0.059 | 0.061 | 0.060 |
| Biomass | 0.121 | 0.114 | 0.114 | 0.110 | 0.110 |

TABLE 8-continued

|  | TN1 | TN9 | TN15 | TN17 | TN19 |
|---|---|---|---|---|---|
| Carbon dioxide | 0.261 | 0.275 | 0.272 | 0.271 | 0.273 |
| Organic acids | 0.009 | 0.009 | 0.010 | 0.009 | 0.008 |
| Total | 0.968 | 0.978 | 0.976 | 0.981 | 0.982 |

Table 8. The specific activities of the NADPH-dependent and NADH-dependent glutamate dehydrogenases, glutamine synthetase and glutamate synthase in protein extracts from biomass samples withdrawn in the exponential growth phases of strains TN1, TN9, TN15, TN17 and TN19 in the anaerobic, glucose-limited batch cultivations.

FIGS. 11, 12 and 13 show the consumption of glucose and the production of ethanol, glycerol and carbon dioxide as functions of time in the cultivations of strains TN1, TN9 and TN 19, respectively. In all cultivations formation of ethanol, glycerol and carbon dioxide stopped immediately after depletion of glucose in the medium. No consumption of the products was detected as long as the bioreactors were sparged with nitrogen, which demonstrated that anaerobic growth conditions had been obtained in the cultivations. The reduction in $\mu_{max}$ of TN9 resulted in an increase in the duration of the anaerobic fermentation of the carbon source of 3.5 hours compared to TN1. This elongation of the fermentation time was significantly reduced in strain TN19. Here the fermentation lasted 40 minutes longer than observed in the cultivations of TN I. A relative increase in the ethanol yield of 8% was measured in the cultivations of TN9 compared to TN1 while the relative decrease in the glycerol yield was measured to 38% (Table 8). As described earlier this was due to formation of glutamate by the NADH and ATP consuming reactions catalysed by glutamate synthase and glutamine synthetase in TN9 compared to formation of glutamate by the NADPH consuming reaction catalysed by glutamate dehydrogenase I in TN1. The increase in ATP consumption in biomass synthesis resulted in a reduction of the biomass yield in TN9, by 6%. Overexpression of GLN1 alone had no significant influence on the product formation of strain TN15 compared to TN9. The five-fold increase in the specific glutamate synthase activity that was obtained by overexpression of GLT1 in strain TN17 resulted in a small increase in the ethanol yield and a similar small increase in biomass formation. This indicated that the total flux through the reactions catalysed by Glt1p and Gln1p probably was slightly higher in TN17 compared to TN9 which resulted in an increase in the ATP cost of biomass synthesis. No decrease in glycerol formation was detected. Thus, the difference in ethanol formation of TN17 and TN9 could be an artefact caused by small errors in the measurement of ethanol. The standard deviation in the ethanol yields obtained in anaerobic cultivations of the same strain was 3.5–4.1%. Overexpression of both GLN1 and GLT1 in strain TN19 did not results in any changes in product formation compared to TN17.

EXAMPLE 3

Expression of a Transhydrogenase Activity in *Lactococcus lactis* and *Escherichia coli*

Introduction cth, encoding the cytoplasmic transhydrogenase from *Azotobacter vinelandii*, was cloned by PCR using primers BglII-cth (5'-tacgaagatctGCTGTATATAAcTAC-GATGTGGTGG-3') (SEQ ID NO:13) and CTH-XhoI (5'-tagcactcgagttaAAAAAGCCGATTGAGACC-3') (SEQ ID NO:14) and pfu polymerase. The resulting DNA fragment was digested with the restriction enzymes BglII and XhoI and inserted into the multi cloning site of the *E. coli/L. lactis* shuttle vector pTRKH2-p170 behind a strong constitutive derivate of the promoter p170 (S. M. Madsen, J. Arnau, A. Vrang, M. Givskov and H. Israelsen (1999). *Molecular Microbiology* 32, 75–87). The resulting plasmid was denoted pTRKH2-p 170-cth. The promoter region of the vector and the inserted cth were sequenced, whereby it was verified that the gene had been inserted correctly into the shuttle vector.

*E. coli* DH5α and *L. lactis* subsp. *cremoris* were both transformed with pTRKH2-p170-cth and transformants were selected on plates containing complex medium (LB and GM13, respectively) supplemented with erythromycin. Independent pTRKH2-p170-cth transformants of both *E. coli* and *L. lactis* were grown in shake flasks in LB medium and GM13 medium, respectively, supplemented with erythromycin. In the late exponential growth phase, cell samples were withdrawn from the shake flasks and the protein pools of the cells were extracted.

The extracted protein pools were assayed for activity of the cytoplasmic transhydrogenase. The results are listed below

| Microorganism | Transhydrogenase activity (U per mg protein) |
|---|---|
| *E. coli* DH5α | not detectable |
| *E. coli* DH5α pTRKH2-p170-cth | 0.568 |
| *L. lactis* subsp. *cremoris* | not detectable |
| *L. lactis* subsp. *cremoris* pTRKH2-p170-cth | 0.107 |

From the data it was concluded that the cytoplasmic transhydrogenase had been succesfully expressed in both *E. coli* and *L. lactis*.

*Saccharomyces cerevisiae* strains were deposited under the Budapest Treaty with Deutsche Sammlung von Mikroorganismen und Zellkulturen GmbH, Mascheroder Weg 1b, D-38124 Braunschweig GERMANY, as follows

| Strain | Deposit No. | Deposit Date |
|---|---|---|
| TN4 | DSM 12267 | Jun. 19, 1998 |
| TN15 | DSM 12274 | Jun. 24, 1998 |
| TN17 | DSM 12275 | Jun. 24, 1998 |
| TN19 | DSM 12276 | Jun. 24, 1998 |
| TN22 | DSM 12277 | Jun. 24, 1998 |

REFERENCES AND LITERATURE CITED

Andreasen, A. A. & Stier, T. J. B. (1953). Anaerobic nutrition of *Saccharomyces cerevisiae*. I. Ergostereol requirement for the growth in a defined medium. *J Cell Comp Physiol* 41, 23–36.

Ansell R, Granath K, Hohmann S, Thevelein J M & Adler L (1997). The two isoenzymes for yeast NAD+-dependent glycerol 3-phosphate dehydrogenase encoded by GPD1 and GPD2 have distinct roles in osmoadaptation and redox regulation. *EMBO J.* 16, 2179–2187.

Avendanõ, A., Deluna, A., Olivera, H., Valenzuela, L. and Gonzales, A. (1997). GDH3 encodes a glutamate dehydrogenase isozyme, a previously unrecognized route for glutamate biosynthesis in *Saccharomyces cerevisiae*. *J Bact* 179, 5594–5597.

Barkholt, V. and Jensen, A. L. (1989). Amino acid analysis: Determination of cysteine plus half-cysteine in proteins after hydrochloric acid hydrolysis with a disulfide compound as additive. *Anal Biochem* 177,318–322.

Björkqvist, S., Ansell, R., Adler, L., and Liden, G. (1997). Physiological response to anaerobicity of glycerol-3-phosphate dehydrogenase mutants of *Saccharomyces cerevisiae*. *Appl. Environ. Microbiol.* 63, 128–132.

Boles, E., Lehnert, W. and Zimmermann, F. K. (1993). The role of the NAD-dependent glutamate dehydrogenase in restoring growth on glucose of a *Saccharomyces cerevisiae* phosphoglucose isomerase mutant. *Eur J Biochem* 217, 469–477.

Bornæs, C., Ignjatovic, M. W., Schjerling, P., Kielland-Brandt, M. C. and Holmberg, S. (1993). A regulatory element in the CHA1 promoter which confers inducibility by serine and threonine on *Saccharomyces cerevisiae* genes. *Mol Cell Biol* 13, 7604–7611.

Bruinenberg, P. M., van Dijken, J. P. & Scheffers, W. A. (1983a). An enzymatic analysis of NADPH production and consumption in *Candida utilis*. *J Gen Microbiol* 129, 965–971.

Bruinenberg, P. M., van Dijken, J. P. & Scheffers, W. A. (1983b). A theoretical analysis of NADPH production and consumption in yeasts. *J Gen Microbiol* 129, 953–964.

Christensen, L. H., Schulze, U., Nielsen, J. & Villadsen, J. (1995). Acoustic off-gas analyser for bioreactors: precision, accuracy and dynamics of detection. *Chem Eng Sci* 50, 2601–2610.

Cogoni, C., Valenzuela, L., Gonzales-Halphen, D., Olivera, H., Macino, G., Ballario, P., Gonzales, A. (1995). *Saccharomyces cerevisiae* has a single glutamate synthase gene coding for a plant-like high-molecular-weight polypeptide. *J Bact* 177, 792–798.

Coschigano, P. W., Miller, S. M., Magasanik, B. (1991). Physiological and genetic analysis of the carbon regulation of the NAD-dependent glutamate dehydrogenase of *Saccharomyces cerevisiae*. *Mol Cell Biol* 11, 4455–4465.

Courchesne, W. S. and Magasanik, B. (1988). Regulation of nitrogen assimilation in *Saccharomyces cerevisiae*: Roles of the URE2 and GLN3 genes. *J Bact* 170, 708–713.

Dobson, M. J., Tuite, M. F., Roberts, N. A., Kingsman, A. J., Kingsman (1982). Conservation of high efficiency promoter sequences in *Saccharomyces cerevisiae*. *Nucl Acid Res* 10, 2625–2637

Holmes, A. R., Collins, A., Farnden, K. J. F. & Shepherd, M. G. (1989). Ammonia assimilation by *Candida albicans* and other yeasts: Evidence for the activity of glutamate synthase. *J Gen Microbiol* 135, 1423–1430.

Larsson K, Ansell R, Eriksson P & Adler L (1993). A gene encoding sn-glycerol 3-phosphate dehydrogenase (NAD+) complements an osmosensitive mutant of *Saccharomyces cerevisiae*. *Mol Microbiol* 10, 1101–1111.

Libudzisz, Z., Mansfels, B., Kacki, E. & Obermann, H. (1986). Optimization of the cultivation medium composition for lactic acid bacteria. *Milchwiss* 41, 625–629.

Miller, S. M. and Magasanik, B. (1983). Prurification and properties of glutamine synthetase from *Saccharomyces cerevisiae*. *J Biol Chem* 258, 119–124.

Miller, S. M. and Magasanik, B. (1990). Role of the NAD-linked glutamate dehydrogenase in nitrogen metabolism in *Saccharomyces cerevisiae*. *J Bact* 172, 4927–4935.

Miller, S. M. and Magasanik, B. (1991). Role of the complex upstream region of the GDH2 gene in nitrogen regulation of the NAD-linked glutamate dehydrogenase in *Saccharomyces cerevisiae*. *Mol Cell Biol* 11, 6229–6247.

Miralles, V. J. and R. Serrano (1995). A genomic locus in *Saccharomyces cerevisiae* with four genes upregulated by osmotic stress. *Mol Microbiol* 17, 653–662.

Moye, W. S., Amuro, N., Rao, J. K. M. & Zalkin, H. (1985). Nucletide sequence of yeast GDH1 encoding nicotinamide adenine dinucleotide phosphate-dependent glutamate dehydrogenase. *J Biol. Chem.* 260, 8502–8508.

Nissen, T. L., Kielland-Brandt, M. C., Nielsen, J. and Villadsen, J. (1998a). Metabolic engineering of the ammonium assimilation in *Saccharomyces cerevisiae*. Submitted.

Nissen, T. L., Anderlund, M., Kielland-Brandt, M. C., Nielsen, J. and Villadsen, J. (1998b). Expression of a cytoplasmic transhydrogenase in *Saccharomyces cerevisiae* results in formation of 2-oxoglutarate due to a reduction in the intracellular concentration of NADPH. Submitted Nissen, T. L., Schulze, U., Nielsen, J. and Villadsen, J. (1997). Fluc distributions in anaerobic, glucose-limited continuous cultivations of *Saccharomyces cerevisiae*. *Microbiology* 143, 203–218.

Oura, E. (1977). Reaction products of yeast fermentations. *Process Biochem* 12, 19–21; 35.

Schiestl, R. H. and Gietz, R. D. (1989). High efficiency transformation of intact cells using single stranded nucleic acids as a carrier. *Curr Genet* 16, 339–346.

Schulze, U. (1995). Anaerobic physiology of *Saccharomyces cerevisiae*. Ph.D. thesis. Technical University of Denmark, Denmark.

ter Schure, E. G., Silljé, H. H. W., Raeven, L. J. R. M., Boonstra, J., Verkleij, A. J., and Verrips, C. T. (1995a). Nitrogen-regulated transcription and enzyme activities in continuous cultures of *Saccharomyces cerevisiae*. *Microbiology* 141, 1101–1108.

ter Schure, E. G., Silljé, H. H. W., Verkleij, A. J., Boonstra, J., and Verrips, C. T. (1995b). The concentration of ammonia regulates nitrogen metabolism in *Saccharomyces cerevisiae*. *J Bact* 177, 6672–6675.

Wach, A., Brachat, A., Pohlmann, R. & Philippsen, P. (1994). New heterologous modules for classical or PCR-based gene disruption in *Saccharomyces cerevisiae*. *Yeast* 10, 1793–1808.

Walfridsson, M., Anderlund, M., Bao, X. and Hahn-Hagerdahl, B. (1997). Expression of different levels of enzymes from the *Pichia stipidis* XYL1 and XYL2 genes in *Saccharomyces cerevisiae* and its effect on product formation during xylose utilisation. *Appl Microbiol Biotechnol*.

van Dijken, J. P. & Scheffers, W. A. (1986). Redox balances in the metabolism of sugars by yeasts. *FEMS Microbiology Reviews* 32, 199–224.

Verduyn, C., Postma, E., Scheffers, W. A. & van Dijken, J. P. (1990). Physiology of *Saccharomyces cerevisiae* in anaerobic glucose-limited chemostat cultures. *J Gen Microbiol* 136, 395–403.

The invention claimed is:

1. A recombinant yeast cell comprising:
   i) at least one increased expressible yeast enzyme activity controlling anabolic metabolism of ammonia in said cell as a nutrient source, said increased enzyme activity being selected from the group consisting of:
      (a) a glutamate dehydrogenase activity catalyzing the reaction: 2-oxoglutarate+$NH_4^+$+NADH→glutamate+$NAD^+$ and being that encoded by GDH2 of *Saccharomyces cerevisiae*;
      (b) a glutamate synthase activity catalyzing the reaction: 2-oxoglutarate+glutamine+NADH→2 glutamate+$NAD^+$ and being that encoded by GLT1 of *Saccharomyces cerevisiae*; and
      (c) a glutamine synthetase activity catalyzing the reaction: glutamate+$NH_4^+$+ATP→glutamine+ADP+Pi and being that encoded by GLN1 of *Saccharomyces cerevisiae*;
   wherein each increased enzyme activity is that of (1) an enzyme, endogenous to said cell, encoded by a nucleic acid coding sequence operably linked to at least one regulatory sequence not natively associated with said nucleic acid coding sequence, whose expression is increased as compared to the expression of the enzyme activity when said nucleic acid coding sequence is associated with its native regulatory sequence or (2) an enzyme, exogenous to said cell, encoded by a nucleic acid coding sequence, operably linked to at least one regulatory sequence, and wherein the recombinant yeast cell is further characterized by
   ii) a reduced expressible enzyme activity controlling anabolic metabolism of ammonia in said cell as a nutrient source, said reduced enzyme activity being a natively present NADPH-dependent glutamate dehydrogenase activity which reduced activity is reduced compared to the native level of activity.

2. The yeast cell of claim 1, said cell comprising an increased enzyme activity (b) and an increased enzyme activity (c).

3. The yeast cell of claim 1, said cell comprising a further increased expressible enzyme activity, said further expressible enzyme activity being the pyridine nucleotide transhydrogenase activity encoded by CTH of *Azobacter vinelandii* as harboured by *Saccharomyces cerevisiae* TN4 deposited under DSM Accession No. 12267 and being operably linked to a regulatory sequence not natively associated with said further enzyme activity in said yeast cell.

4. The yeast cell of claim 3 wherein said cell comprises no endogenous transhydrogenase activity.

5. The yeast cell of claim 1, comprising an increased enzyme activity (b).

6. The yeast cell of claim 5, wherein said GLT1 is that of the strain of *Saccharomyses cerevisiae* deposited under DSM Accession No. 12275.

7. The yeast cell of claim 1, comprising an increased enzyme activity (c).

8. The yeast cell of claim 7, wherein said GLN1 is that of the strain of *Saccharomyces cerevisiae* deposited under DSM Accession No. 12274.

9. The yeast cell of claim 1, comprising an increased enzyme activity (a).

10. The yeast cell of claim 9, wherein said GDH2 is that of the strain of *Saccharomyces cerevisiae* deposited under DSM Accession No. 12277.

11. The yeast cell of claim 1 in which said reduced enzyme activity is the result of deletion of at least part of the native nucleic acid coding sequence for the NADPH-dependent glutamate dehydrogenase, and/or of at least part of at least one native regulatory sequence associated with the native nucleic acid coding sequence.

12. The yeast cell of claim 1, which is a genetically modified *Saccharomyces, Schizosaccharomyces* or *Pichia* yeast.

13. The yeast cell of claim 1, said cell being *Saccharomyces cerevisiae* TM 19 as deposited under Accession No. DSM 12276.

14. The yeast cell of claim 1, said cell being *Saccharomyces cerevisiae* TN22 as deposited under Accession No. DSM 12277.

15. The yeast cell of claim 1, in the form of a frozen or freeze-dried preparation.

16. The yeast cell of claim 15, said cell being partly or wholly reconstitutable.

17. A composition comprising the yeast cell according to claim 1, in a carrier.

18. The composition of claim 17, wherein the carrier is a physiologically acceptable carrier.

19. The composition of claim 17, said composition being a fermentation starter culture.

20. The recombinant yeast cell of claim 1, wherein production of a first metabolite is substantially increased as compared to a yeast cell which is identical to the recombinant yeast cell except that it lacks the modifications set forth in (i) and (ii).

21. The recombinant yeast cell of claim 20, wherein said production of said first metabolite is increased by a factor of at least 1.08.

22. The recombinant yeast cell of claim 20, wherein said first metabolite is ethanol.

23. The recombinant yeast cell of claim 20, further producing a second metabolite, the production of said metabolite being substantially decreased as compared to the production of said second metabolite in a yeast cell which is identical to the recombinant yeast cell except that it lacks the modifications set forth in (i) and (ii).

24. The recombinant yeast cell of claim 23, wherein said second metabolite is glycerol.

25. A method of producing a first metabolite, said method comprising the steps of: i) cultivating a yeast cell according to claim 20 in a suitable growth medium and under such conditions that said yeast cell produces said first metabolite; and, optionally, ii) isolating said first metabolite in a suitable form; and, further optionally, iii) purifying said isolated first metabolite.

26. A method of constructing a recombinant yeast cell according to claim 20, said method comprising the steps of: 1) operably linking a first nucleotide sequence encoding an enzyme mediating said increased expressible enzyme activity with an expression signal not natively associated with said first nucleotide sequence; and 2) operably linking a second nucleotide sequence encoding an enzyme mediating for said reduced expressible enzyme activity with a regulatory sequence not natively associated with said second nucleotide sequence, said regulatory sequence generating a reduced expression of said second nucleotide sequence.

27. The yeast cell of claim 1 in which said at least one regulatory sequence not natively associated with said coding sequence is a promoter.

28. The yeast cell of claim 1 in which the reduced enzyme activity is an eliminated activity.

29. The yeast cell of claim 1 in which at least one said increased enzyme activity is that of an enzyme endogenous to the cell.

30. The yeast cell of claim 29 in which said endogenous enzyme is encoded by its native coding sequence.

31. The yeast cell of claim 1 in which said reduced enzyme activity is the result of operably linking at least one regulatory sequence, not natively associated with the coding sequence encoding the native NADPH-dependent glutamate dehydrogenase of (ii), with said coding sequence, so that expression of said native enzyme is reduced.

32. The yeast cell of claim 1 in which said reduced enzyme activity is the result of repression of expression.

33. The recombinant yeast cell of claim 1, comprising:
at least one increased expressible yeast enzyme activity controlling anabolic metabolism of ammonia in said cell as a nutrient source, said increased enzyme activity being selected from the group consisting of:
   (a) a glutamate dehydrogenase activity catalyzing the reaction: 2-oxoglutarate+$NH_4^+$+NADH→glutamate+$NAD^+$ and being that encoded by GDH2 of the strain of *Saccharomyces cerevisiae* deposited under DSM Accession No. 12277;
   (b) a glutamate synthase activity catalyzing the reaction: 2-oxoglutarate+glutamine+NADH→2 glutamate+$NAD^+$ and being that encoded by GLT1 of the strain of *Saccharomyces cerevisiae* deposited under DSM Accession No. 12275; and
   (c) a glutamine synthetase activity catalyzing the reaction: glutamate+$NH_4^+$+ATP→glutamine+ADP+Pi and being that encoded by GLN1 of the strain of *Saccharomyces cerevisiae* deposited under DSM Accession No. 12274;

wherein each increased enzyme activity is that of
   (1) an enzyme, endogenous to said cell, encoded by a nucleic acid coding sequence operably linked to at least one regulatory sequence not natively associated with said nucleic acid coding sequence, whose expression is increased as compared to the expression of the enzyme activity when said nucleic acid coding sequence is associated with its native regulatory sequence, or
   (2) an enzyme, exogenous to said cell, encoded by a nucleic acid coding sequence, operably linked to at least one regulatory sequence, and wherein the recombinant yeast cell is further characterized by
   (ii) a reduced expressible enzyme activity controlling anabolic metabolism of ammonia in said cell as a nutrient source, said reduced enzyme activity being a natively present NADPH-dependent glutamate dehydrogenase activity which reduced activity is reduced compared to the native level of activity.

* * * * *